US011068799B2

(12) United States Patent
Chang et al.

(10) Patent No.: US 11,068,799 B2
(45) Date of Patent: Jul. 20, 2021

(54) SYSTEMS AND METHODS FOR CAUSAL INFERENCE IN NETWORK STRUCTURES USING BELIEF PROPAGATION

(71) Applicant: ICAHN SCHOOL OF MEDICINE AT MOUNT SINAI, New York, NY (US)

(72) Inventors: Rui Chang, New York, NY (US); Eric E. Schadt, New York, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 1017 days.

(21) Appl. No.: 15/508,880

(22) PCT Filed: Sep. 3, 2015

(86) PCT No.: PCT/US2015/048366
§ 371 (c)(1),
(2) Date: Mar. 3, 2017

(87) PCT Pub. No.: WO2016/036958
PCT Pub. Date: Mar. 10, 2016

(65) Prior Publication Data
US 2017/0206460 A1   Jul. 20, 2017

Related U.S. Application Data

(60) Provisional application No. 62/046,670, filed on Sep. 5, 2014.

(51) Int. Cl.
*G06N 7/00* (2006.01)
*G16B 40/00* (2019.01)
(Continued)

(52) U.S. Cl.
CPC .............. *G06N 7/005* (2013.01); *G16B 5/00* (2019.02); *G16B 20/00* (2019.02); *G16B 40/00* (2019.02); *G06N 7/00* (2013.01)

(58) Field of Classification Search
None
See application file for complete search history.

(56) References Cited

U.S. PATENT DOCUMENTS 7,627,537 B2 * 12/2009 Lai ..................... G06N 7/005
                                                              706/12
2006/0164997 A1   7/2006 Graepel et al.
(Continued)

FOREIGN PATENT DOCUMENTS

WO   WO 2007/147166 A2   12/2007
WO   WO 2009/063446 A2   5/2009

OTHER PUBLICATIONS

Markowetz, Probabilistic Models for Gene Silencing Data, Doctoral Thesis, Free University Berlin, 2005, pp. 1-94 (Year: 2005).*
(Continued)

*Primary Examiner* — Wilbert L Starks
(74) *Attorney, Agent, or Firm* — Morgan, Lewis & Bockius LLP

(57) ABSTRACT

Systems and method for perturbing a system include obtaining directed acyclic/cyclic graph candidates $\{G_1, \ldots, G_N\}$ for the system. Each $G_i$ in $\{G_1, \ldots G_N\}$ includes a causal relationship between a parent and child node. $\{G_1, G_N\}$ demonstrate Markov equivalence. Observed data D is obtained for the nodes. For each respective $G_i$, the marginal probability of a parent node $x_i$ in $G_i$ is clamped by D while computing a distribution of marginal probabilities for a child node $y_i$, by Bayesian network or Dynamic Bayesian network belief propagation using an interaction function. The observed distribution for the child node $y_i$, in D and the computed distribution of marginal probabilities for the child node $y_i$ are scored using a nonparametric function, and such scores inform the selection of a directed/cyclic graph from $\{G_1, \ldots, G_N\}$. The system is perturbed using a perturbation that relies upon a causal relationship in the selected directed acyclic/cyclic graph.

20 Claims, 50 Drawing Sheets

(51) Int. Cl.
  *G16B 5/00*    (2019.01)
  *G16B 20/00*   (2019.01)

(56)  References Cited

U.S. PATENT DOCUMENTS

| | | |
|---|---|---|
| 2008/0071465 A1 | 3/2008 | Chapman et al. |
| 2010/0179930 A1 | 7/2010 | Teller et al. |
| 2011/0112747 A1 | 5/2011 | Downs et al. |
| 2012/0065788 A1 | 3/2012 | Harper, III et al. |
| 2012/0155704 A1 | 6/2012 | Williams et al. |
| 2013/0151452 A1 | 6/2013 | Wang et al. |
| 2014/0095425 A1 | 4/2014 | Sipple |

OTHER PUBLICATIONS

Xiaotong, Lin, Thesis "Bayesian Network Learning and Applications in Bioinformatics", (whole document), Jul. 26, 2002.
"Empirical evaluation of scoring functions for Bayesian network model selection" (Jul. 26, 2012), BMC Bioformatics 2012, 13 (Suppl 15):S14. Empirical evaluation of scoring functions for Zhifa et al. Jul. 26, 2012(Jul. 26, 2012) (#2.2.2, pp. 7-9, #2.3, #3.2.1).

* cited by examiner

| GLX,TRH→GLC | GLC→G6P | G6P→G1P | G1P→UDG | G6P,UDG→T6P | T6P→TRH | Total Score |
|---|---|---|---|---|---|---|
| 3.41012 | 4.47932 | 5.3111 | 4.2021 | 4.3202 | 4.21400 | 25.93696 |
| GLX→GLC | GLC,T6P→G6P | G6P→G1P | G1P,T6P→UDG | TRH→T6P | GLC→TRH | Total Score |
| 3.40264 | 4.47932 | 5.27015 | 4.08511 | 4.04915 | 4.04646 | 25.33285 |
| GLX→GLC | GLC→G6P | G6P→G1P | G1P,T6P→UDG | G6P→T6P | GLC→TRH | Total Score |
| 3.40264 | 4.584723 | 4.99065 | 4.09345 | 4.16278 | 4.04646 | 25.26973 |

Figure 47

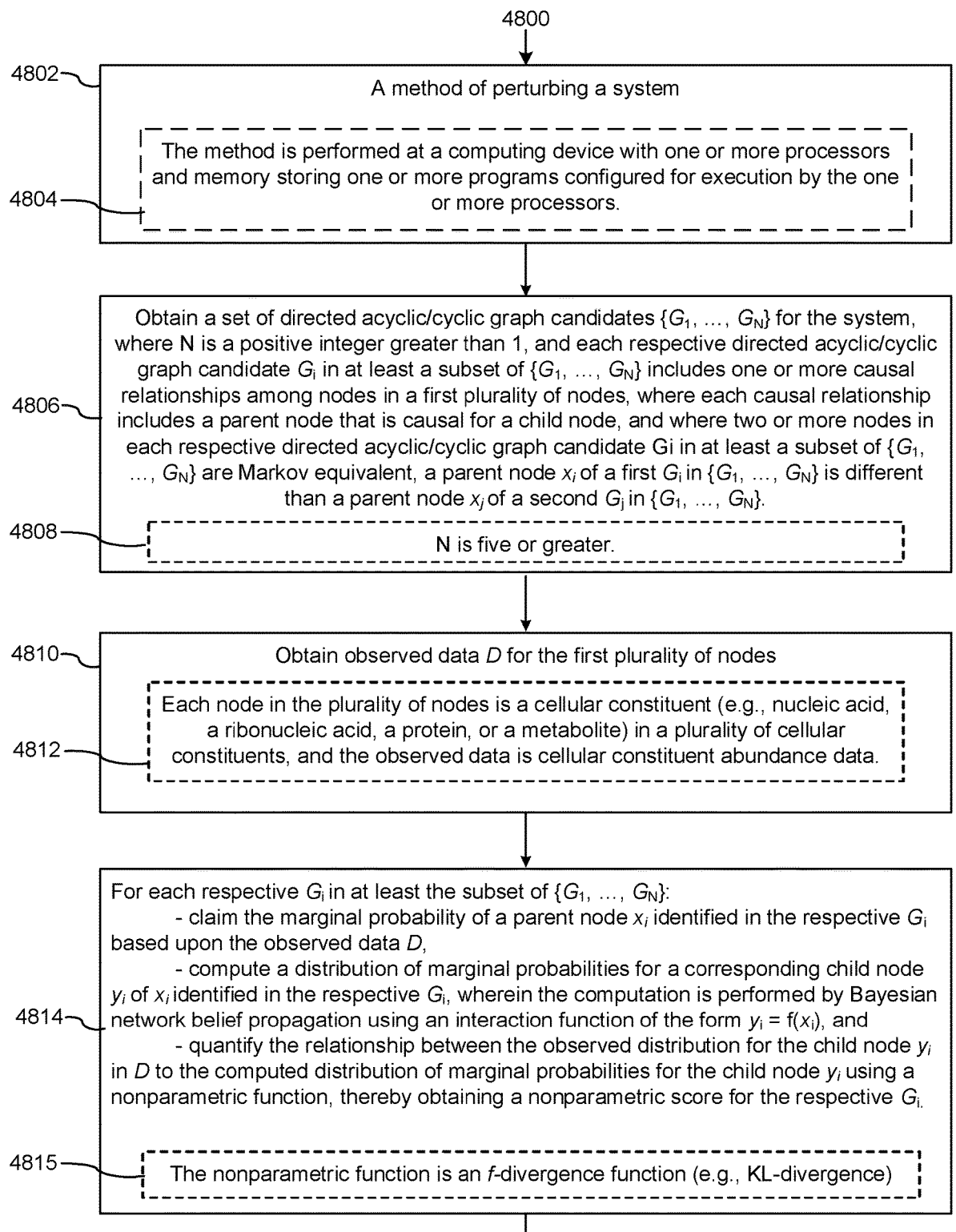

ered as canonical pathways are routinely shown to be incomplete and even inaccurate in different contexts. Therefore, methods that can help infer the causal relationships among the vast sea of phenotypes that can be scored are needed to better focus the type of hypotheses that can be experimentally pursued in a laboratory setting.

SYSTEMS AND METHODS FOR CAUSAL INFERENCE IN NETWORK STRUCTURES USING BELIEF PROPAGATION

CROSS REFERENCE TO RELATED APPLICATION

This Application claims priority to U.S. Provisional Application No. 62/046,670 entitled "Systems and Methods for Causal Inference in Network Structures Using Belief Propagation," filed Sep. 5, 2015, which is hereby incorporated by reference herein in its entirety.

STATEMENT REGARDING FEDERALLY SPONSORED RESEARCH OR DEVELOPMENT

This invention was made with government support under R01MH097276 and R01AG043076 awarded by the NIH. The government has certain rights in the invention.

TECHNICAL FIELD

The disclosure relates generally to methods of inferring causality between parent and child nodes in directed and partial directed and acyclic/cyclic graphs that represent systems and using this information to perturb such systems.

BACKGROUND

Elucidation of causal relationships in networks has extensive commercial applications. For example, Kleinbert (Kleinberg et al., 2010 "Investigating Causal Relationships in Stock Returns with Temporal Logic Based Methods," arXiv:1006.1791, 2010) considers the causal relationships between stock prices in order to predict how components of the stock market will behave.

Another example of the importance of elucidation of causal relationships is found in biomedical research where work is undertaken to elucidate the networks of molecular interactions underlying complex human phenotypes such as cancer and Alzheimer's disease. Whole genome sequencing, RNA sequencing, methylation profiling, and mass spectroscopy and NMR based metabolite and protein profiling technologies have been applied to a wide range of biological problems and have contributed to discoveries relating to the complex network of biochemical processes as well as to the reconstruction of gene networks underlying living systems (Schadt et al., 2005, "An integrative genomics approach to infer causal associates between gene expression and disease," Nature Genetics 37, pp. 710-717) and common human diseases (Emilsson et al., 2008, "Genetics of gene expression and its effect on disease," Nature 452, pp. 423-428; Chen et al, 2008, "Variations in DNA induce changes in molecular network states that in turn lead to variations in obesity and related metabolic traits," Nature 452, pp. 429-435. Such work has demonstrated that the technology now exists to score molecular and higher order phenotypes and genotypes on a massive scale (e.g., whole genome sequencing, RNA sequencing, methylation profiling, and mass spectroscopy and NMR based metabolite and protein profiling technologies), producing rich patterns of associations among molecular and higher order features that have the potential to elucidate the complexity of pathways in living organisms. However, what remains missing in biology is knowledge of the comprehensive set of pathways that operate in living organisms, the structure of these pathways, how they interact with each other, how they change over time in response to different biological contexts etc. Even what are considered as canonical pathways are routinely shown to be incomplete and even inaccurate in different contexts. Therefore, methods that can help infer the causal relationships among the vast sea of phenotypes that can be scored are needed to better focus the type of hypotheses that can be experimentally pursued in a laboratory setting.

State-of-the-art statistical learning methods assume a Markov condition for gene network reconstructions as a way to reduce the complexity of the joint probability distribution that graphical network structures represent. Algorithms based on Markov conditions can learn the correct causal relationships up to Markov equivalence given a large enough sample size (Friedman Koller, 2003, "Being Bayesian About Network Structure. A Bayesian Approach to Structure Discovery in Bayesian Networks," Machine Learning 50(1-2), pp. 95-125). However, because the structures represented within a given equivalence class are statistically indistinguishable from one another, it is not possible to further resolve the correct causal relationships within a class without introducing perturbations that break the symmetry giving rise to this equivalence. To at least partially address this problem in the biomedical setting, a Bayesian network learning framework to improve causal inference within Markov equivalence classes by integrating genotypic data associated with molecular phenotypes (e.g., expression quantitative trait loci, or eQTL) and disease traits as an asymmetric and systematic source of perturbations has been proposed (Schadt et al., 2005, "An integrative genomics approach to infer causal associates between gene expression and disease," Nature Genetics 37, pp. 710-717, which is hereby incorporated herein by reference). This approach has been effective in untangling the causality in gene networks given it leverages the propagation of structural asymmetry required to break Markov equivalence.

More specifically, there have been several methods developed to infer causality between pairwise variables given multivariate data. A new class of methods, referred to as Information Geometric Causal Inference (IGCI) methods (Dominik et al., 2012, "Information-geometric approach to inferring causal directions," Artificial Intelligence 182-183), defines classic measures of independence among variables in terms of orthogonal components of the joint probability distribution of these variables, as a way to leverage more information regarding the relationships among them. This approach stands in contrast to traditional approaches in which data informing on the relationships among variables of interest are extracted using only conditional dependencies. In the IGCI methods, to infer whether X causes Y, orthogonality is computed between the conditional distribution $P_{Y|X}$ and $P_X$, which are then compared to the values computed for $P_{X|Y}$ and $P_Y$. If the relationship "X causes Y" is true, then the orthogonality metric is such that the causal hypothesis Y causes X is implausible. This asymmetry between cause and effect becomes particularly simple if X and Y are deterministically related. The case of a nonlinear relationship between X and Y, i.e. Y=f(X), where f is a nonlinear function, can also be considered for causal inference in the presence of additive noise (Hoyer et al., 2008, "Nonlinear causal discovery with additive noise models," Neural Information Processing Systems (NIPS). The nonlinearity provides information on the underlying causal model and thus allows more aspects of the true causal mechanism to be identified. An alternative approach, referred to as functional causal modeling (a.k.a. structural causal or nonlinear structural equation modeling), involves a joint distribution function that along with a graph satisfies the causal Markov assumption (Schlkopf et al., 2012, "On Causal and Anticausal Learning," International Conference on Machine Learning). This functional form allows one to distinguish between X→Y and X←Y.

Given the importance of inferring causal relationships, what is needed in the art are improved and more general methods for inferring causality in real structures including cyclic, v-structures (one child node with more than one parent), based on multivariate datasets. For instance, given the recovery of accurate mechanistic networks is an important first-step to understanding the pathophysiology of human disease and how best to diagnose and treat it, improved methods to accurately infer causal relationships are needed.

SUMMARY

Disclosed implementations address the above deficiencies and other problems associated with inferring causal relationships. The instant disclosure provides systems and methods for inferring causal relationships in multivariate data (e.g., among molecular and higher order phenotypes). This is an important step, for example, in elucidating the complexity of pathways in living organisms. The disclosed systems and methods infer causality in a way that is no longer constrained by the conditional dependency arguments that limit the ability of statistical causal inference methods to resolve causal relationships within sets of graphical models that are Markov equivalent. As an example, the disclosed systems and methods utilize Bayesian belief propagation to infer the responses of perturbation events on molecular traits given a hypothesized graph structure. A distance measure between the inferred response distribution and the observed data is defined to assess the 'fitness' of the hypothesized causal relationships. To test the systems and methods of the present disclosure, causal relationships are inferred within equivalence classes of gene networks in which the form of the functional interactions that are possible are assumed to be known.

One aspect of the present disclosure provides a method of perturbing a system. The method comprises obtaining a set of directed acyclic/cyclic graph candidates $\{G_1, \ldots, G_N\}$ for the system, wherein N is a positive integer greater than 1 (e.g., two or more, three or more, four or more, five or more etc.) and each respective directed acyclic/cyclic graph candidate $G_i$ in at least a subset of $\{G_1, \ldots, G_N\}$ includes one or more causal relationships among nodes in a first plurality of nodes. Each causal relationship includes a parent node that is causal for a child node. Two or more nodes in each respective directed acyclic/cyclic graph candidate $G_i$ in at least a subset of $\{G_1, \ldots, G_N\}$ are Markov equivalent. Moreover, a parent node $x_i$ of a first $G_i$ in $\{G_1, \ldots, G_N\}$ is different than a parent node $x_j$ of a second $G_j$ in $\{G_1, \ldots, G_N\}$. As used herein, the term acyclic/cyclic means "acyclic and/or cyclic."

Observed data D for the first plurality of nodes is obtained (e.g., stock market prices, cellular constituent abundance data, etc.). For each respective $G_i$ in at least the subset of $\{G_1, \ldots, G_N\}$, the marginal probability of a parent node $x_i$ identified in the respective $G_i$ is claimed (fixed) based upon the observed data D. A distribution of marginal probabilities is computed for a corresponding child node $y_i$ of $x_i$ identified in the respective $G_i$, where the computation is performed by Bayesian network belief propagation using an interaction function of the form $y_i = f(x_i)$.

The relationship between the observed distribution for the child node $y_i$ in D to the computed distribution of marginal probabilities is computed for the child node $y_i$ using a nonparametric function, thereby obtaining a nonparametric score for the respective $G_i$. A directed acyclic/cyclic graph is selected from $\{G_1, \ldots, G_N\}$ based at least in part upon the quantified nonparametric score for the selected directed acyclic/cyclic graph. The system is perturbed using a perturbation that relies at least in part upon the causal relationship between the parent node x and the child node y identified in the selected directed acyclic/cyclic graph.

In some embodiments, the system is a biological pathway in a living organism and the perturbation is a pharmaceutical composition. In some embodiments, the system is a financial market (e.g., security exchange market, currency exchange market, etc.), the parent node is a first entity in the financial market, the child node is a second entity in the financial market, and the perturbation is a trade or exchange in the first entity or the second entity.

In some embodiments, the nonparametric function used is an f-divergence function. In some embodiments, the nonparametric function is KL-divergence and the quantifying the relationship between the observed distribution for the child node $y_i$ in D to the computed distribution of marginal probabilities for the child node $y_i$ using a nonparametric function comprises dividing the range of the observed data in D for the parent node $x_i$ of the respective $G_i$ into L segments, wherein $D \in R$ is rescaled to $D \in [0,1]$, and maximizing the data likelihood function $P(D|G_i, \hat{\theta})$ in each of the L segments, where $\hat{\theta}$ is sampled uniformly in $[0,1]$, by identifying the parameter $\hat{\theta}^l$ that minimizes KL-divergence between the observed distribution for the child node $y_i$ to the computed distribution of marginal probabilities for the child node $y_i$ for each segment in L. In some such embodiments, the parameter $\hat{\theta}^l$ that minimizes KL-divergence for a segment in L is computed as:

$$\operatorname*{argmin}_{\theta} \left\{ \sum_{k=0}^{K} p_k^l \ln(p_k^l / q_k^l) + \sum_{k=0}^{K} q_k^l \ln(q_k^l / p_k^l) \right\}$$

where
a total of K bins are defined that are evenly distributed in $[0,1]$,
$p_k^l$=the frequency for the marginal probabilities for the child node in the $k^{th}$ bin and the $l^{th}$ segment, and
$q_k^l$=the frequency for the observed child data from D in the $k^{th}$ bin and the $l^{th}$ segment.

In some embodiments the interaction function $y_i = f(x_i)$ is a linear function, a non-linear function, a monotonic function, a non-monotonic function, a concave function, a step function, a periodic function, a hill function, or a non-monotonic nonlinear function.

In some embodiments, the Bayesian network belief propagation is performed by a join-tree propagation, cut-set conditioning, or a hybrid thereof. In some embodiments, the Bayesian network belief propagation is performed by stochastic simulation. In some embodiments, the quantifying the relationship between the observed distribution for the child node $y_i$ in D to the computed distribution of marginal probabilities for the child node $y_i$ using a nonparametric function comprises representing a relationship between $x_i$ and $y_i$ as a cubic spline.

In some embodiments, the parent node is part of a v-structure or a feedback loop.

In some embodiments, each acyclic/cyclic graph candidate $G_i$ in $\{G_1, \ldots, G_N\}$ includes a plurality of causal relationships among nodes in the first plurality of nodes and the computing the distribution of marginal probabilities for a corresponding child node $y_i$ of $x_i$ identified in the respective G comprises performing Bayesian network belief propagation across a plurality of causal relationships among nodes in the first plurality of nodes.

In some embodiments, the system is metabolic pathway, each node in the plurality of nodes is a metabolite in the metabolic pathway, the observed data D is metabolite steady-state or time-series concentration data, and each directed acyclic/cyclic graph candidate $G_i$ in at least a subset of $\{G_1, \ldots, G_N\}$ is a different model of causal dependencies between metabolites in the metabolic pathway.

In some embodiments, each node in the plurality of nodes is a cellular constituent in a plurality of cellular constituents, and the observed data is cellular constituent (e.g., a nucleic acid, a ribonucleic acid, a protein, metabolite, etc.) abundance data (either in steady-state or time-series).

Another aspect of the present disclosure provides a computing device, comprising one or more processors, memory and one or more programs stored in the memory configured for execution by the one or more processors. The one or more programs comprise instructions for (A) obtaining a set of directed acyclic/cyclic graph candidates $\{G_1, \ldots, G_N\}$ for the system, where N is a positive integer greater than 1, and each respective directed acyclic graph candidate $G_i$ in at least a subset of $\{G_1, \ldots, G_N\}$ includes one or more causal relationships among nodes in a first plurality of nodes. Furthermore, a parent node $x_i$ of a first $G_i$ in $\{G_1, \ldots, G_N\}$ is different than a parent node $x_j$ of a second $G_j$ in $\{G_1, \ldots, G_N\}$. Each causal relationship includes a parent node that is causal for a child node. Furthermore, in some embodiments, two or more nodes in each respective directed acyclic/cyclic graph candidate $G_i$ in at least a subset of $\{G_1, \ldots, G_N\}$ are Markov equivalent. In some embodiments, none of the directed acyclic/cyclic graph candidate $G_i$ in $\{G_1, \ldots, G_N\}$ are Markov equivalent. In some embodiments, at least a subset of $\{G_1, \ldots, G_N\}$ exhibit complex structures, such as cycles, v-structure, and the like. Observed data D for the first plurality of nodes is obtained. For each respective $G_i$ in at least the subset of $\{G_1, \ldots, G_N\}$, the marginal probability of a parent node $x_i$ identified in the respective $G_i$ is clamped based upon the observed data D. A distribution of marginal probabilities for a corresponding child node $y_i$ of $x_i$ identified in the respective $G_i$ is computed using Bayesian network belief propagation and an interaction function of the form $y_i = f(x_i)$. The interaction function is imposed for purposes of performing computations in accordance with the present disclosure. The true interaction function of the underlying data does not need to be known. In some embodiments, more than one type of interaction function is used and the performance of each interaction function is compared since the true interaction function is not necessarily known in such embodiments. In some embodiments, the interaction function is loosely confined to a general property, such as a requirement that it be nonlinear. The relationship between the observed distribution for the child node $y_i$ in D to the computed distribution of marginal probabilities for the child node $y_i$ is quantified using a nonparametric function, thereby obtaining a nonparametric score for the respective $G_i$. A directed acyclic/cyclic graph is selected from $\{G_1, \ldots, G_N\}$ based at least in part upon the quantified nonparametric score for the selected directed acyclic/cyclic graph.

Another aspect of the present disclosure provides a non-transitory computer readable storage medium storing one or more programs configured for execution by a computing device having one or more processors and memory. The one or more programs comprise instructions for (A) obtaining a set of directed acyclic/cyclic graph candidates $\{G_1, \ldots, G_N\}$ for the system, where N is a positive integer greater than 1, and each respective directed acyclic/cyclic graph candidate $G_i$ in at least a subset of $\{G_1, \ldots, G_N\}$ includes one or more causal relationships among nodes in a first plurality of nodes. Furthermore, a parent node $x_i$ of a first $G_i$ in $\{G_1, \ldots, G_N\}$ is different than a parent node $x_j$ of a second $G_j$ in $\{G_1, \ldots, G_N\}$. Each causal relationship includes a parent node that is causal for a child node. Furthermore, two or more nodes in each respective directed acyclic/cyclic graph candidate $G_i$ in at least a subset of $\{G_1, \ldots, G_N\}$ are Markov equivalent. Observed data D for the first plurality of nodes is obtained. For each respective $G_i$ in at least the subset of $\{G_1, \ldots, G_N\}$, the marginal probability of a parent node $x_i$ identified in the respective $G_i$ is clamped based upon the observed data D. A distribution of marginal probabilities for a corresponding child node $y_i$ of $x_i$ identified in the respective $G_i$ is computed using Bayesian network belief propagation and an interaction function of the form $y_i = f(x_i)$. The relationship between the observed distribution for the child node $y_i$ in D to the computed distribution of marginal probabilities for the child node $y_i$ is quantified using a nonparametric function, thereby obtaining a nonparametric score for the respective $G_i$. A directed acyclic/cyclic graph is selected from $\{(G_1, \ldots, G_N\}$ based at least in part upon the quantified nonparametric score for the selected directed acyclic/cyclic graph.

BRIEF DESCRIPTION OF THE DRAWINGS

For a better understanding of the aforementioned implementations of the invention as well as additional implementations thereof, reference should be made to the Description of Implementations below, in conjunction with the following drawings in which like reference numerals refer to corresponding parts throughout the figures.

FIG. 35, first column, lower two bar plots, respectively represent, the optimized distribution of B and C in $G_1$, where $G_1$ is defined in FIG. 2. In the first column of FIG. 35, A is the perturbed node whose value is clamped according to the dataset D and the values of B and C are inferred in $G_1$ by Bayesian network belief propagation procedure for each sampled set of model parameter θ. FIG. 35, second column, node B is considered as the parent node. Given the value of B, the belief probability of nodes A and C are inferred $G_2$ for each sampled model parameter. The distribution of the optimal predicted values A and C are respectively shown in the lower two plots of the second column of FIG. 35. FIG. 35, third column, node C is perturbed and nodes B and A are predicted sequentially (i.e., B is predicted from C and then A is predicted from predicted B in accordance with $G_3$ of FIG. 2). The distribution of the optimal predicted values for A and B are respectively shown in the lower two plots of the third column of FIG. 35.

FIG. 47 provides the causality scores for the three causal structures of FIG. 46 that were calculated in accordance with an embodiment of the present disclosure.

Reference will now be made in detail to implementations, examples of which are illustrated in the accompanying drawings. In the following detailed description, numerous specific details are set forth in order to provide a thorough understanding of the present invention. However, it will be apparent to one of ordinary skill in the art that the present invention may be practiced without these specific details.

DESCRIPTION OF IMPLEMENTATIONS

In the disclosed systems and methods, statistical methods for inferring causal structures based on multivariate datasets (e.g. gene expression data) is provided, thereby reducing the need to integrate additional data such as, in the case of the biomedical setting expression quantitative trait loci (eQTLs), to accurately infer causal relationships. The disclosed systems and methods are complementary to more integrative approaches, given it will enable accurate causal inferences in cases in which integrative approaches are not possible or not well powered. For example, even when eQTL data are available, inferring a complete causal network structure remains challenging given the conventional top-down Bayesian network learning approach decomposes the joint probability function representing a given graph into the product of local conditional probabilities based on d-separation, so that the effect of causal information stemming from eQTL-controlled root nodes will not always effectively propagate through the entire network, leaving the issue of equivalence classes unresolved at distal local structures. This issue is exacerbated as the number of nodes in the network increases, given the super-exponential rate of growth of the network space and the fact that trans-acting eQTL effects (eQTL that act on genes that are distal to the physical location of the eQTL) are difficult to detect. Therefore, the development of methods to infer causality among structures in equivalence classes remains a fundamental objective for reconstructing accurate probabilistic causal network structures. To demonstrate the utility of disclosed causal inference systems and methods, it is applied to simulated gene expression data that reflects the type of noise structures common in these high-throughput biological experiments as well as the biological relationships to be represented. In this context the ability of the disclosed systems and method to resolve Markov equivalent structures across a variety of general assumptions regarding the nature of gene-gene interactions is demonstrated. Furthermore, to show the general applicability of the disclosed systems and methods, their ability to predict the correct causal relationship between a pair of stocks based on their historic prices is also demonstrated.

Figure 1:
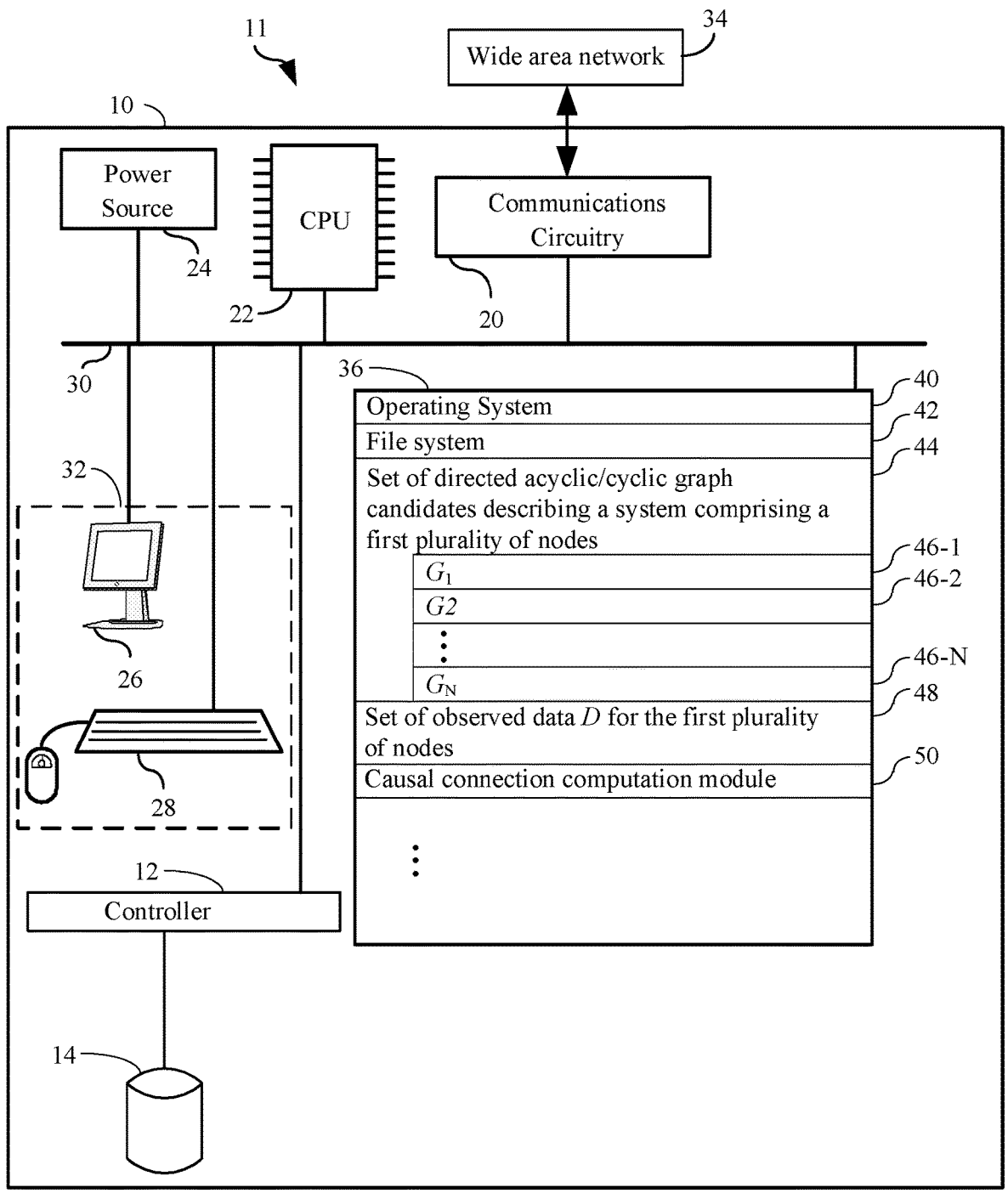
FIG. 1 illustrates a context in which some implementations operate.

FIG. 1 details just such an exemplary system 11 for use in determining causal relationships. It will be appreciated that system 11 may be a scientific apparatus or a general purpose computer system. The system preferably comprises a computer system 10 having:

- a central processing unit 22;
- a main non-volatile (non-transitory) storage unit 14, for example a hard disk drive, for storing software and data, the storage unit 14 controlled by storage controller 12;
- a system memory 36, preferably high speed random-access memory (RAM), for storing system control programs, data, and application programs, comprising programs and data loaded from non-volatile storage unit 14; system memory 36 may also include read-only memory (ROM);
- a user interface 32, comprising one or more input devices (e.g., keyboard 28, a mouse) and a display 26 or other output device;
- optionally, a network interface card 20 (communications circuitry) for connecting to any wired or wireless communication network 34 (e.g., a wide area network such as the Internet);
- a power source 24 to power the aforementioned elements; and
- an internal bus 30 for interconnecting the aforementioned elements of the system.

Operation of computer 10 is controlled primarily by operating system 40, which is executed by central processing unit 22. Operating system 40 can be stored in system memory 36. In a typical implementation, system memory 36 also includes:

- a file system 42 for controlling access to the various files and data structures;
- a set 44 of directed acyclic/cyclic graph candidates {$G_1$ (46-1), . . . , $G_N$ (46-N)} that each describe a system, where N is a positive integer greater than 1, were each respective directed acyclic/cyclic graph candidate $G_i$ 46 in at least a subset of the set 44 includes one or more causal relationships among nodes in a first plurality of nodes, where each causal relationship includes a parent node that is causal for a child node, the first plurality of nodes including two or more nodes that are Markov equivalent;
- observed data D (48) for the first plurality of nodes; and
- a causal computation module 50 for identifying the correct directed acyclic/cyclic graph 46 in the set 44 of acyclic/cyclic graph candidates given the observed data D (48).

As illustrated in FIG. 1, computer 10 comprises data such as observed data for a first plurality of nodes. Such data can be stored in any form of data storage system including, but not limited to, a flat file, a relational database (SQL), or an on-line analytical processing (OLAP) database (MDX and/or variants thereof). In some embodiments, observed data 48 is stored in a single database. In other embodiments, observed data 44 is in fact stored in a plurality of databases that may or may not all be hosted by the same computer 10. In such embodiments, some components of observed data 44 are stored on computer systems that are not illustrated by FIG. 1 but that are addressable by computer 10 across wide area network 34 (e.g., the Internet).

In some embodiments, observed data 48 and related software modules illustrated in FIG. 1 (e.g. causal connection computation module 50) are on a single computer (e.g., computer 10) and in other embodiments they are hosted by several computers (not shown). In fact, all possible arrangements of data 48 and the other components illustrated in FIG. 1 on one or more computers are within the scope of the present disclosure so long as these components are addressable with respect to each other across computer network 34 or by other electronic means. Thus, the present disclosure fully encompasses a broad array of computer systems.

A network framework is a graphical model (directed graph) for probabilistic relationships among a set of variables. As such, it encodes relationships among variables of interest including dependencies among all variables using probabilities. Specifically, a network is a directed acyclic/cyclic graph in which the nodes represent variables, the arcs signify the existence of direct causal influences between the linked variables, and the strengths of these influences are expressed by forward conditional probabilities. In some embodiments, the systems and methods of the present invention make use of directed acyclic graphs (DAGs) that imposes an acyclic limitation. Such DAGs, such as Bayesian networks, have been generally used to develop causal models that rely upon the decomposability of the joint probability of nodes in the network. In some embodiments, however, the systems and methods of the present invention make use of directed acyclic graphs (DAGs) that are not restricted by such decomposability principals. Directed networks allow one to learn about casual relationships between variables. This is useful when trying to gain understanding about a problem domain (e.g., relationship between stock prices, elucidation of molecular pathways, etc.). Further, knowledge of causal relationships allows for the formation of predictions in the presence of interventions (e.g., sale of a company, perturbation of a molecular pathway with a drug, etc.). In one example, a marketing analyst may want to know whether or not it is worthwhile to increase exposure of a particular advertisement in order to increase the sales of a product. To address this question, it is necessary to determine whether or not the advertisement is a cause for increase sales, and to what degree. The use of directed networks helps to answer such questions even when no experiment about the effects of increased exposure is available.

The disclosed systems and methods utilize the inherent probabilistic inference capability of the directed network (acyclic/cyclic DAG) framework to generate predictions of hypothesized child (response) nodes using the observed data of the hypothesized parent (causal) nodes. A distance metric in probability space is then defined to assess how well the predicted distribution of child nodes matches the distribution of their observed values. In this way, different structures within an equivalence class can be evaluated to determine the one best supported by the data. This modeling approach further enables propagating the effects of a parent node to child nodes that may be greater than a path length of one from the parent, thereby enabling causality inference in a chain of nodes or more complex network structures.

In the disclosed systems and methods, the general posterior probability of the graphical structure as defined in conventional Bayesian network approaches (Hackerman, 1996, "A Tutorial on Learning with Bayesian Networks," Technical Report, MSR-TR-95-06, Microsoft Research, Redmond Wash.) which is hereby incorporated by reference herein) is reformatted, with X representing the vector of variables in the network,
E being the evidence (e.g., observed data of parent nodes),
D denoting the observed data (e.g., observed data of child nodes),
G being the graphical network structure (ground truth) to infer, and
θ being a vector of model parameters.

From this, the posterior probability is written as P(G|D)=P(D|G)P(G)/P(D), where the marginal probability P(D|G) is expressed as an integral over the parameters, given a particular graphical structure: $P(D|G) = \int_\theta P(D|G, \theta) P(\theta|G) d\theta$. Unlike the traditional Bayesian Dirichlet score, D contains continuous values, and thus, the likelihood of the data is not derived from a multinomial distribution, but a continuous density function whose form is estimated using a kernel density estimation procedure. In addition, the parameter prior P(θ|G) does not follow a Dirichlet distribution but rather is either described by a set of non-parametric constraints in parameter space or is sampled from a uniform distribution defined in its range. Given this, the above integral has no analytical solution. The data likelihood is optimized by estimating θ using maximum-a-posterior (MAP) estimation:

$$P(D|G) \approx P(D|G, \hat{\theta}) \quad (1)$$

where $\hat{\theta} = \text{argmax}_\theta \{P(D|G, \theta) P(\theta|G)\}$. A sampling procedure (e.g., Monte Carlo) is used to sample θ from P(θ|G), thereby evaluating the likelihood for each parameter sample.

From the above, it is seen that the data likelihood, denoted P(D|G, θ), needs to be calculated and optimized. To calculate and optimize the data likelihood P(D|G, θ), belief propagation is incorporated as a subroutine in the causal inference procedure to predict the marginal probabilities of all response variables given the observed data for the predictor variables for a given causal structure (G). In this instance, the marginal probability of X given G and the sampled parameter θ is calculated via belief propagation.

Belief propagation in is disclosed in Pearl, 2009, *Causality: Models, Reasoning, and Inference*, Second Edition, Cambridge University Press, pp. 20-21, which is hereby incorporated by reference herein. It is based on the computation of P(b|a), where a is a set of observations and b is a set of variables that are deemed important for prediction. As noted in Pearl, given a joint distribution P, the computation of P(b|a) invokes an application of Bayes' rule to yield:

$$P(b|a) = \frac{\sum_S P(b, a, S)}{\sum_{b,S} P(b, a, S)}$$

where S stands for the set of all variables excluding a and b. Because every network defines a joint probability P, P(b|a) can be computed from a directed acyclic/cyclic graph G and the conditional properties $P(a_i|pc_i)$ defined on the families of G. Efficient methods for performing this computation efficiently include a message passing architecture limited to tree propagation in which each variable is assigned a simple processor and is permitted to pass messages asynchronously to its neighbors until equilibrium is achieved (in a finite number of steps). See Pearl 1982, "Reverend Bayes on inference engines: A distributed hierarchical approach," *Proceedings AAAI National Conference on AI*, pp. 133-136, Pittsburgh, Pa.; Kim and Pearl, 1983, "A computational model for combined causal and diagnostic reasoning in inference systems, *Proceedings of the Eighth international Joint Conference on Artificial Intelligence* (IJCAI-83), pages 190-193, each of which is hereby incorporated by reference. Methods that extend this tree propagation to general networks include, but are not limited to, Lauritzen and Spiegl-halter's method of join-tree propagation and the method of cut-set conditioning. See Pearl, 1988, *Probabilistic Reasoning in Intelligent Systems*," Morgan Kaufmann, San Mateo, Calif., pp. 204-210, and Jensen, 1996, *An Introduction to Bayesian Networks*, Springer, New York 1996, each of which is hereby incorporated herein by reference. In the join-tree method, the network is decomposed into clusters that form tree structures and the set of variables in each such cluster is treated as a compound variable that is capable of passing messages to its neighbors. In the cut-set conditions method, a set of variables is instantiated (given specific values) that the remaining network forms a tree. The belief propagation is then performed on that tree, and a new instantiation chosen, until all instantiations have been exhausted; and the results are then average. Hybrid combinations of these two algorithms may also be used. See Shachter et al., 1994, "Global conditioning for probabilistic inference in belief networks," in *Uncertainty in Artificial Intelligence*, pp. 514-524, Lopez de Mantaras and Poole, editors, Morgan Kaufmann, San Francisco Calif.; and Dechter, 1996, "Topological parameters for time-space tradeoff," in *Proceedings of the Twelfth Conference on Uncertainty in Artificial Intelligence*, pages 220-227, Horvitz and Jensen, eds., Morgan Kaufmann, San Francisco, 1996, each of which is hereby incorporated by reference. Moreover, approximation methods such as stochastic simulation, can also be used to perform belief propagation. See Pearl, 1988, *Probabilistic Reasoning in Intelligent Systems*," Morgan Kaufmann, San Mateo, Calif., pp. 210-223, which is hereby incorporated herein by reference.

As noted above, the disclosed systems and methods are not limited to directed acyclic graphs. In some embodiments, the directed graphs include cyclic structure. If the directed graph contains one or more cycles, the marginal probability of every node is calculated by forward sampling where the convoluted cyclic structure is unrolled over time into a finite number of 2-time-slice Bayesian networks. This finite number of 2-time-slice Bayesian network is referred to herein as a Dynamic Bayesian network. Marginal probability is propagated from parents at time slice t−1 to child node at time slice t by sum. See Murphy, 2002, "Dynamic Bayesian Networks: Representation, Inference and Learning, Ph.D. Dissertation, University of California, Berkeley, which is hereby incorporated by reference.

In the disclosed systems and methods, the Bayesian belief inference P(X|E, G, θ) is used to calculate the data likelihood P(D|G, θ) given in Eq. 1, where E and D represent the observed data on the parent and child nodes, respectively. First, to avoid confusion, the notation $X_b$ is used to describe the binary variable in the probability space mapped from the continuous variable X∈R. Second, the original observation data is rescaled so that it falls into the interval [0,1] (see discussion below). Third, a hidden variable H is introduced to fully specify the data likelihood as $$P(D|G, \theta) = \int_H P(D|H) P(H|G, \theta) \quad (2)$$

Given G and θ, the soft evidence enters $P(X_b|E, G, \theta)$ as the observed, rescaled data D, which effectively "clamps" (or fixes) the marginal probability of the parent nodes, from which the marginal probabilities of the child nodes are predicted via belief propagation in the Bayesian network or Dynamic Bayesian network (in the case where the network includes cyclic structure). These marginal probabilities are then used to define the hidden data H, which are used to construct the marginal data likelihood in Eq. 2. In probability space, the belief inference is deterministic, i.e. given a causal structure G, a specific set of parameters θ, and evidence E, $P(X_b|E, G, \theta)$ is uniquely determined. In Eq. 2, when $H=P(X_b|E, G, \theta)$, $P(H|G, \theta)=1$ and 0 otherwise, the data marginal likelihood in Eq. 2 can be re-written as $$P(D|G,\theta)=P(D|H(G,\theta))=P(D|P(X_b|E,G,\theta)) \quad (3)$$

The inner probability in Equation 3 describes the marginal belief of the binary variable $X_b$ in probability space to which the original continuous variable X has been mapped. This belief probability is a linear function between the child and parent marginal probabilities, multiplied by the conditional probabilities determined by sampling over the uniform distribution the parameters θ are assumed to follow:

$$P(X_b^{chd}=k)=\Sigma_i[P(X_b^{chd}=k|X_b^{\pi}=C_i)P(X_b^{\pi}=C_i)] \quad (4)$$

in which,
$X_b^{\pi}$ represents $X_b$ for the parent node,
$X_b^{chd}$ represents $X_b$ for the child node, and
$C_i$ represents the $i^{th}$ configuration of the parent nodes.
For example, given the hypothesis "gene A activates gene B," the marginal belief is calculated as $$P(B)=P(B|A)P(A)+P(B|\overline{A})(1-P(A))=[P(B|A)-P(B|\overline{A})]P(A)+P(B|\overline{A}) \quad (5)$$

In this example, the conditional probability distribution $\theta=\{[P(B|A),P(B|\overline{A})]\}$ is the parameter sampled from the uniform distribution on 0,1]. This belief propagation can be examined by a linear regression of the form $P(B)=\beta P(A)+C$, where $\beta=(P(B|A),P(B|\overline{A}))$ and $C=P(B|\overline{A})$, given probability measures are constrained to be between 0 and 1, $\beta\in[-1,1]$ and $C\in[0,1]$. These constraints, which derive from probability theory, give rise to the asymmetric basis of the disclosed approach for causal inference. In this method, binary variables in probability space are assumed, where the belief probability of a binary variable is defined as the level of belief on that variable observed in its maximal state (i.e., $P(X_b=1)$) or minimal state (i.e., $P(X_b=0)$). When X is equal to its minimum (or maximum) value in the real valued space D, in probability space $X_b$ is observed in its minimum or maximum) state, and therefore, this observed sample will correspond to $Pr(X_b=0)=1$ or $(r(X_b=1)=0)$ in probability space. As the value of X varies between its minimum and maximum values, the belief probability of the binary mapping of this variable will vary between [0,1]. The Bayesian interpretation of the belief probability allows for the comparison of the inferred belief probability to the real-valued observed data by implicitly assuming that the original data D and the marginal probabilities of H are positively correlated, though the precise kinetics of this correlation is unknown. To make such a comparison, $D\in R$ is rescaled to $D\in[0,1]$.

Note that, the algorithm, especially, the belief propagation in Eq. 4, naturally extends to the assumption of N-nary nodes. For example, if it is assumed that A and B are tri-nary nodes, i.e. N=3, $$P(B)=P(B|A=1)P(A=1)+P(B|A=0)P(A=0)+P(B|A=2)(1-P(A=1)-P(A=0)) \quad (6)$$

Since the exact function mapping between real values and their belief probabilities is unknown, a non-parametric metric, e.g. Kullback-Liebler (KL) divergence, is used to compare the distribution of real observations to the distribution of predicted marginal probabilities.

In probability theory and information theory, the Kullback-Leibler divergence (also information divergence, information gain, relative entropy, or KLIC; here abbreviated as KL divergence) is a non-symmetric measure of the difference between two probability distributions P and Q. See Kullback and Leibler, 1951, "On Information and Sufficiency," Annals of Mathematical Statistics 22 (1): pp. 79-86; Kullback, *Information theory and statistics*, John Wiley and Sons, NY; and Kullback, 1987, "Letter to the Editor: The Kullback-Leibler distance," The American Statistician 41(4), pp. 340-341, each of which is hereby incorporated herein by reference in its entirety. Specifically, the KL divergence of Q from P, denoted KL(P∥Q), is a measure of the information lost when Q is used to approximate P. See, for example, Burnham and Anderson, 2002, *Model Selection and Multi-Model Inference: A Practical Information-Theoretic Approach*, Springer, Second Edition, p. 51, which is hereby incorporated by reference. The KL divergence measures, for example, the expected number of extra bits required to code samples from P when using a code based on Q, rather than using a code based on P. Typically P represents the "true" distribution of data, observations, or a precisely calculated theoretical distribution. The measure Q typically represents a theory, model, description, or approximation of P. The KL divergence is not symmetric: the KL divergence from P to Q is generally not the same as that from Q to P.

If the predicted and observed distributions of the child nodes match well, the predictions based on G and θ are deemed to well reflect the observed data D, which results in a smaller value of the KL-divergence. To force the KL divergence to behave as a true probability measure, symmetry and normalization modifications are made to this function defined on D and H such that $k(D,H)=1-\exp[-(KL(D\|H)+KL(H\|D))/2]$. Now, the data likelihood function in Equation 3 can be defined by any normalized monotonic decreasing function on the kernel. In some embodiments, for model selection, S is set to $-\log(K(D,H))$ to represent the posterior score of the model, which is negatively correlated with the kernel value. To optimize the model, this score is maximized, which is equivalent to minimizing the KL-divergence.

The calculation of the KL-divergence involves comparing the real valued observed data D to the inferred belief probabilities H given a particular causal hypothesis G and θ. The original interaction between parent(s) $X_\pi$ and child $X_{chd}$ nodes in D can be described by an arbitrary function $X_{chd}=\mu(X_\pi)$ plus some observation noise. Depending on the nature of the causal relationships to be modeled, μ( ) can take various forms, including linear, non-linear, monotonic, non-monotonic, concave, convex, step and periodic functions. In the biological domain, a direct causal interaction between two proteins or between a protein and DNA molecule often take the form of a hill function, a step function, or a more general non-monotonic, nonlinear function.

One way to derive the belief inference given in Equation 4 is to represent the relationship between the parent and child nodes as a cubic spline, which can well approximate general nonlinear relationships. However, a more straightforward alternative to splines is to regress the marginal belief of $X_{chd}$ onto $X_\pi$ assuming a linear relationship. If the range of the parent nodes is subdivided into L segments based upon the behavior expected in a causal relationship between two nodes, linear regressions can be carried out in each segment, providing an overall good alternative to spline fitting. See for example, Hastie et al., 2009, *The Elements of Statistical Learning: Data Mining, Inference, and Prediction*, Second Edition, Springer, which is hereby incorporated herein by reference, for disclosure on such statistical techniques.

In the case of $|\pi|=1$, the exemplary approach is to regress onto a single variable whose range has been divided into L segments, whereas when $|\pi|>1$ regression onto multiple variables divided into a $|\pi|$-dimensional grid comprised of $L^{|\pi|}$ components is performed. For the sake of ease of understanding in this exemplary illustration of the disclosed systems and methods, causality between equivalent class structures in which $|\pi|=1$ is inferred are examined, but it will be appreciated that the approach easily extends to the more general case ($|\pi|>1$).

To derive a procedure for fitting the belief inference equation to the data in a piecewise fashion, $\vec{X}$ denotes a vector of predictor(s)/parent node(s) (in this pair-wise causality setting $\vec{X}$ represents just a single variable for any given Markov equivalent structure being considered) and Y represents the response (child) variables. $D \in \mathbb{R}^n$ represents the original noisy observed data and $D_0^l \in [0,1]^n$ denotes the rescaled observed data in the $l^{th}$ segment/grid element, which is comprised of the observed values over the parent and child nodes in the given segment/grid element, i.e. $D_0^l = \{D_{\vec{X}}^l, D_Y^l\}$. Similarly, the predicted data in the $l^{th}$ segment is given by $H^l = \{H_{\vec{X}}^l, H_Y^l\}$.

Given the above, a total of K bins that are evenly distributed in [0,1], $l^k=[k/K, (k+1)/K]$, $k=[0, K-1]$ is pre-defined, and for each bin the number of occurrences of the inferred marginal probability of Y falling in each of the l segments is counted. To avoid dividing zero in calculation of KL-divergence, each bin is pre-added with a small value of pseudo count, e.g. 0.01. For example, $H_Y^l$ falls in the $k^{th}$ bin $I^k \in [0,1]$. The number of occurrences for the $k^{th}$ bin and the $l^h$ segment/grid element is denoted by $M_k^l$. The counterpart of this number in $D_Y^l$, with respect to the observed data, is $N_k^l$. The frequency for the predicted data is then calculated as $p_k^l = M_k^l / \Sigma_k M_k^l$ for the inferred belief probability $H_Y^l$ and similarly $q_k^l = N_k^l / \Sigma_k N_k^l$ for the observed data $D_Y^l$, where:
- $H_Y^l$=the inferred belief probability for the response (child) variable Y (given a particular causal hypothesis G and θ), in segment/grid element l,
- $p_k^l$=the frequency for the predicted data in the $k^{th}$ bin and the $l^{th}$ segment,
- $M_k^l$=the number of occurrences of the inferred marginal probability of Y falling into the $k^{th}$ bin and the $l^{th}$ segment,
- $D_Y^l$=the rescaled observed data in the $l^{th}$ segment/grid element for response (child) variable Y,
- $q_k^l$=the frequency for the observed data in the $k^{th}$ bin and the $l^{th}$ segment, and
- $N_k^l$=the number of occurrences of the observed data for Y falling into the $k^{th}$ bin and the $l^{th}$ segment.

These counts and frequencies are used to compute the KL-divergence kernel, maximize the likelihood score, and identify the maximum linear regression model $\hat{\theta}$ in Equation 1 per segment as described below. To maximize the data likelihood function $P(D|G, \hat{\theta})$ in Equation 1 in each segment, what is identified is the parameter $\hat{\theta}$ that minimizes the KL-divergence for the current causal hypothesis G, which is defined as the symmetrized KL-divergence between the predicted belief and the rescaled observed data for every segment:

$$\hat{\theta}^l = \underset{\theta}{\mathrm{argmax}}\{P(D_0^l | G, \theta) P(\theta | G)\} \propto \quad (6)$$

$$\underset{\theta}{\mathrm{argmax}}\{P(D_Y^l | P(Y | E = D_X^l, G, \theta))\} \propto$$

$$\underset{\theta}{\mathrm{argmax}}\{P(k(D_Y^l, H_Y^l(G, \theta)))\} \propto \underset{\theta}{\mathrm{argmax}}\{-\log(k(D_Y^l, H_Y^l(G, \theta)))\} \propto$$

$$\underset{\theta}{\mathrm{argmin}}\left\{\sum_{k=0}^{K} p_k^l \ln(p_k^l / q_k^l) + \sum_{k=0}^{K} q_k^l \ln(q_k^l / p_k^l)\right\}$$

where $P(\theta|G)=1/M$ for θ sampled uniformly in [0,1]. The statistical counts of the predicted probability, $p_k^l$ for $l^{th}$ segment in the $k^{th}$ bin, is a function of G and θ. The optimal statistical count of the fitted model for the $l^{th}$ segment and $k^{th}$ bin is $\hat{M}_k^l$. The overall fitted linear regression model (G, $\hat{\theta}^l | l=1, \ldots, L$)) with the counts across all segments in the $k^{th}$ bin of [0,1] is obtained by summing $\hat{M}_k^l$ over the total L segments, i.e. $\hat{M}_k = \Sigma_{l=1}^L \hat{M}_k^l$. According to Equation 1 and Equation 3, the final optimized estimation of the data likelihood is then equal to $$P(D | G, \hat{\theta}) \propto -\log\left[\left(1 - \exp\left(\frac{\sum_{k=0}^{K} \hat{p}_k \ln(\hat{p}_k / q_k) + \sum_{k=0}^{K} q_k \ln(q_k / \hat{p}_k)}{2}\right)\right)\right] \quad (7)$$

where,
- $\hat{p}_k$=the frequency for the predicted probability in the $k^{th}$ bin, calculated as $\hat{p}_k = \hat{M}_k / \Sigma_{i=0}^K \hat{M}_i$, and
- $q_k$=the frequency for the observed data in the $k^{th}$ bin.

For simplicity, an example is shown below in which the L segments in [0,1] are obtained simply dividing the range of each parent node evenly into L segments.

One advantage of the disclosed systems and methods is that it enables causal inference in a more complex network setting compared to previous methods that are limited to assessing pairwise causal relationships. This generality is achieved by leveraging the marginal probabilistic inference in a Bayesian network setting. This advantage has significant importance given conventional top-down Bayesian network approaches can be systematically combined with the disclosed causal inference approach to form an integrated learning-inference framework. That is, the disclosed approach can enable a unified bottom-up and top-down modeling approach. The disclosed systems and methods infer causality by maximizing the data likelihood based on a symmetrized KL-divergence measure between predicted and observed probabilities, implemented using a piece-wise linear regression framework. Accordingly, optimizing the selection of the segment size and number is necessary to achieve maximal power and accuracy. Further, the examples provided herein assumed that the interaction function representing the type of relationship that exists between the nodes of interest was known. However, the interaction functions types will not always be known a priori.

One aspect of present disclosure provides an integration of the disclosed approach with a conventional structure-based learning approach, e.g. Bayesian network, in order to provide a very flexible framework that can model biological systems in a more comprehensive and accurate fashion, thereby incorporating the disclosed bottom up modeling in a top-down framework to maximally leverage not only existing data, but knowledge derived from such data.

Figure 48A:
FIGS. 48a-48c provide a flowchart of a process for perturbing a system according to some implementations.
Figure 48B:
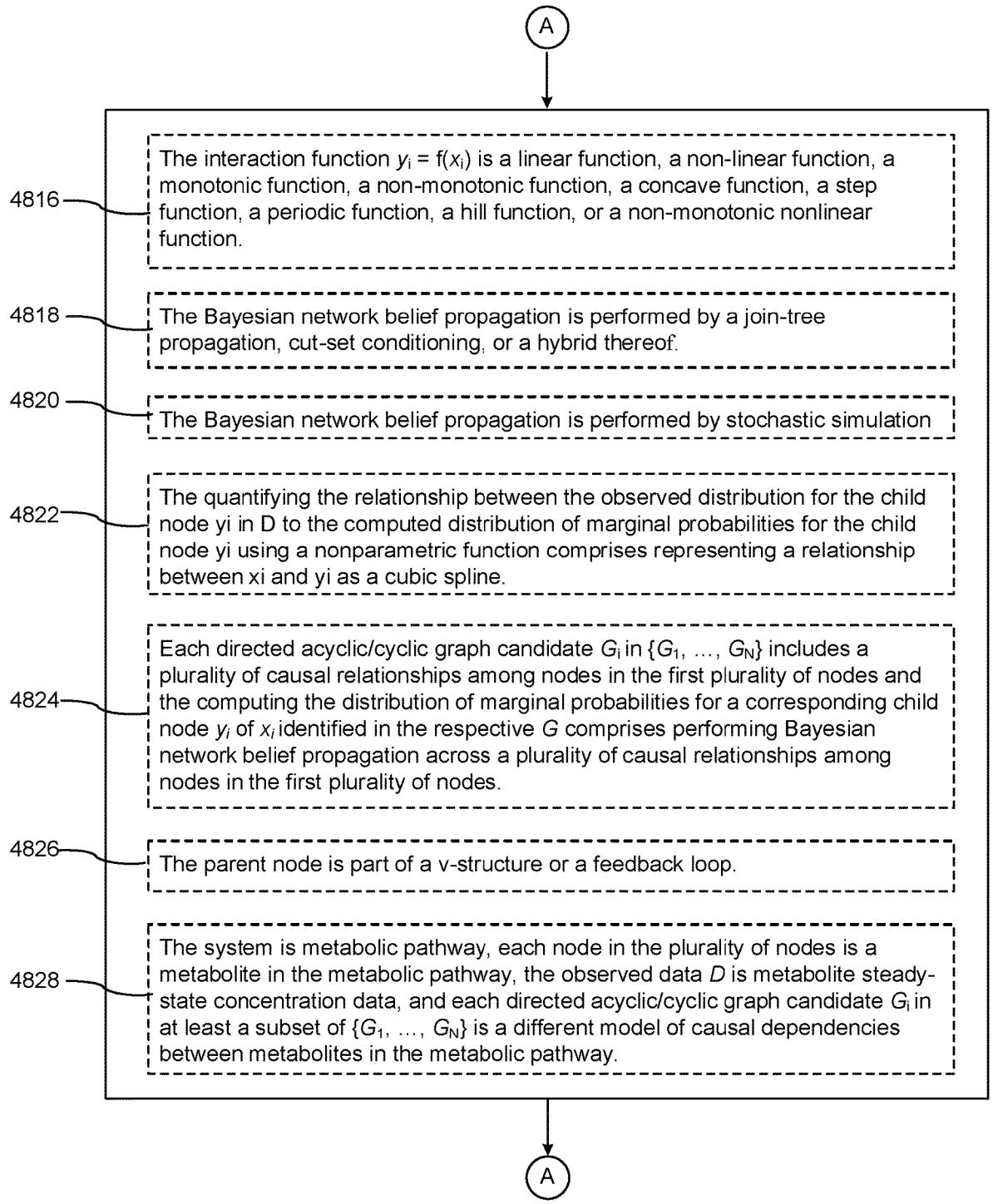
Figure 48C:
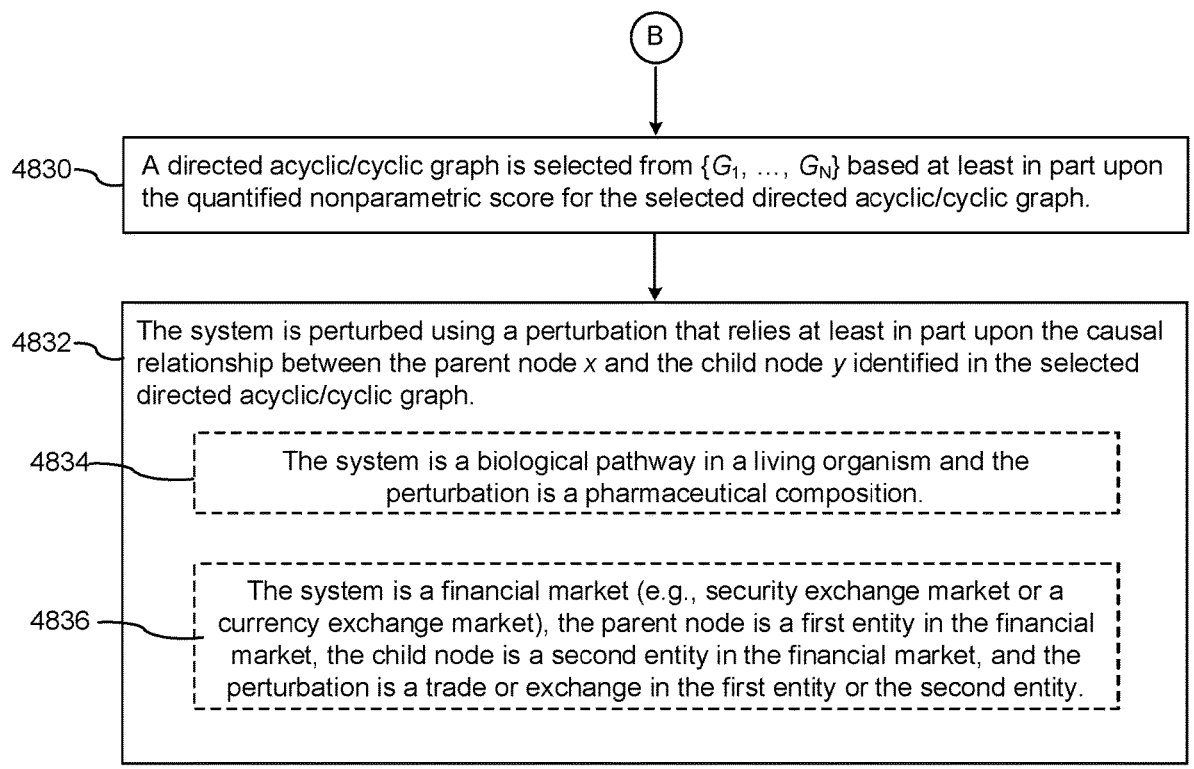

FIGS. 48a-c provide a flowchart of a process 4800, performed by a computing device (e.g., using causal connection computation module 50 of FIG. 2), for perturbing a system (4802). In some embodiments, the method is performed at a computing device 10 (FIG. 2) having one or more processors and memory. The memory stores one or more programs configured for execution by the one or more processors (4804). A set of directed acyclic/cyclic graph candidates $\{G_1, \ldots, G_N\}$ is obtained for the system, where N is a positive integer greater than 1, and each respective directed acyclic/cyclic graph candidate $G_i$ in at least a subset of $\{G_1, \ldots, G_N\}$ includes one or more causal relationships among nodes in a first plurality of nodes, where each causal relationship includes a parent node that is causal for a child node, and wherein two or more nodes in each respective directed acyclic/cyclic graph candidate Gi in at least a subset of $\{G_1, \ldots, G_N\}$ are Markov equivalent, a parent node $x_i$ of a first $G_i$ in $\{G_1, \ldots, G_N\}$ is different than a parent node $x_j$ of a second $G_j$ in $\{G_1, \ldots, G_N\}$ (4806). In some embodiments N is giver or greater (4808).

Observed data D is obtained for the first plurality of nodes (4810). In some embodiments, each node in the plurality of nodes is a cellular constituent (e.g., nucleic acid, a ribonucleic acid, a protein, or a metabolite) in a plurality of cellular constituents, and the observed data is cellular constituent abundance data (4812).

For each respective $G_i$ in at least the subset of $\{G_1, \ldots, G_N\}$, the marginal probability of a parent node $x_i$ identified in the respective $G_i$ is clamped based upon the observed data D. A distribution of marginal probabilities is computed for a corresponding child node $y_i$ of $x_i$ identified in the respective $G_i$, wherein the computation is performed by Bayesian network belief propagation using an interaction function of the form $y_i=f(x_i)$. Furthermore, the relationship between the observed distribution for the child node $y_i$ in D to the computed distribution of marginal probabilities for the child node $y_i$ is quantified using a nonparametric function, thereby obtaining a nonparametric score for the respective $G_i$ (4814). In some embodiments, the nonparametric function is an f-divergence function (4815). In some embodiments, the interaction function $y_i=f(x_i)$ is a linear function, a non-linear function, a monotonic function, a non-monotonic function, a concave function, a step function, a periodic function, a hill function, or a non-monotonic nonlinear function (4816). In some embodiments, the Bayesian network belief propagation is performed by a join-tree propagation, cut-set conditioning, or a hybrid thereof (4818). In some embodiments, the Bayesian network belief propagation is performed by stochastic simulation (4820). In some embodiments, the quantifying the relationship between the observed distribution for the child node $y_i$ in D to the computed distribution of marginal probabilities for the child node $y_i$ using a nonparametric function comprises representing a relationship between $x_i$ and $y_i$ as a cubic spline (4822). In some embodiments, each directed acyclic/cyclic graph candidate $G_i$ in $\{G_1, \ldots, G_N\}$ includes a plurality of causal relationships among nodes in the first plurality of nodes and the computing the distribution of marginal probabilities for a corresponding child node $y_i$ of $x_i$ identified in the respective G comprises performing Bayesian network belief propagation across a plurality of causal relationships among nodes in the first plurality of nodes (4824). In some embodiments, the parent node is part of a v-structure or a feedback loop (4826). In some embodiments, the system is metabolic pathway, each node in the plurality of nodes is a metabolite in the metabolic pathway, the observed data D is metabolite steady-state concentration data, and each directed acyclic/cyclic graph candidate $G_i$ in at least a subset of $\{G_1, \ldots, G_N\}$ is a different model of causal dependencies between metabolites in the metabolic pathway (4828).

A directed acyclic/cyclic graph is selected from $\{G_1, \ldots, G_N\}$ based at least in part upon the quantified nonparametric score for the selected directed acyclic/cyclic graph (4830). The system is perturbed using a perturbation that relies at least in part upon the causal relationship between the parent node x and the child node y identified in the selected directed acyclic/cyclic graph (4832). In some embodiments, the system is a biological pathway in a living organism and the perturbation is a pharmaceutical composition (4834). In some embodiments, the system is a financial market, the parent node is a first entity in the financial market, the child node is a second entity in the financial market, and the perturbation is a trade or exchange in the first entity or the second entity (4836). In some embodiments, the system is any system that can be subjected to Bayesian analysis, including, but not limited to, actuarial models, economic models, power plant efficiency models, information network models, and weather models.

Example 1—Examination of a Pair of Markov Equivalent Variables

Figure 2:
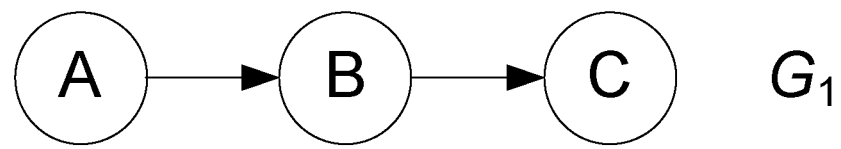
FIG. 2 illustrates the ground truth for three equivalent structures.
Figure 2:
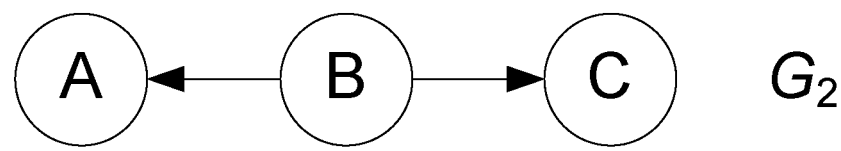
Figure 2:
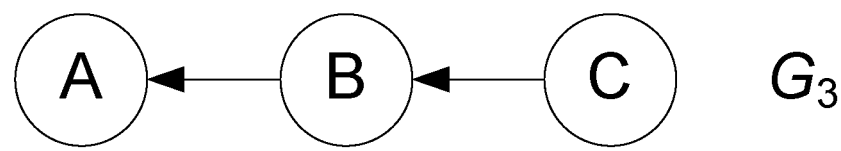

To illustrate the disclosed causal inference procedure, it is applied to a pair of variables. To begin, synthetic data is generated given true pair-wise relationships as depicted in FIG. 2. It is assumed that the observed data for the parent nodes is drawn from a uniform distribution and a hill function is used to describe the common interactions between the parent and child nodes. Gaussian noise is added to the synthetic data to model uncertainty inherent in measurement data, and without loss of generality L is set to 4. In practice some care is needed in the selection of L, since if L is set too high, the power of the likelihood score to distinguish the true causal direction from the null hypothesis can be significantly decreased. On the other hand, if L is set too low, the likelihood score returned from both the true and null causal models will not achieve statistical significance.

Figure 3:
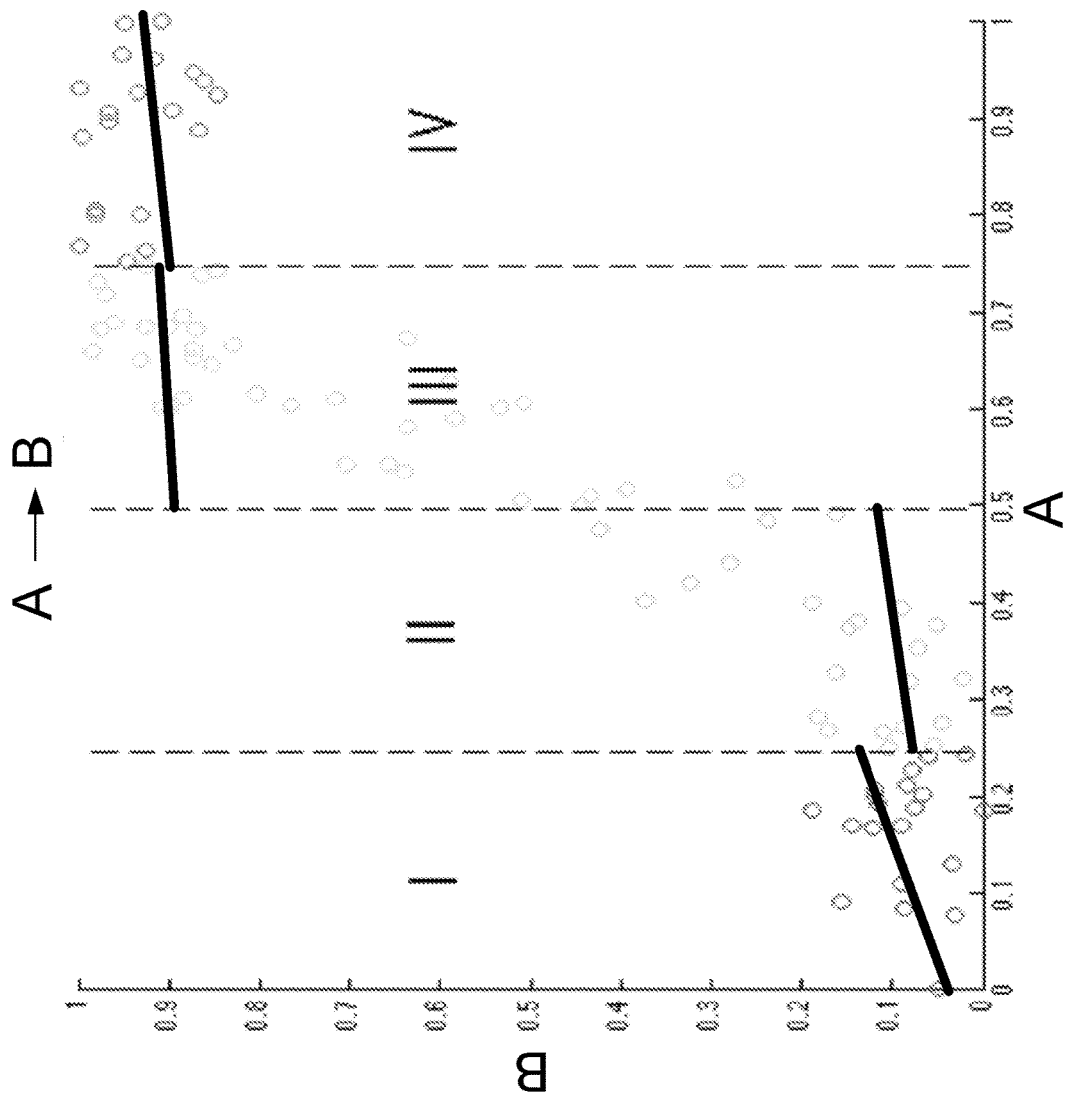
FIG. 3 shows the fit of a piece-wise linear regression model in the true (A→B) causal direction, in accordance with an embodiment of the present disclosure.
Figure 4:
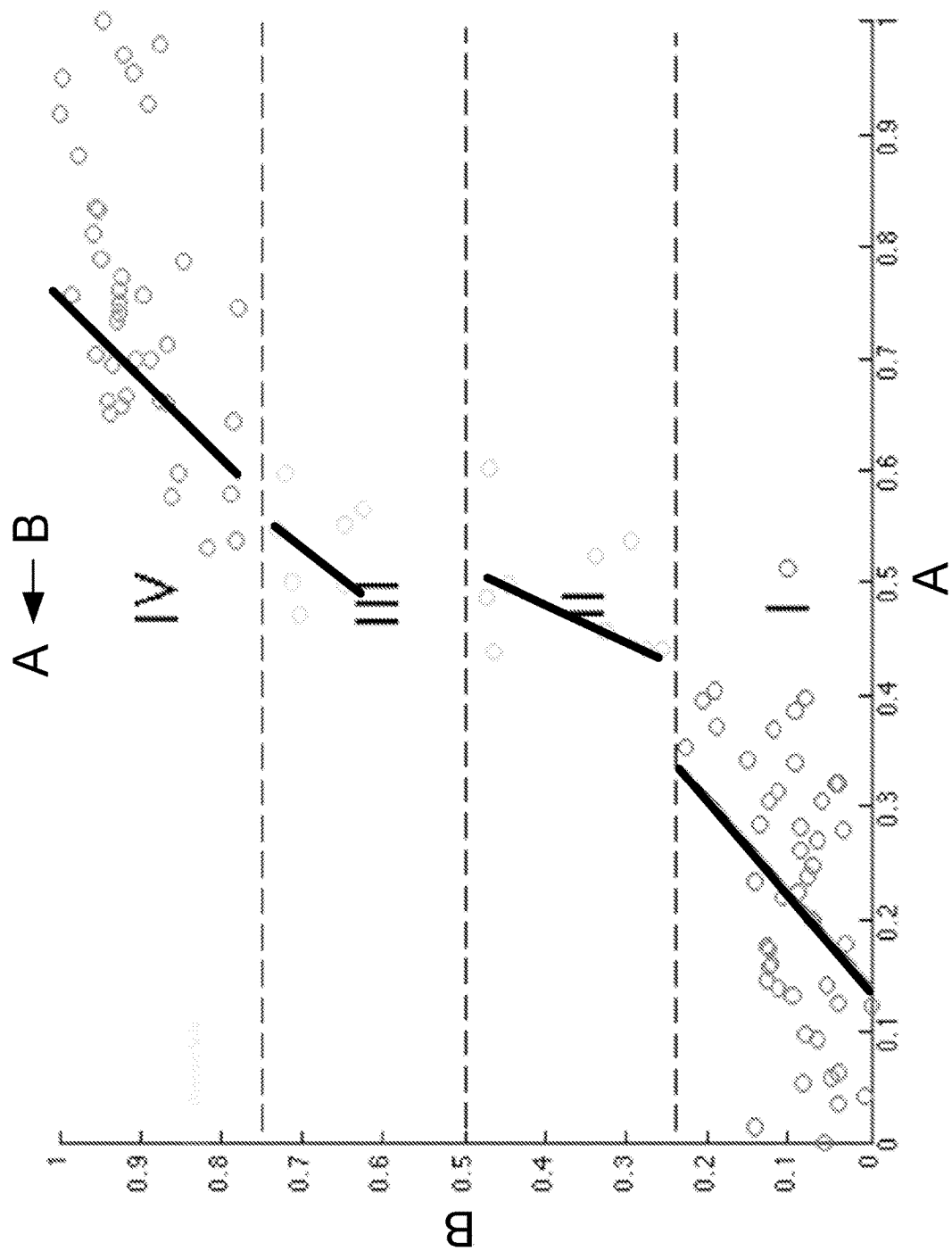
FIG. 4 shows the fit of the piece-wise linear regression model in the false (A←B) causal direction in accordance with an embodiment of the present disclosure.
Figure 5:
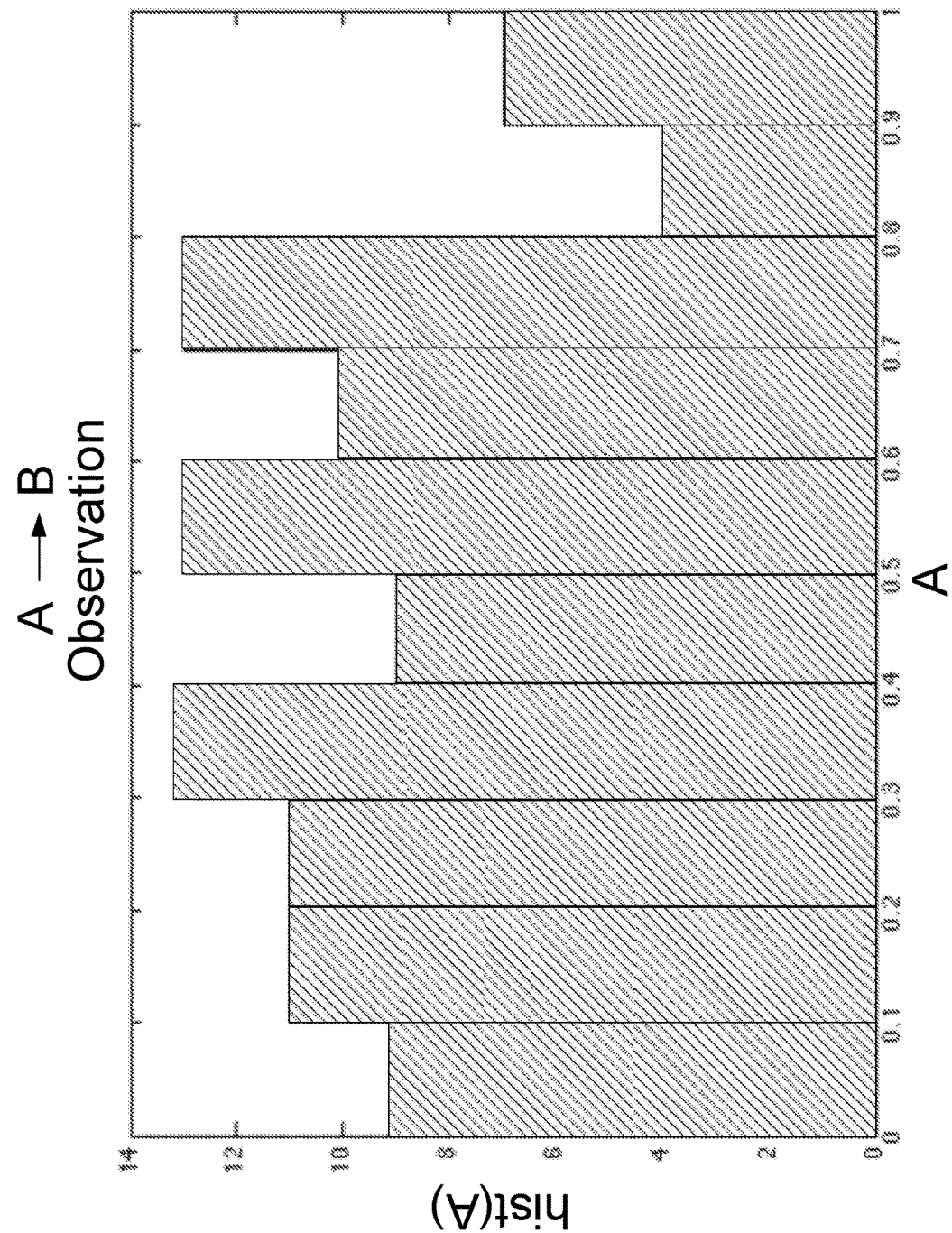
FIG. 5 illustrates the distribution of the predictor variable (parent node) in the case where A is assumed to be the predictor variable, corresponding to FIG. 3, in accordance with an embodiment of the present disclosure.
Figure 6:
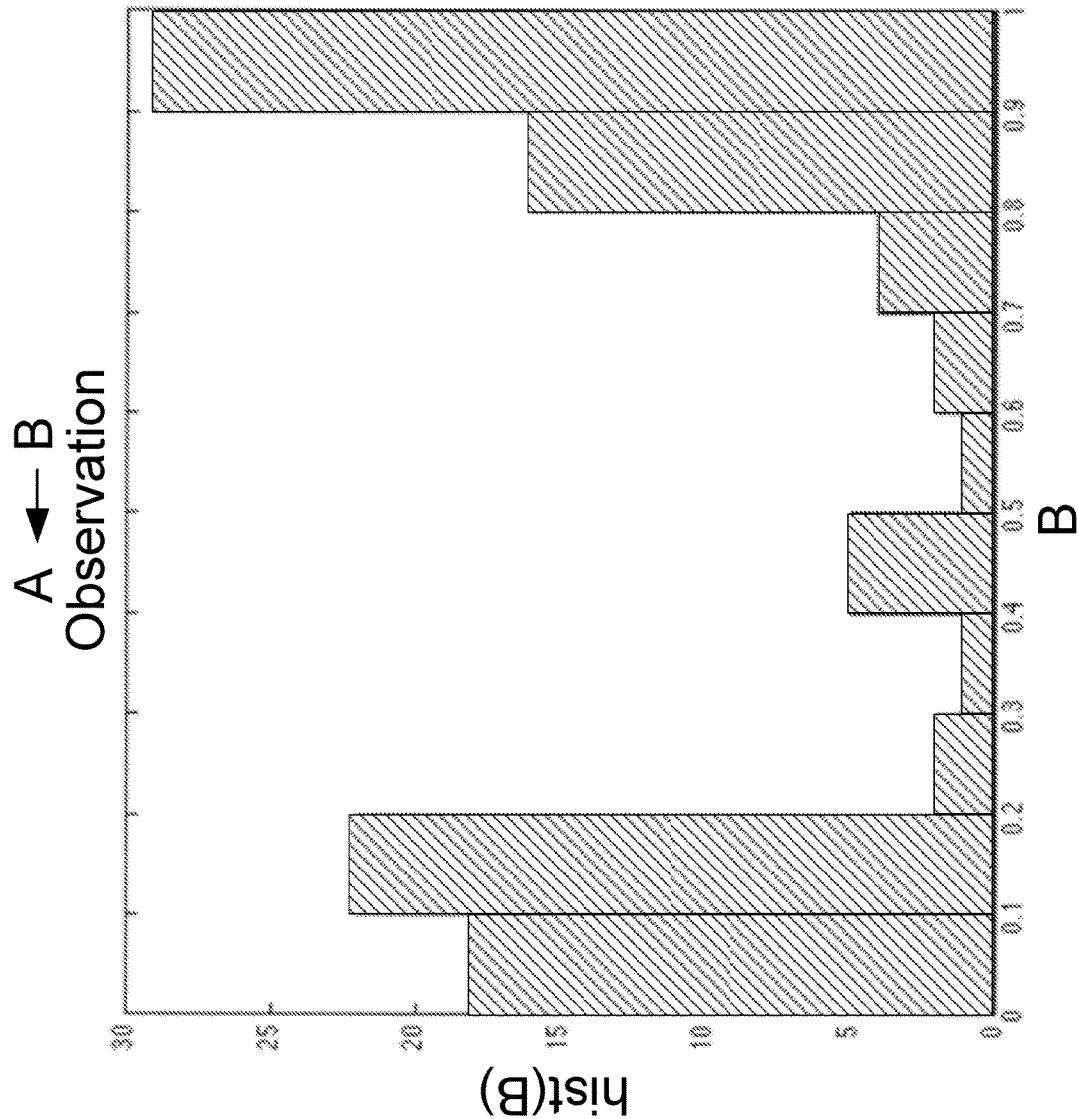
FIG. 6 illustrates the distribution of the predictor variable (parent node) in the case where B is assumed to be the predictor variable, corresponding to FIG. 4, is shown in FIG. 6.
Figure 7:
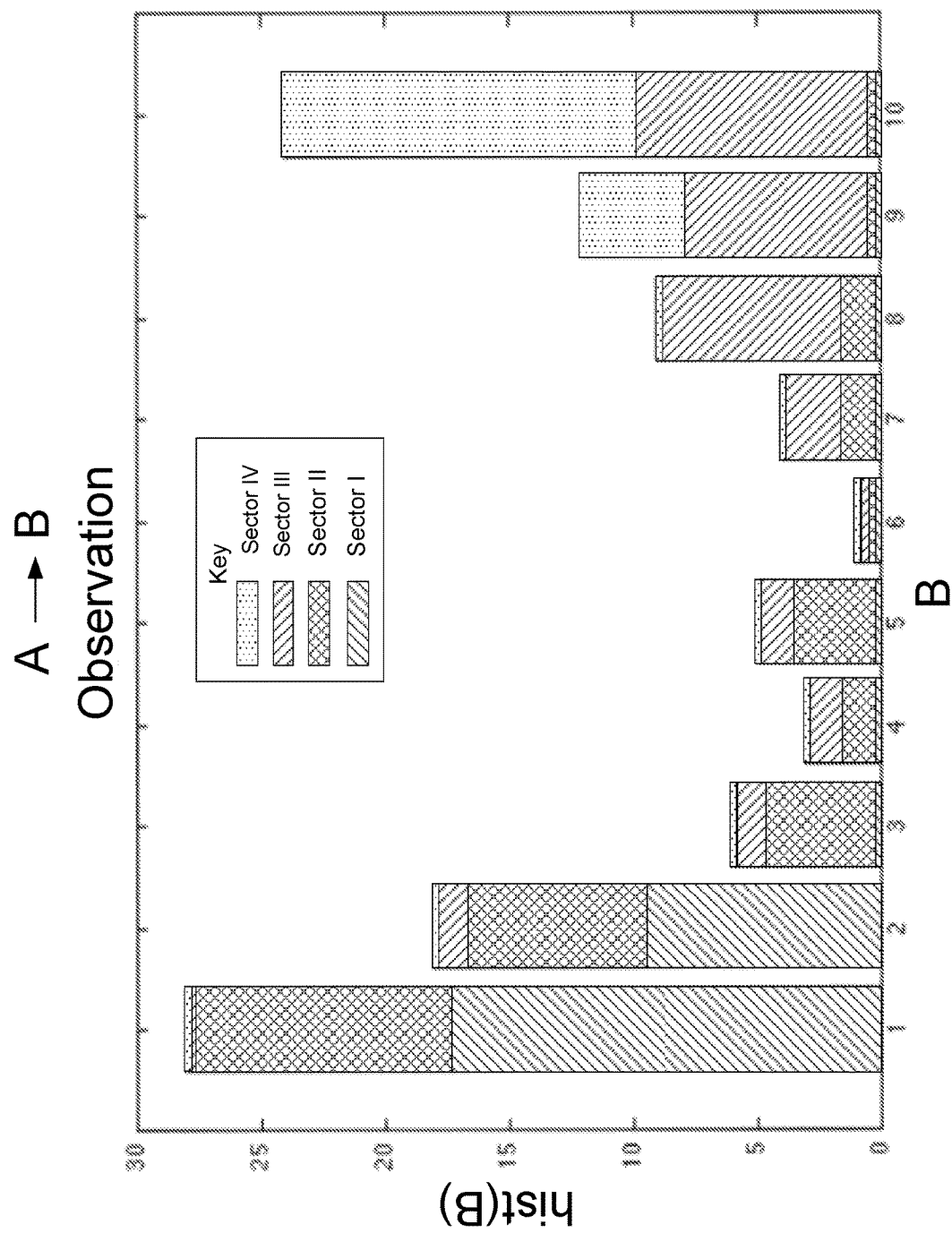
FIG. 7 illustrates the observed distribution of the response variable (child node), where A is the parent of the child node B in accordance with an embodiment of the present disclosure.
Figure 8:
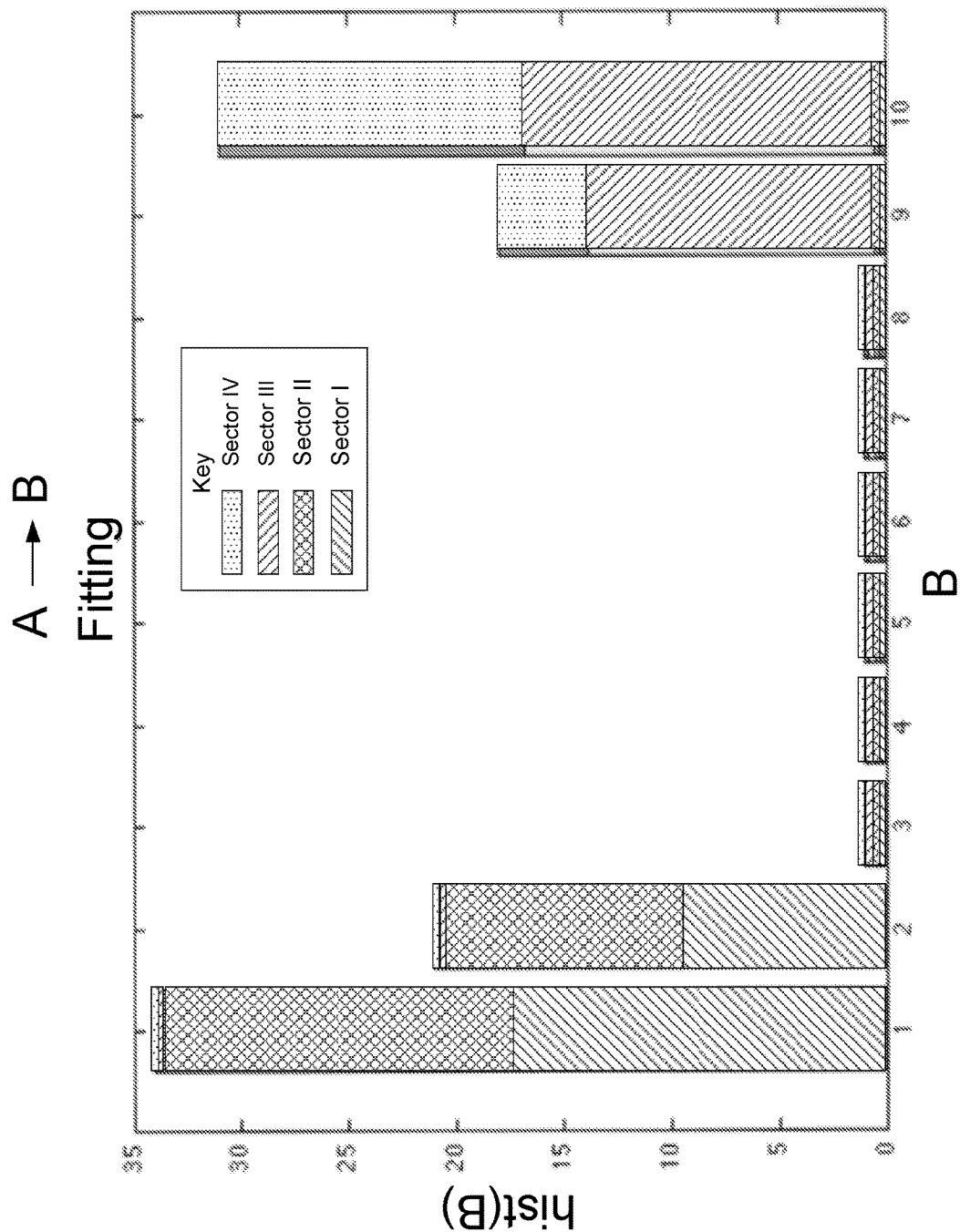
FIG. 8 illustrates the calculated distribution of the response variable (child node), where (i) A is the parent and is clamped according to the observed distribution of A and (ii) the distribution of the child node B is calculated, in accordance with an embodiment of the present disclosure.
Figure 9:
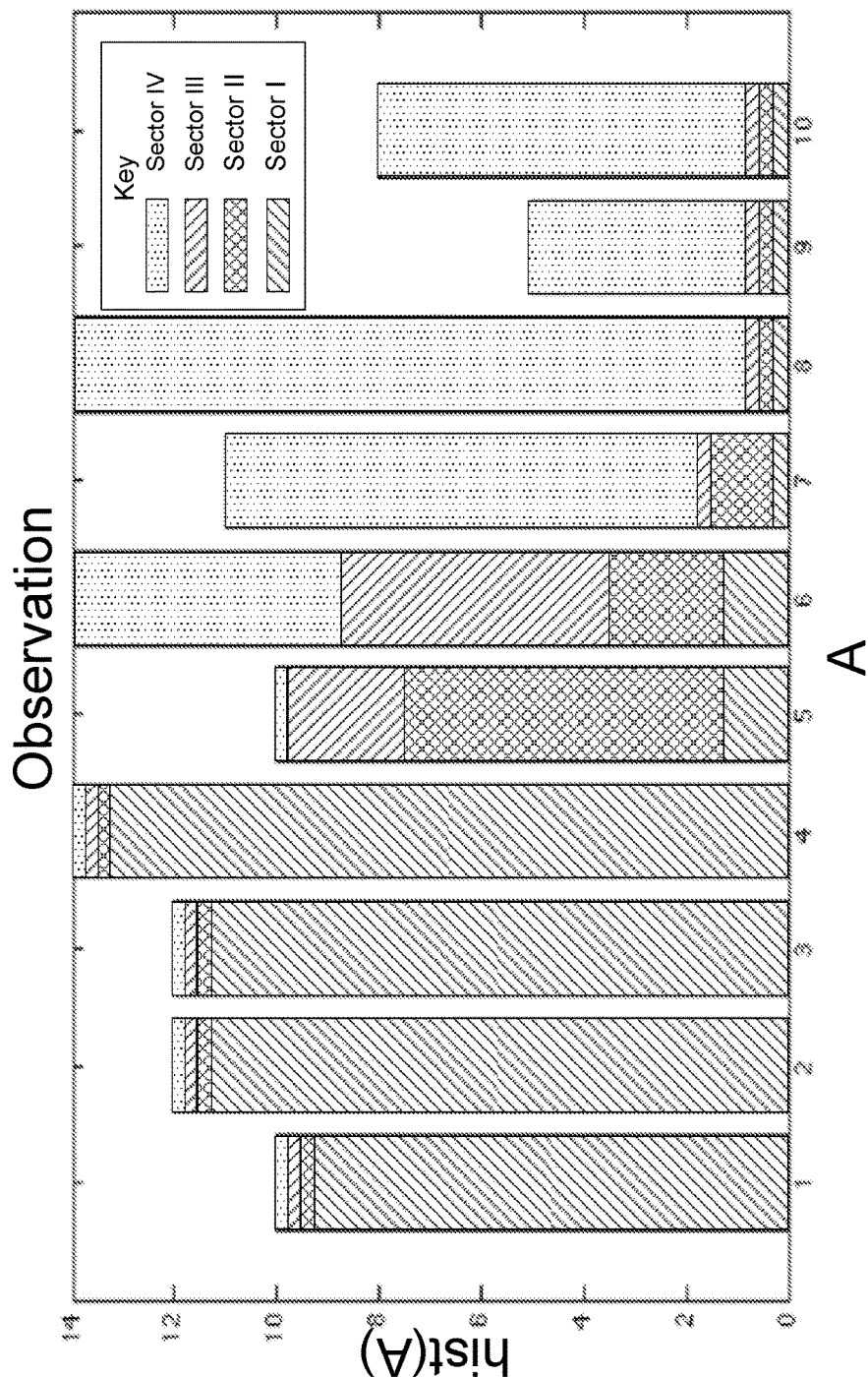
FIG. 9 illustrates the observed distribution of the response variable (child node), where B is the parent of the child node A in accordance with an embodiment of the present disclosure.
Figure 10:
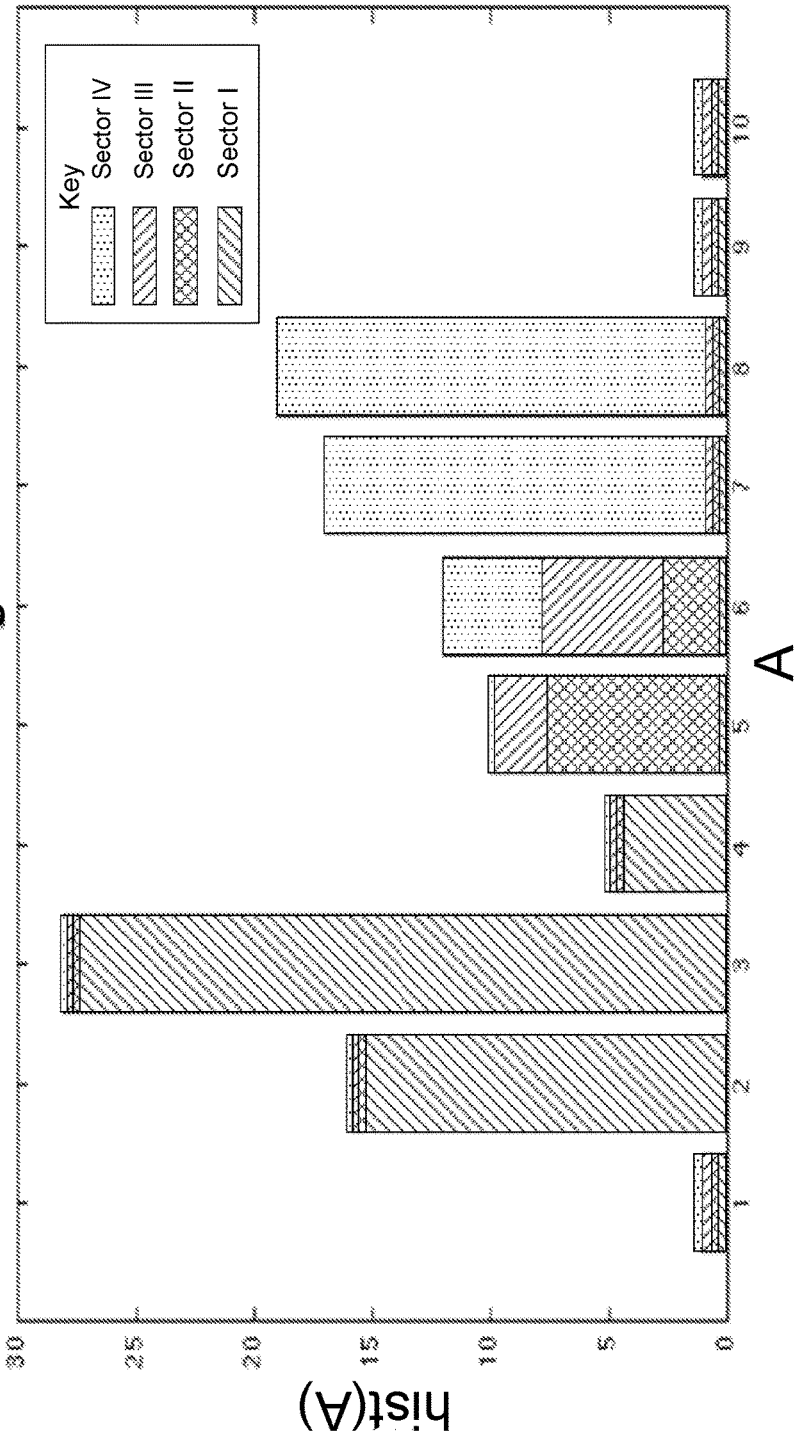
FIG. 10 illustrates the calculated distribution of the response variable (child node), where (i) B is the parent and is clamped according to the observed distribution of B and (ii) the distribution of the child node A is calculated, in accordance with an embodiment of the present disclosure.
Figure 11:
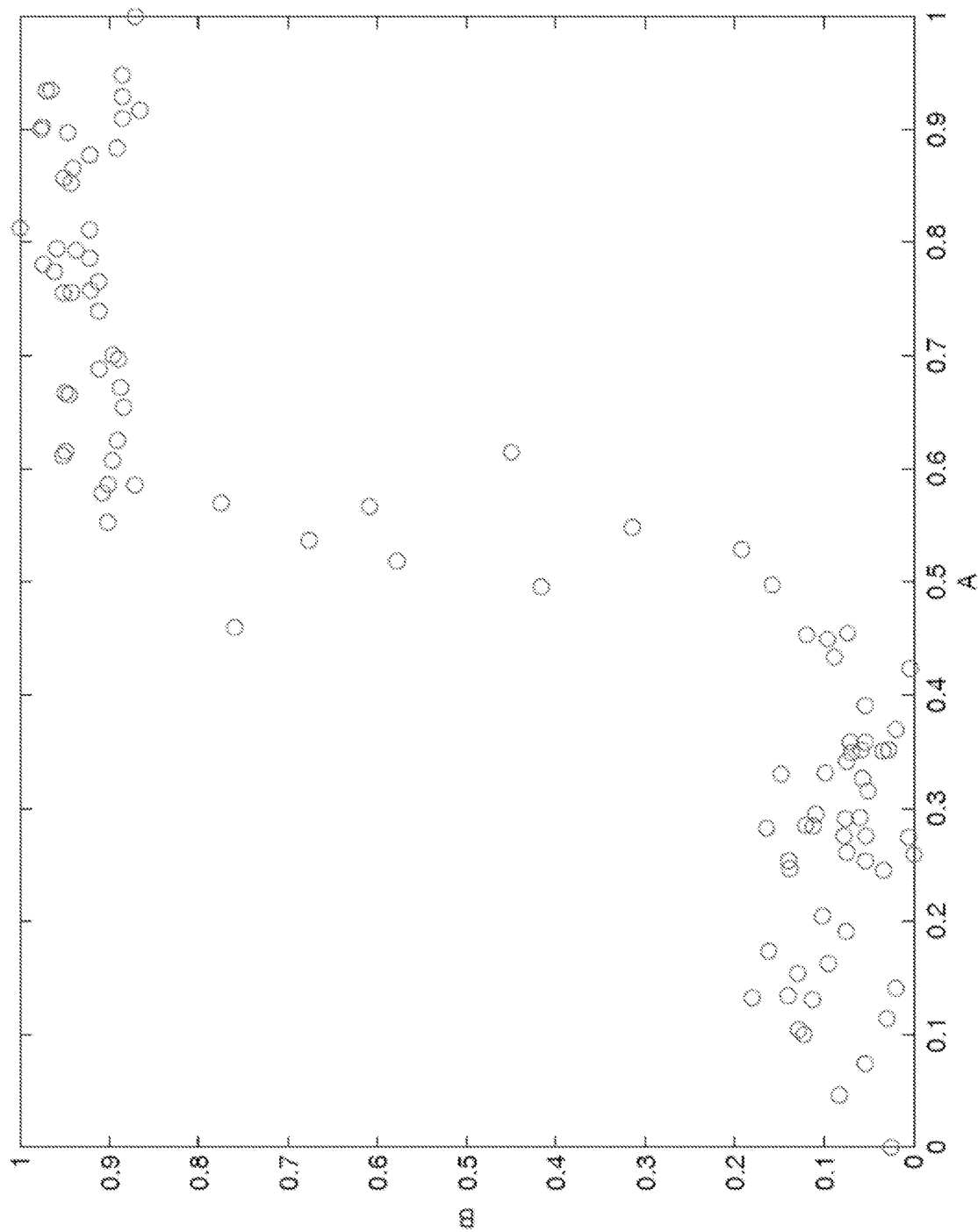
FIG. 11 depicts (A vs. B) synthetic data (rescaled to [0,1]) with low noise, where the parent node A is sampled from a uniform distribution, and values of B are generated in accordance with the interaction function B=f(A), where f is a hill function, based upon the ground truth structure $G_1$ of FIG. 2, in accordance with an exemplary embodiment.
Figure 12:
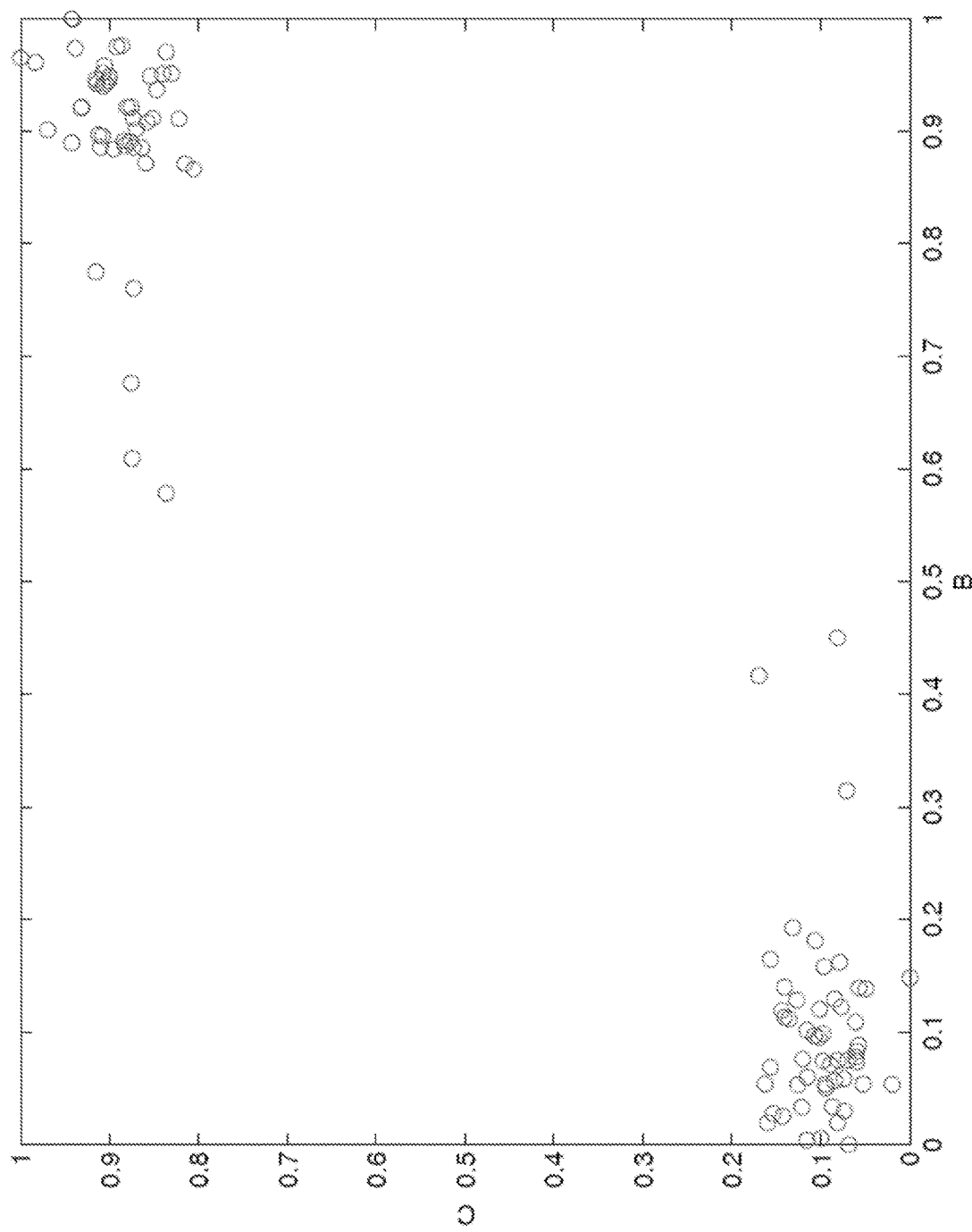
FIG. 12 depicts (B vs. C) synthetic data (rescaled to [0,1]) with low noise, where the values of C are generated in accordance with the interaction function C=g(B) using the values for B from FIG. 11, and where g is a hill function, based upon the ground truth structure $G_1$ of FIG. 2, in accordance with an exemplary embodiment.
Figure 13:
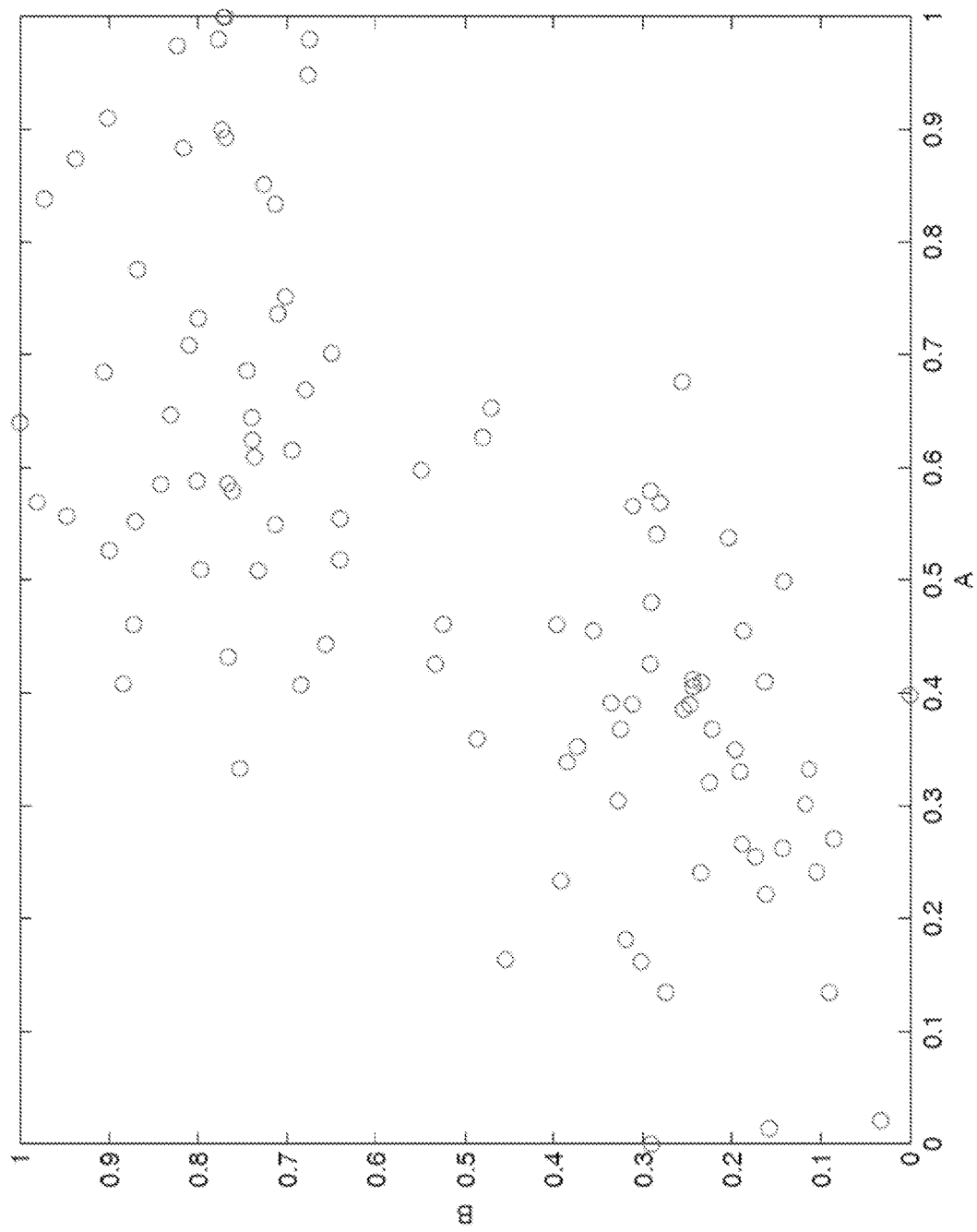
FIG. 13 depicts (A vs. B) synthetic data (rescaled to [0,1]) with high noise, where the parent node A is sampled from a uniform distribution, and values of B are generated in accordance with the interaction function B=f(A), where f is a hill function, based upon the ground truth structure $G_1$ of FIG. 2, in accordance with an exemplary embodiment.
Figure 14:
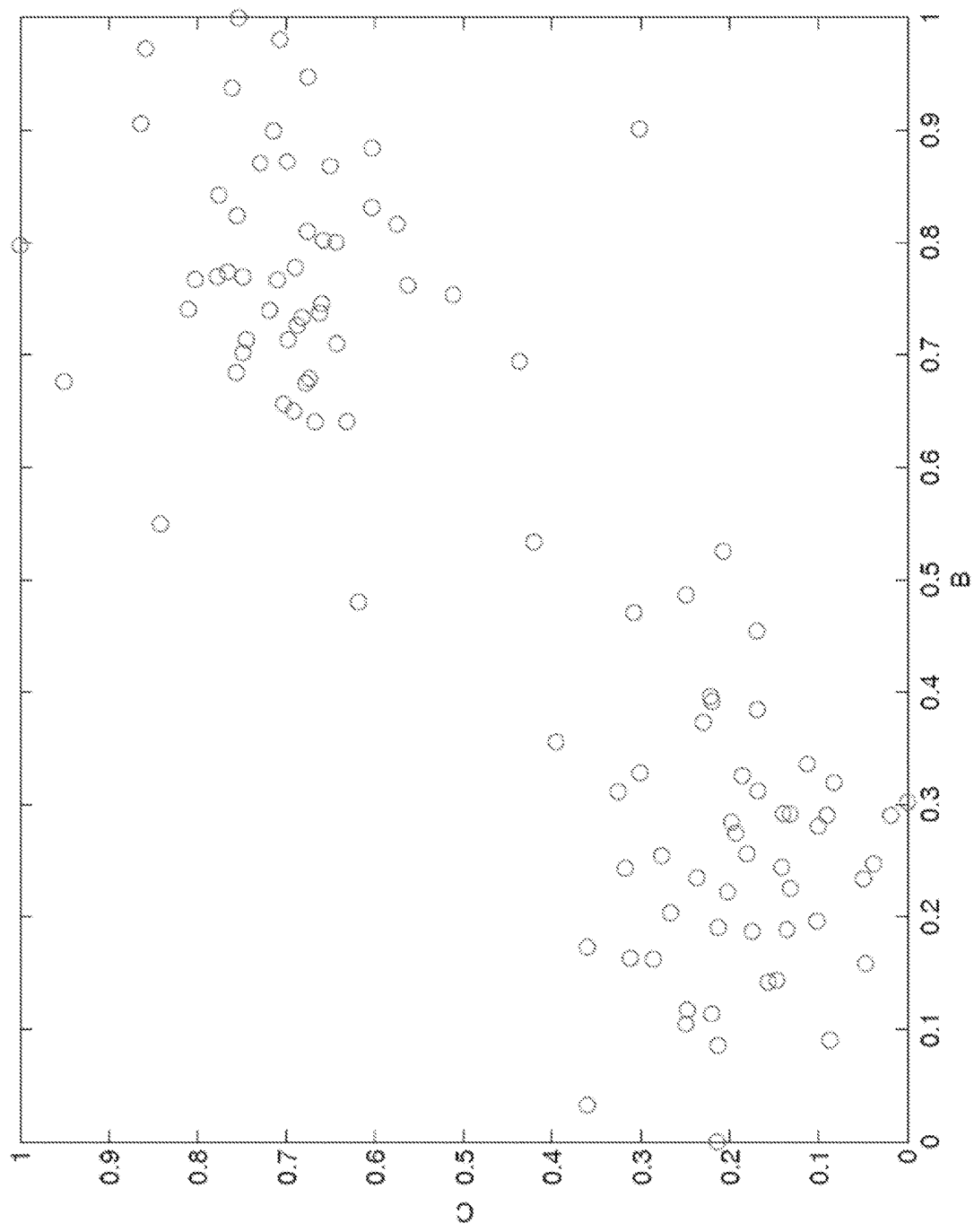
FIG. 14 depicts (B vs. C) synthetic data (rescaled to [0,1]) with high noise, where the values of C are generated in accordance with the interaction function C=g(B) using the values for B from FIG. 13, where g is a hill function, based upon the ground truth structure $G_1$ of FIG. 2, in accordance with an exemplary embodiment.
Figure 15:
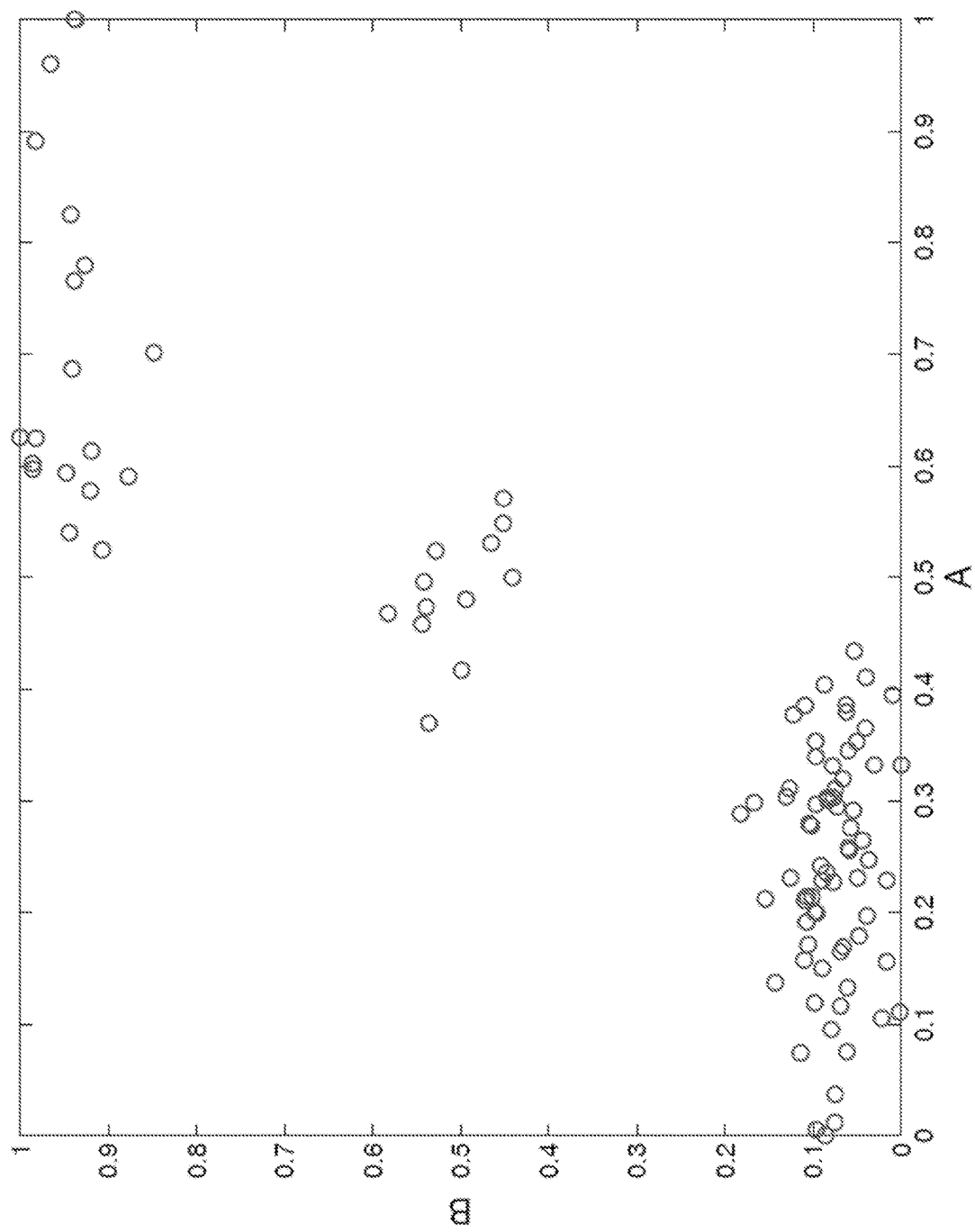
FIG. 15 depicts (A vs. B) synthetic data (rescaled to [0,1]) with low noise, where the parent node A is sampled from a Poisson distribution, and values of B are generated in accordance with the interaction function B=f(A), where f is a hill function, based upon the ground truth structure $G_1$ of FIG. 2, in accordance with an exemplary embodiment.
Figure 16:
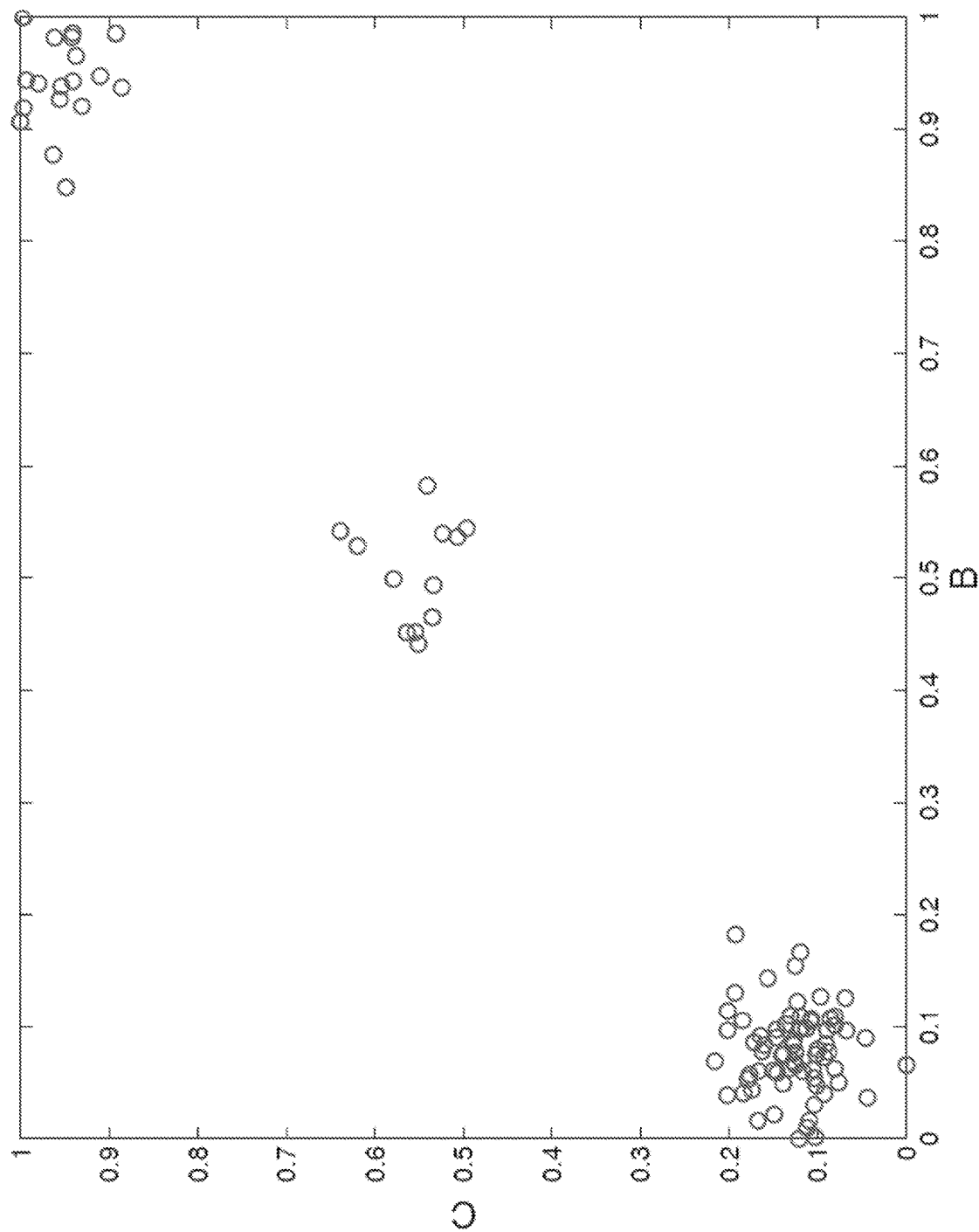
FIG. 16 depicts (B vs. C) synthetic data (rescaled to [0,1]) with low noise, where the values of C are generated in accordance with the interaction function C=g(B) using the values for B from FIG. 15, where g is a hill function, base upon the ground truth structure $G_1$ of FIG. 2, in accordance with an exemplary embodiment.
Figure 17:
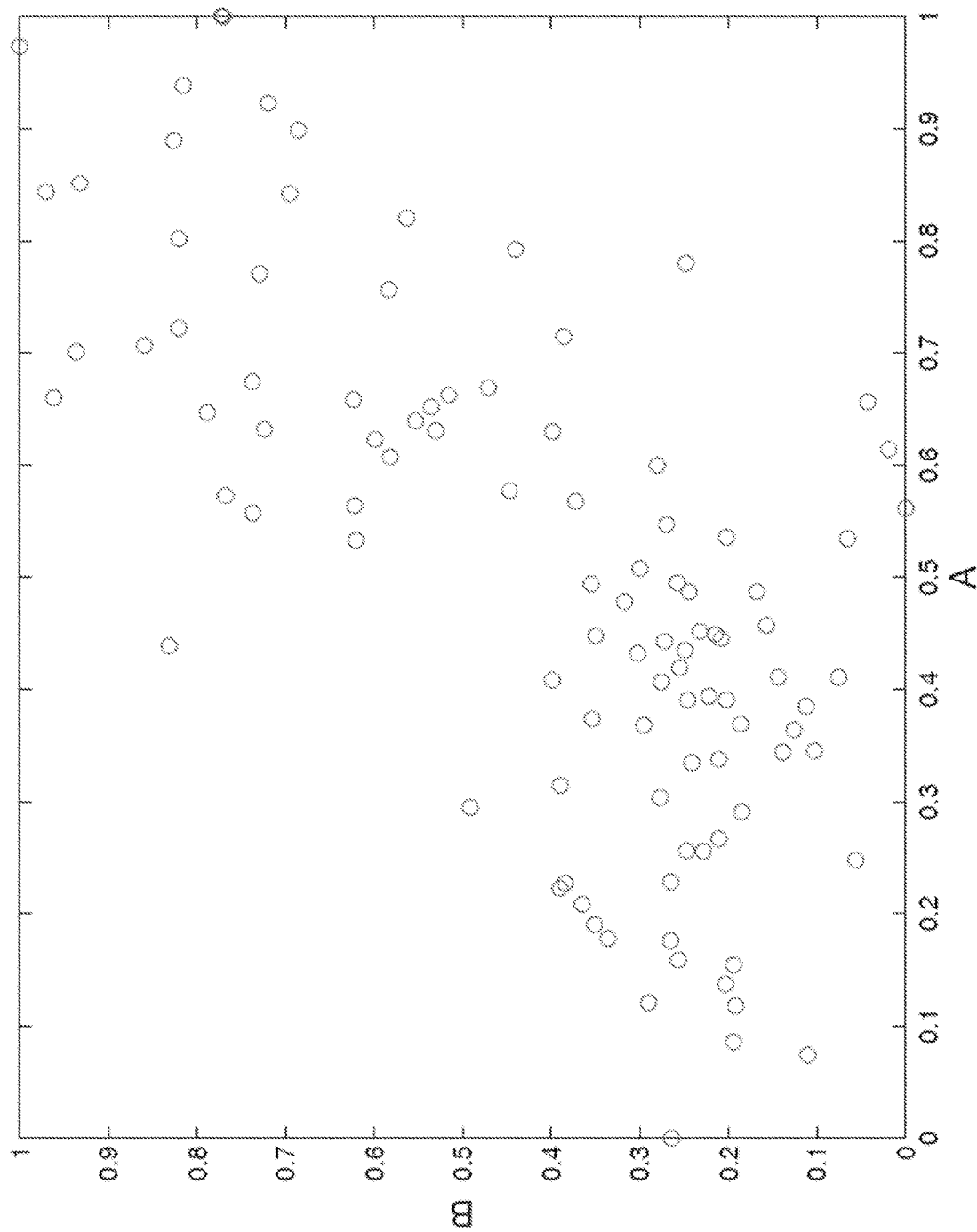
FIG. 17 depicts (A vs. B) synthetic data (rescaled to [0,1]) with high noise, where the parent node A is sampled from a Poisson distribution, and values of B are generated in accordance with the interaction function B=f(A), where f is a hill function, based upon the ground truth structure $G_1$ of FIG. 2, in accordance with an exemplary embodiment.
Figure 18:
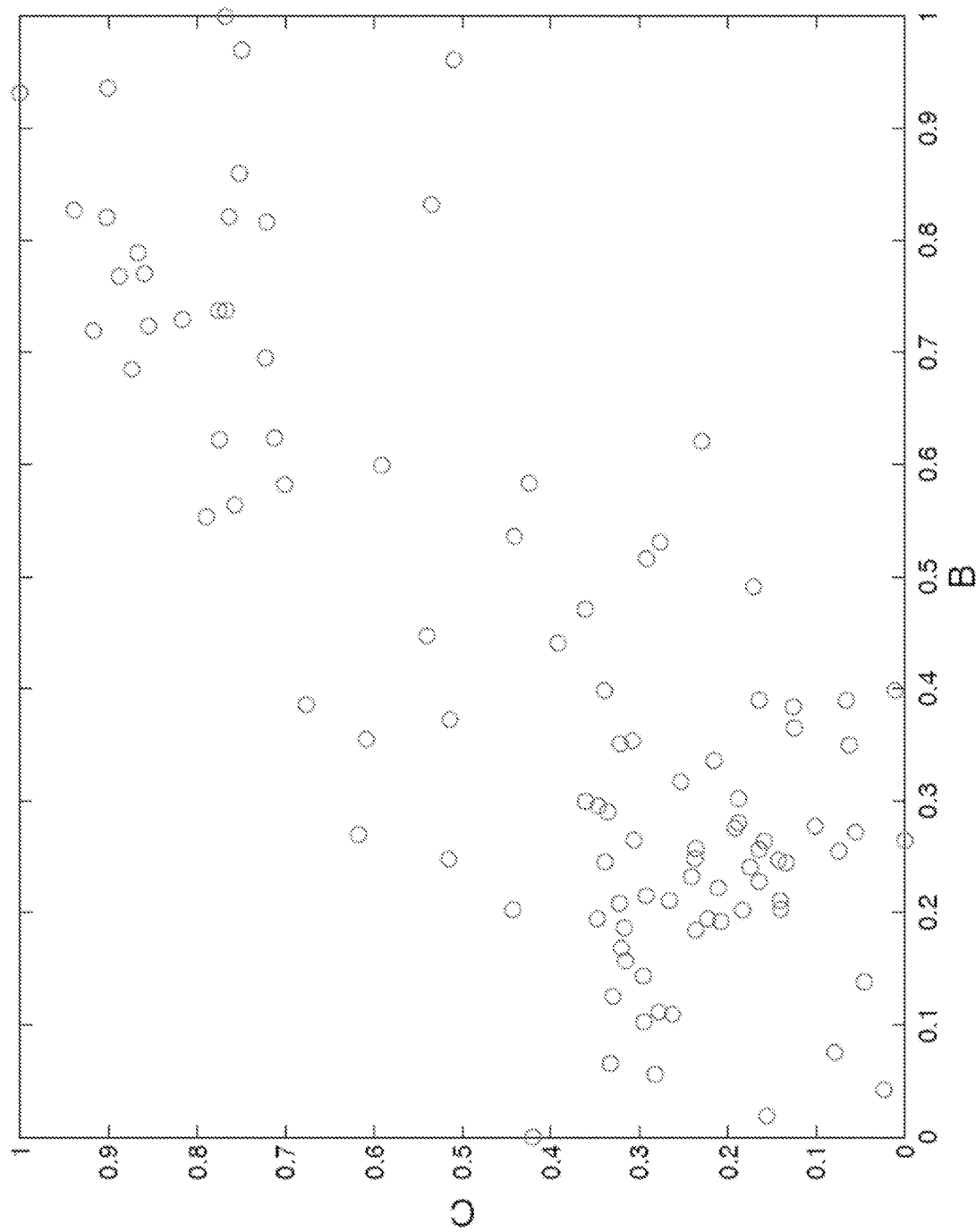
FIG. 18 depicts (B vs. C) synthetic data (rescaled to [0,1]) with high noise, where the values of C are generated in accordance with the interaction function C=g(B) using the values for B from FIG. 17, where g is a hill function, based upon the ground truth structure $G_1$ of FIG. 2, in accordance with an exemplary embodiment.
Figure 19:
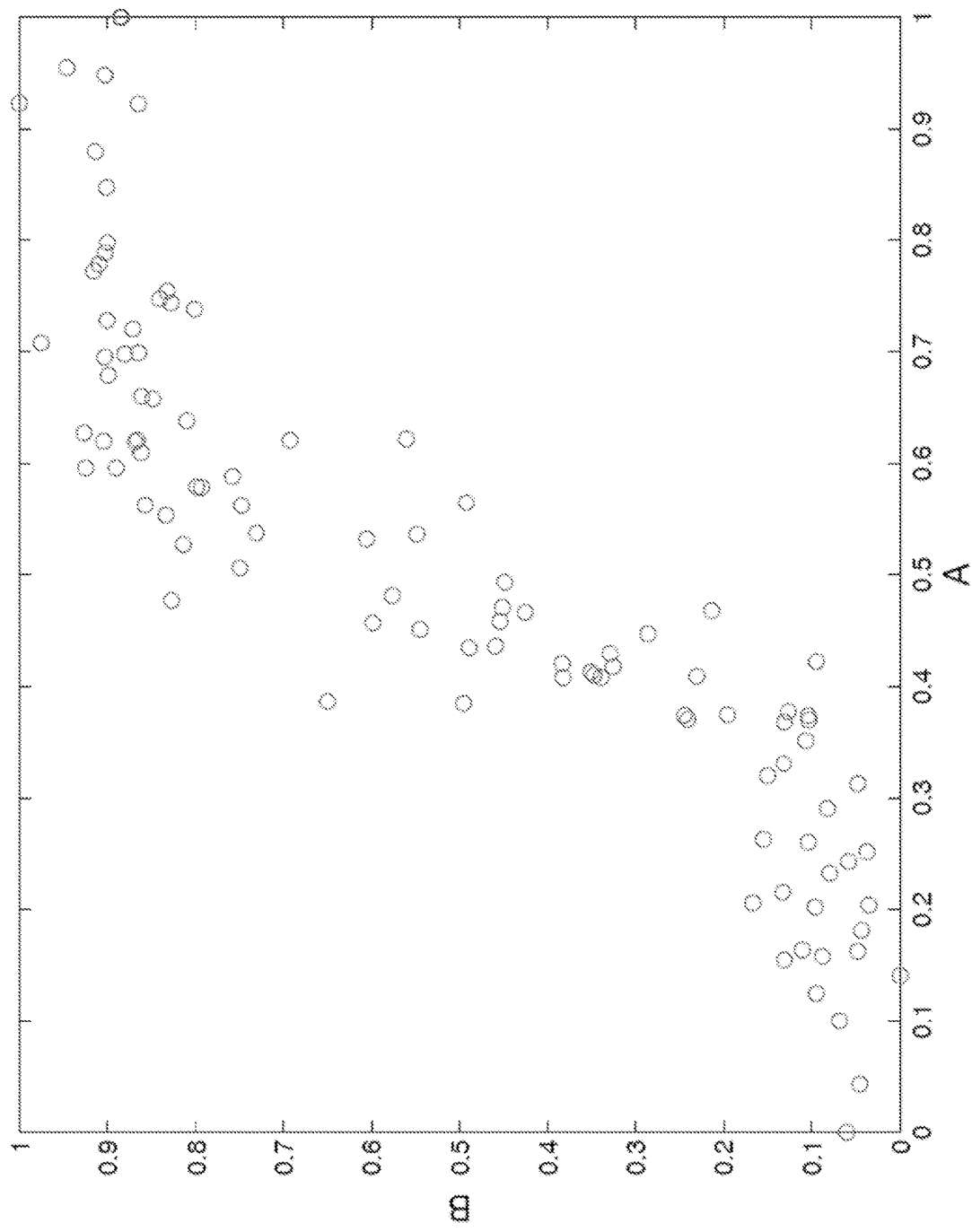
FIG. 19 depicts (A vs. B) synthetic data (rescaled to [0,1]) with low noise, where the parent node A is sampled from a Gaussian distribution, and values of B are generated in accordance with the interaction function B=f(A), where f is a hill function, based upon the ground truth structure $G_1$ of FIG. 2, in accordance with an exemplary embodiment.
Figure 20:
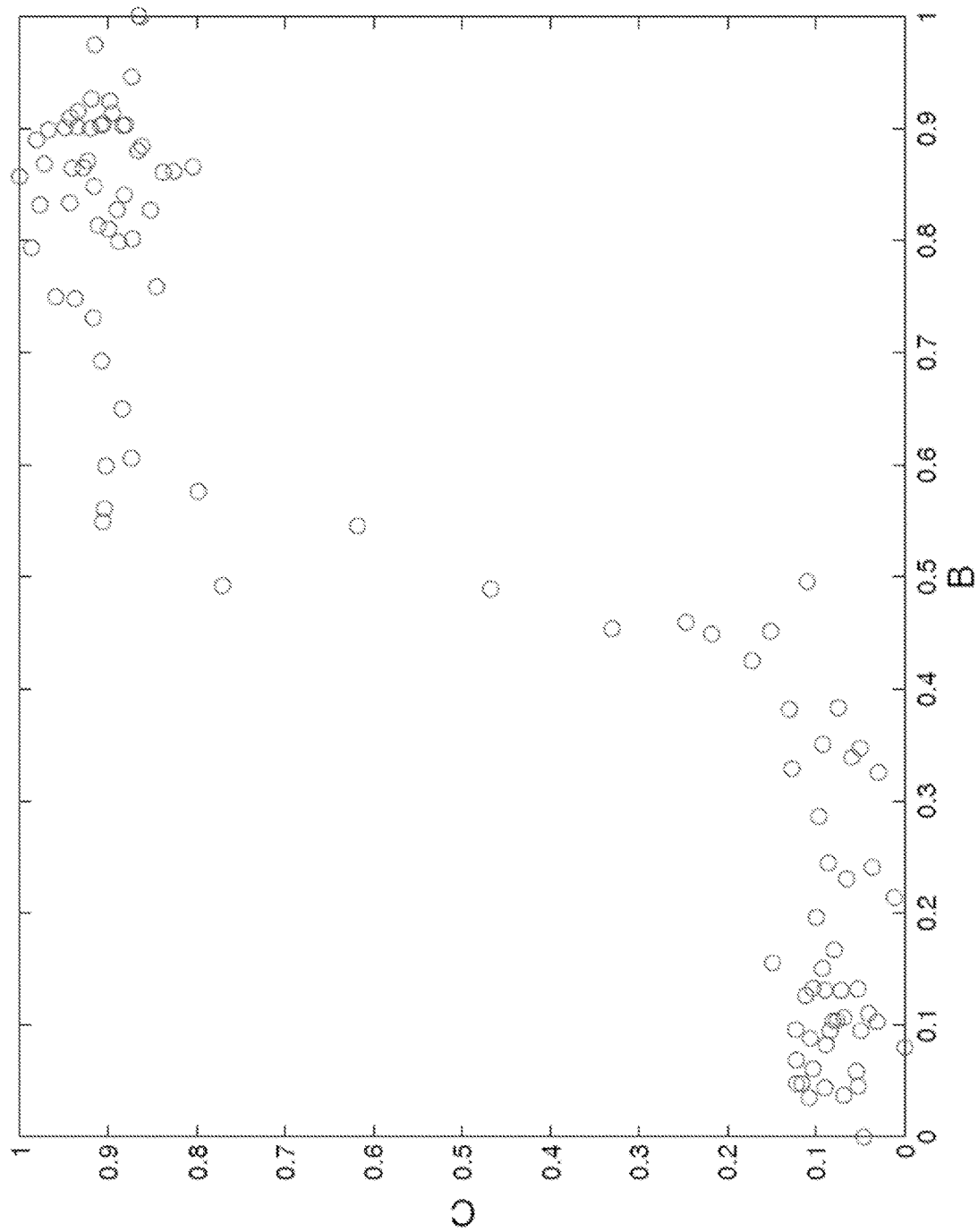
FIG. 20 depicts (B vs. C) synthetic data (rescaled to [0,1]) with low noise, where the values of C are generated in accordance with the interaction function C=g(B) using the values for B from FIG. 19, where g is a hill function, based upon the ground truth structure $G_1$ of FIG. 2, in accordance with an exemplary embodiment.
Figure 21:
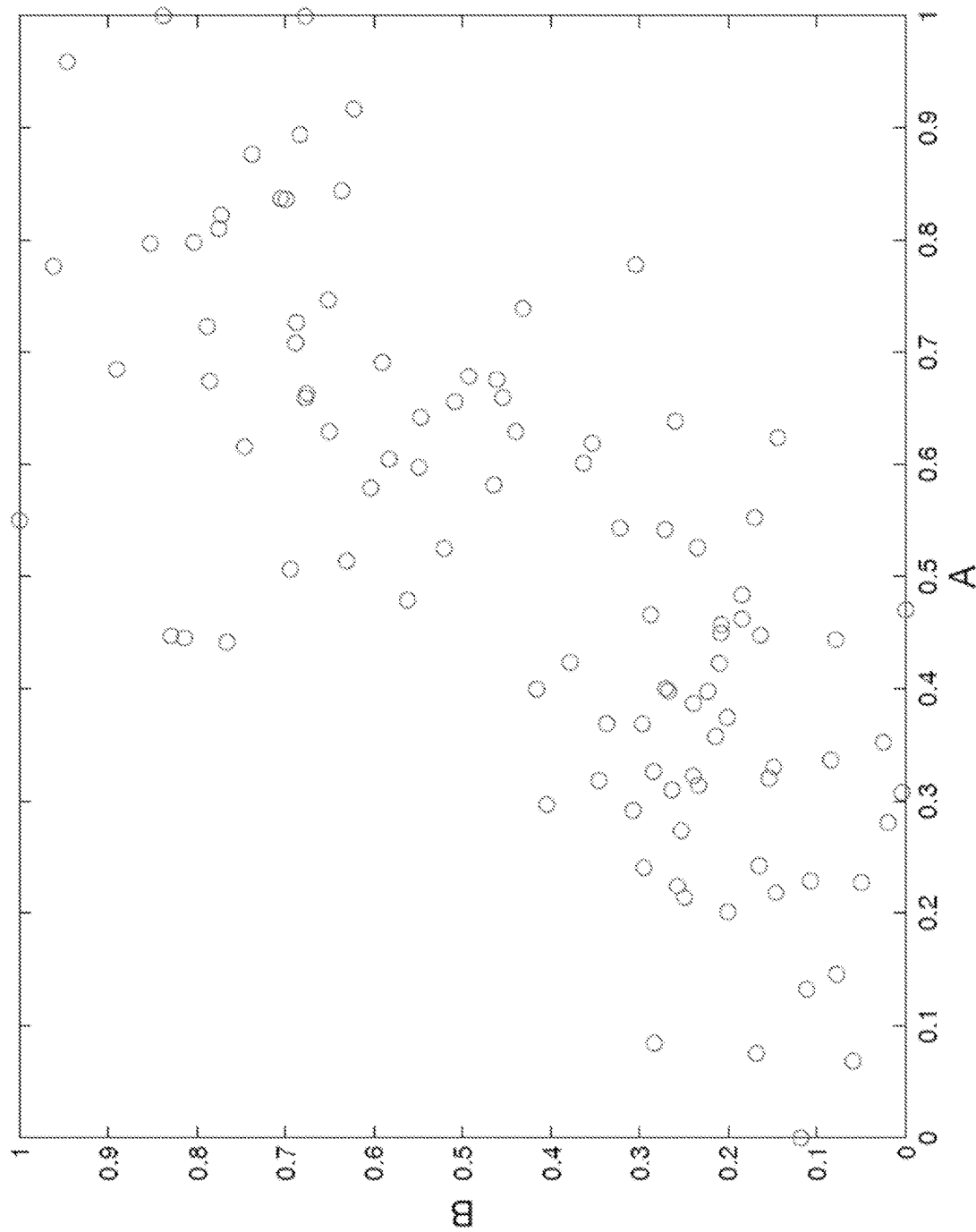
FIG. 21 depicts (A vs. B) synthetic data (rescaled to [0,1]) with high noise, where the parent node A is sampled from a Gaussian distribution, and values of B are generated in accordance with the interaction function B=f(A), where f is a hill function, based upon the ground truth structure $G_1$ of FIG. 2, in accordance with an exemplary embodiment.
Figure 22:
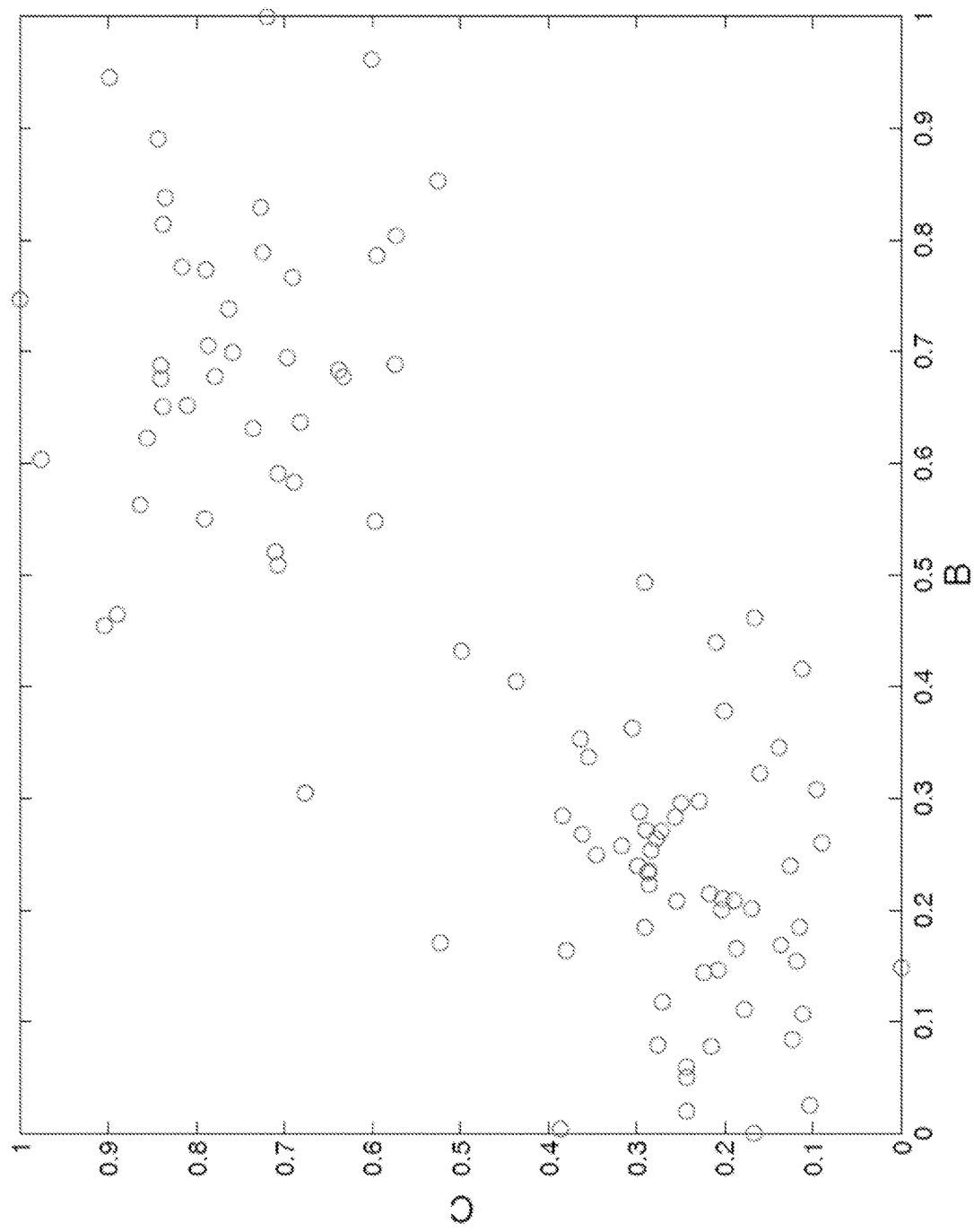
FIG. 22 depicts (B vs. C) synthetic data (rescaled to [0,1]) with high noise, where the values of C are generated in accordance with the interaction function C=g(B) using the values for B from FIG. 21, where g is a hill function, based upon the ground truth structure $G_1$ of FIG. 2, in accordance with an exemplary embodiment.
Figure 23:
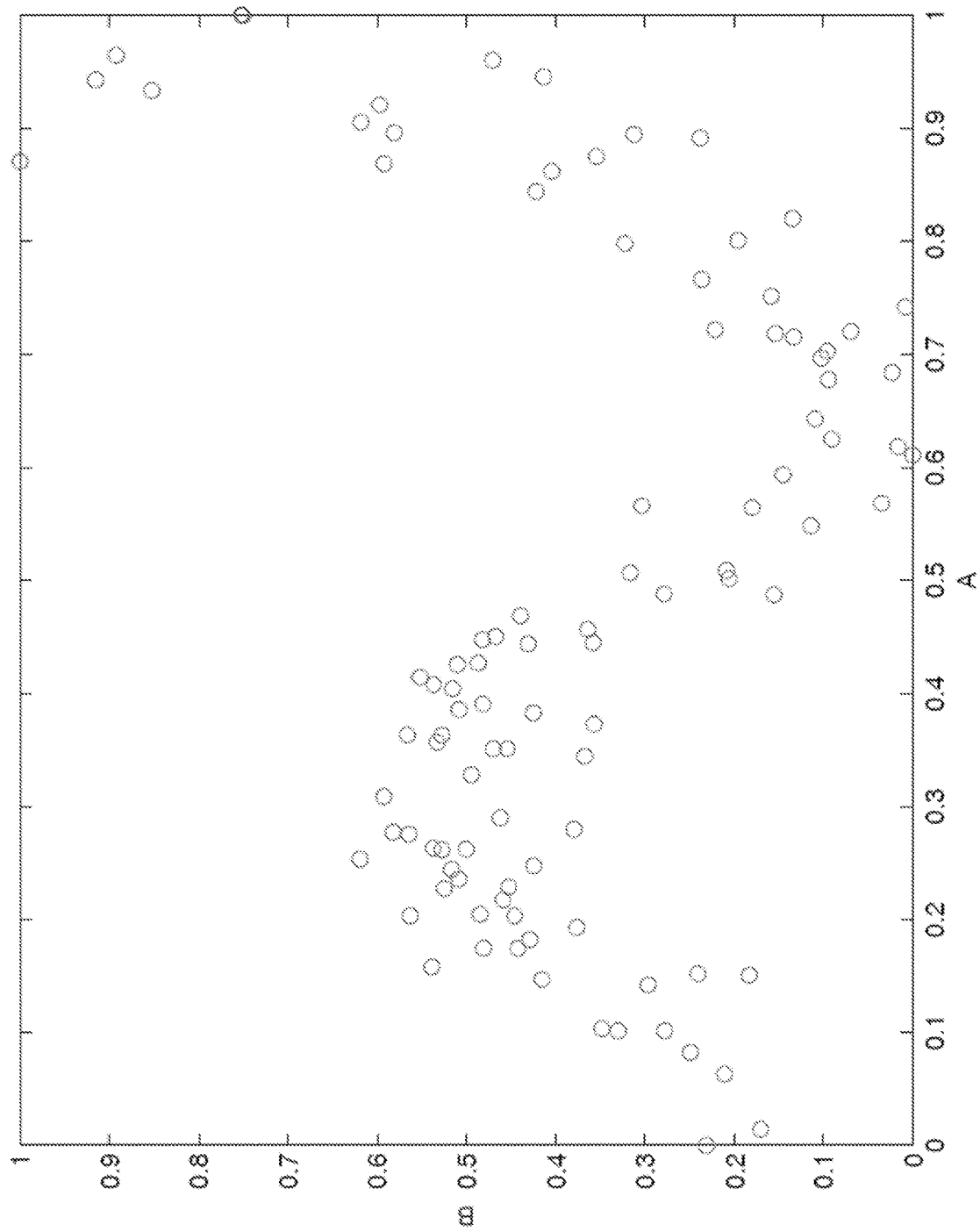
FIG. 23 depicts (A vs. B) synthetic data (rescaled to [0,1]) with low noise, where the parent node A is sampled from a uniform distribution, and values for B are generated in accordance with the interaction function B=f(A), where f is a nonlinear function, based upon the around truth structure $G_1$ of FIG. 2, in accordance with an exemplary embodiment.
Figure 24:
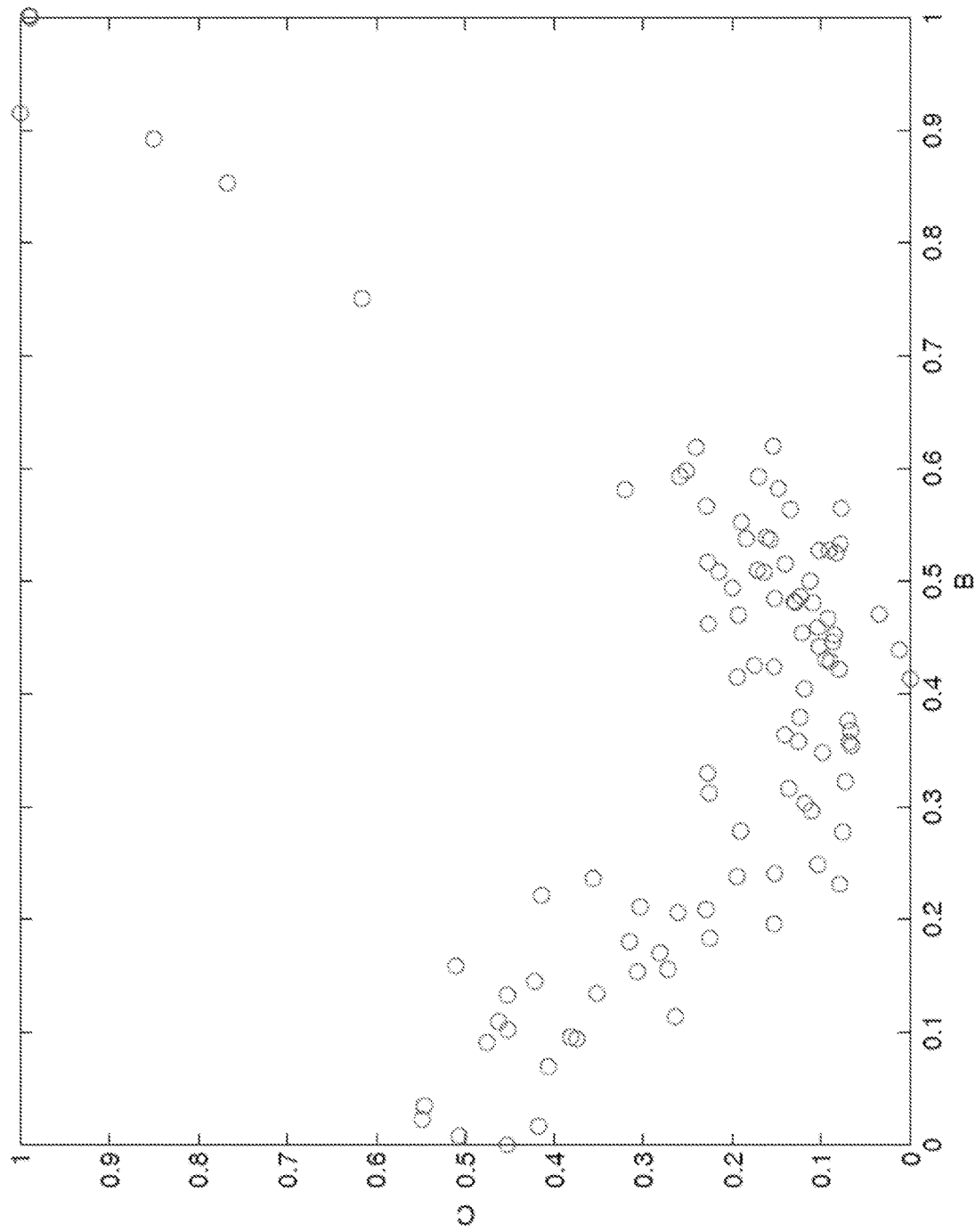
FIG. 24 depicts (B vs. C) synthetic data (rescaled to [0,1]) with low noise, where the values of C are generated in accordance with the interaction function C=g(B) using the values for B from FIG. 23, where g is a nonlinear function, based upon the ground truth structure $G_1$ of FIG. 2, in accordance with an exemplary embodiment.
Figure 25:
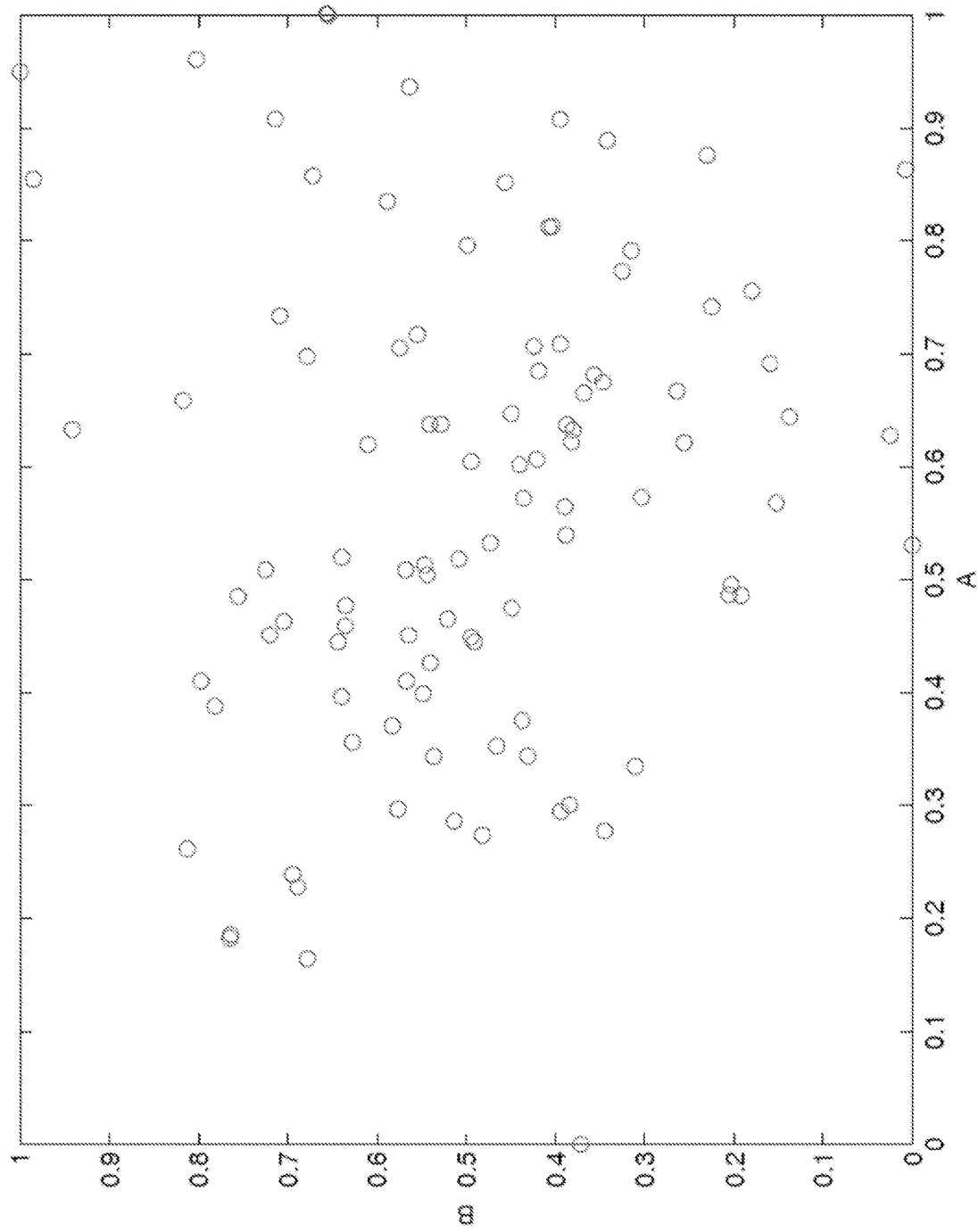
FIG. 25 depicts (A vs. B) synthetic data (rescaled to [0,1]) with high noise, where the parent node A is sampled from a uniform distribution, and values for B are generated in accordance with the interaction function B=f(A), where f is a nonlinear function, based upon the ground truth structure $G_1$ of FIG. 2, in accordance with an exemplary embodiment.
Figure 26:
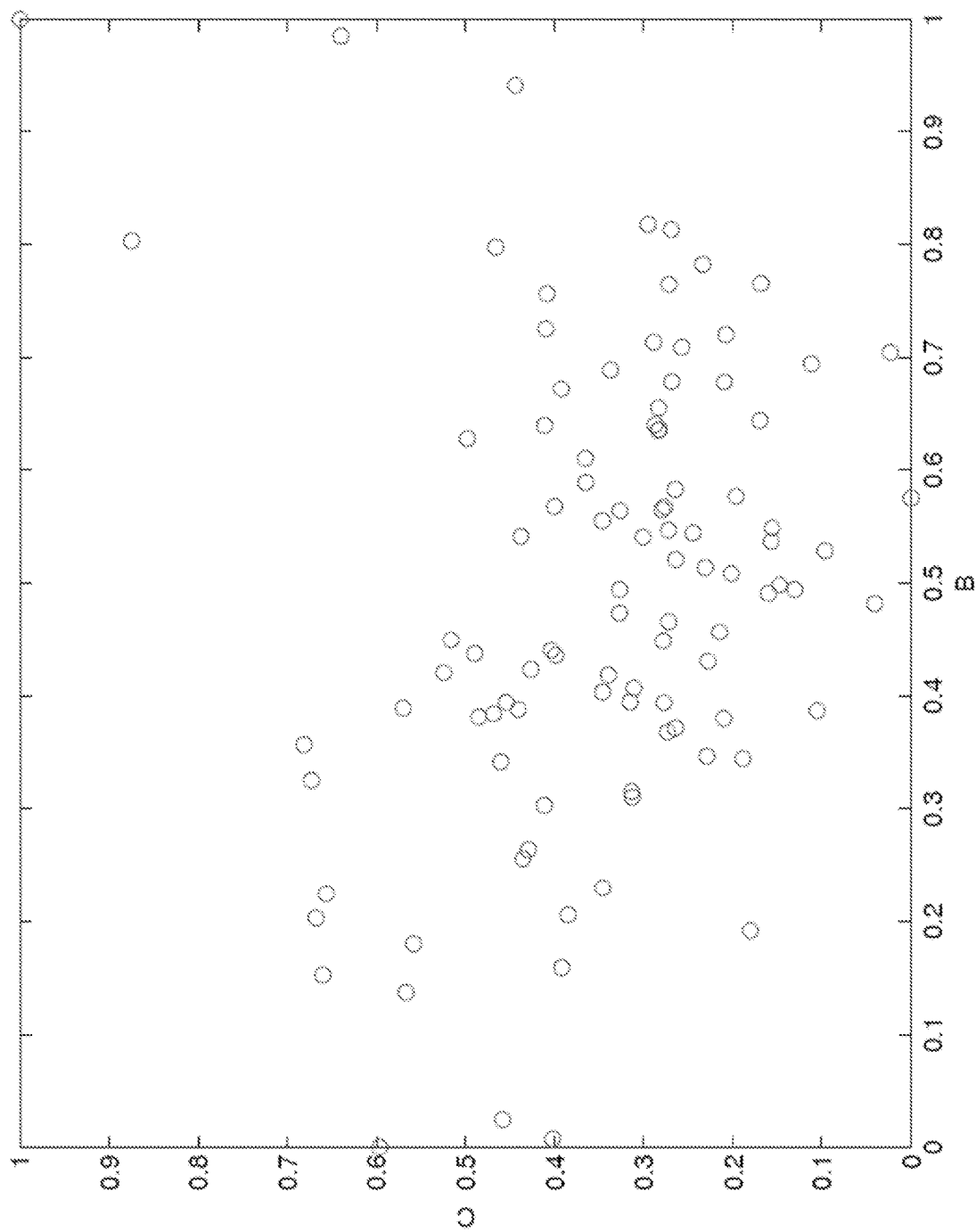
FIG. 26 depicts (B vs. C) synthetic data (rescaled to [0, 1]) with high noise, where the values of C are generated in accordance with the interaction function C=g(B) using the values for B from FIG. 25, where g is a nonlinear function, based upon the ground truth structure $G_1$ of FIG. 2, in accordance with an exemplary embodiment.
Figure 27:
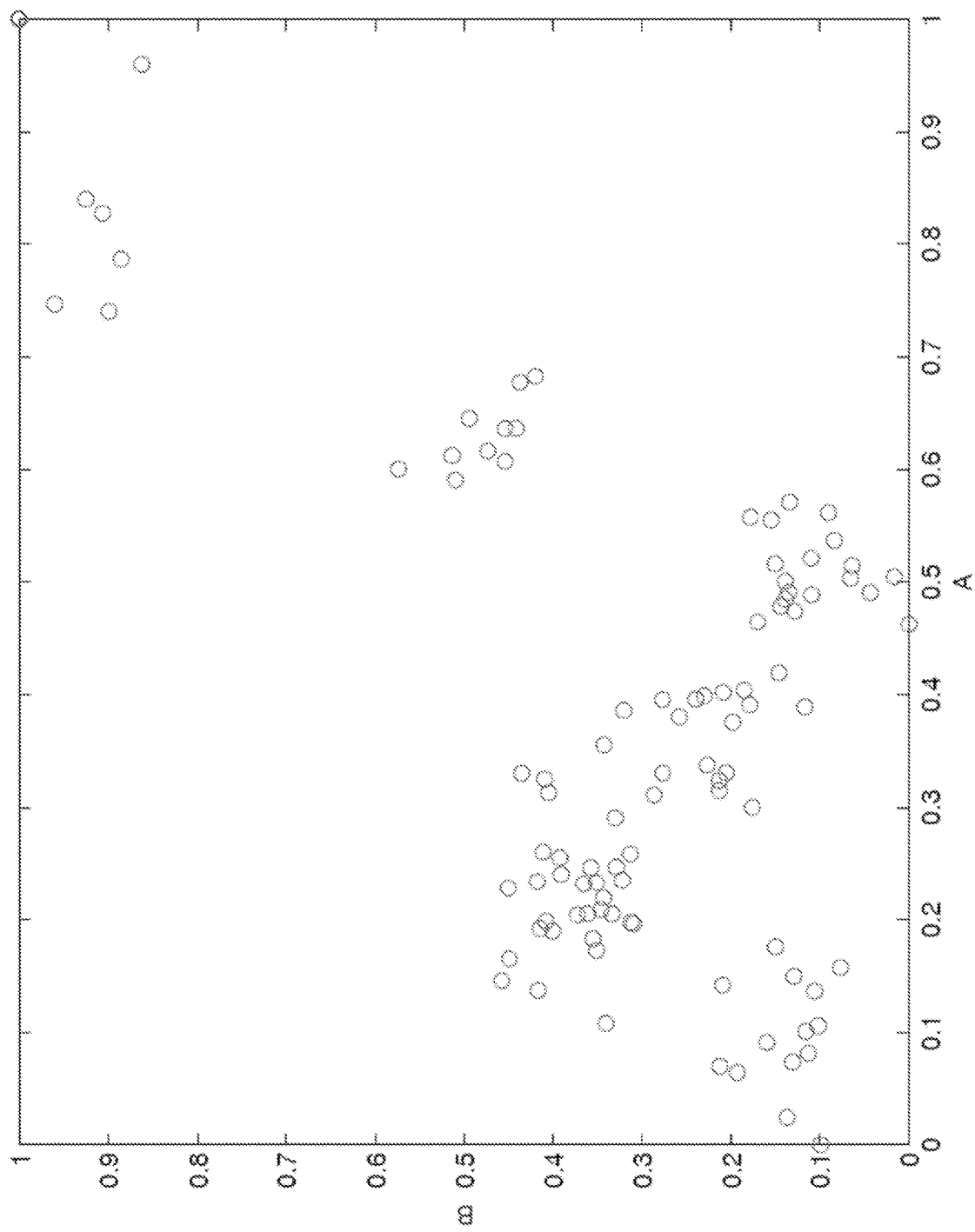
FIG. 27 depicts (A vs. B) synthetic data (rescaled to [0,1]) with low noise, where the parent node A is sampled from a Poisson distribution, and values for B are generated in accordance with the interaction function B=f(A), where f is a nonlinear function, based upon the ground truth structure $G_1$ of FIG. 2, in accordance with an exemplary embodiment.
Figure 28:
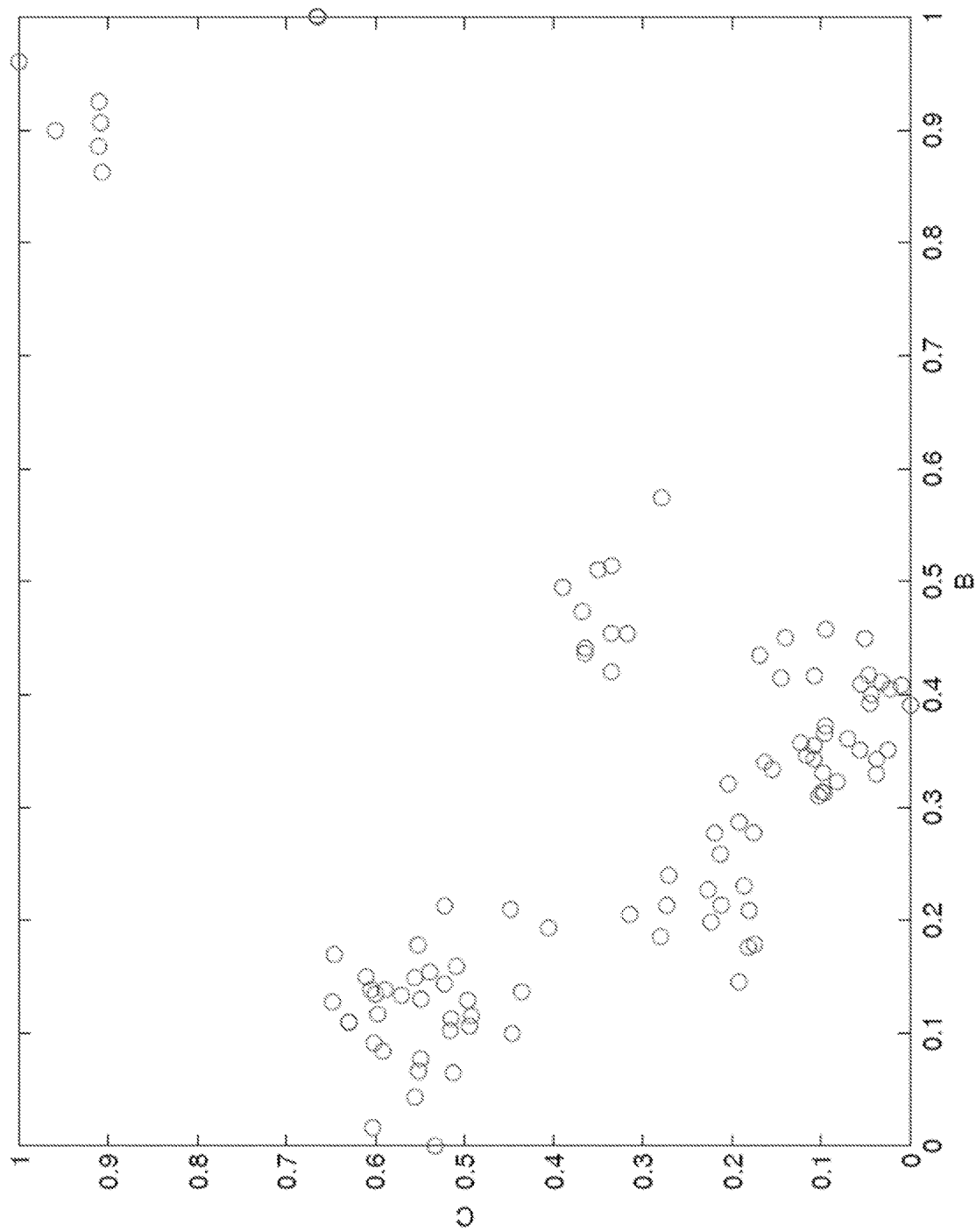
FIG. 28 depicts (B vs. C) synthetic data (rescaled to [0,1]) with low noise, where the values of C are generated in accordance with the interaction function C=g(B) using the values for B from FIG. 27, where g is a nonlinear function, based upon the ground truth structure $G_1$ of FIG. 2, in accordance with an exemplary embodiment.
Figure 29:
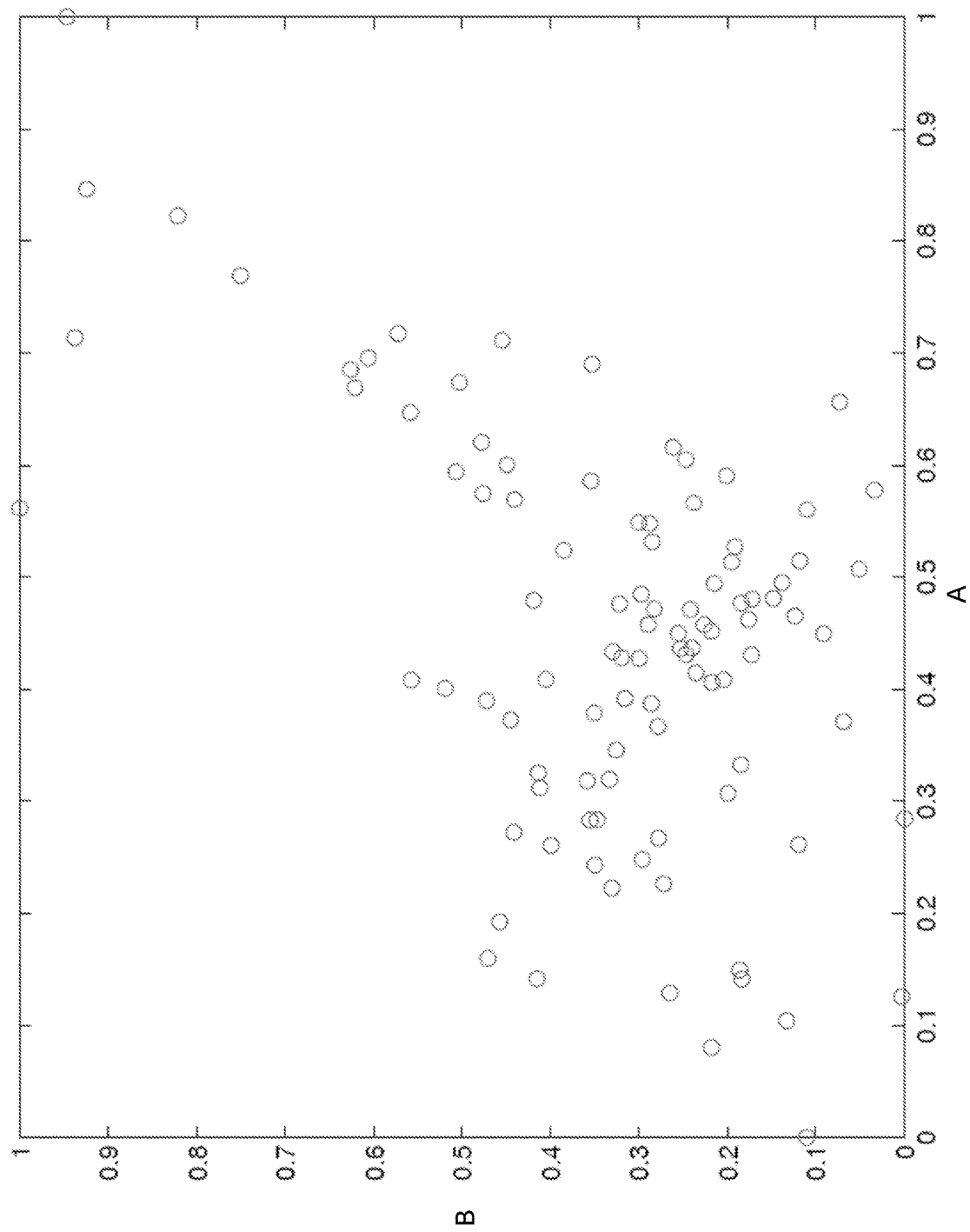
FIG. 29 depicts (A vs. B) synthetic data (rescaled to [0,1]) with high noise, where the parent node A is sampled from a Poisson distribution, and values for B are generated in accordance with the interaction function B=f(A), where f is a nonlinear function, based upon the ground truth structure $G_1$ of FIG. 2, in accordance with an exemplary embodiment.
Figure 30:
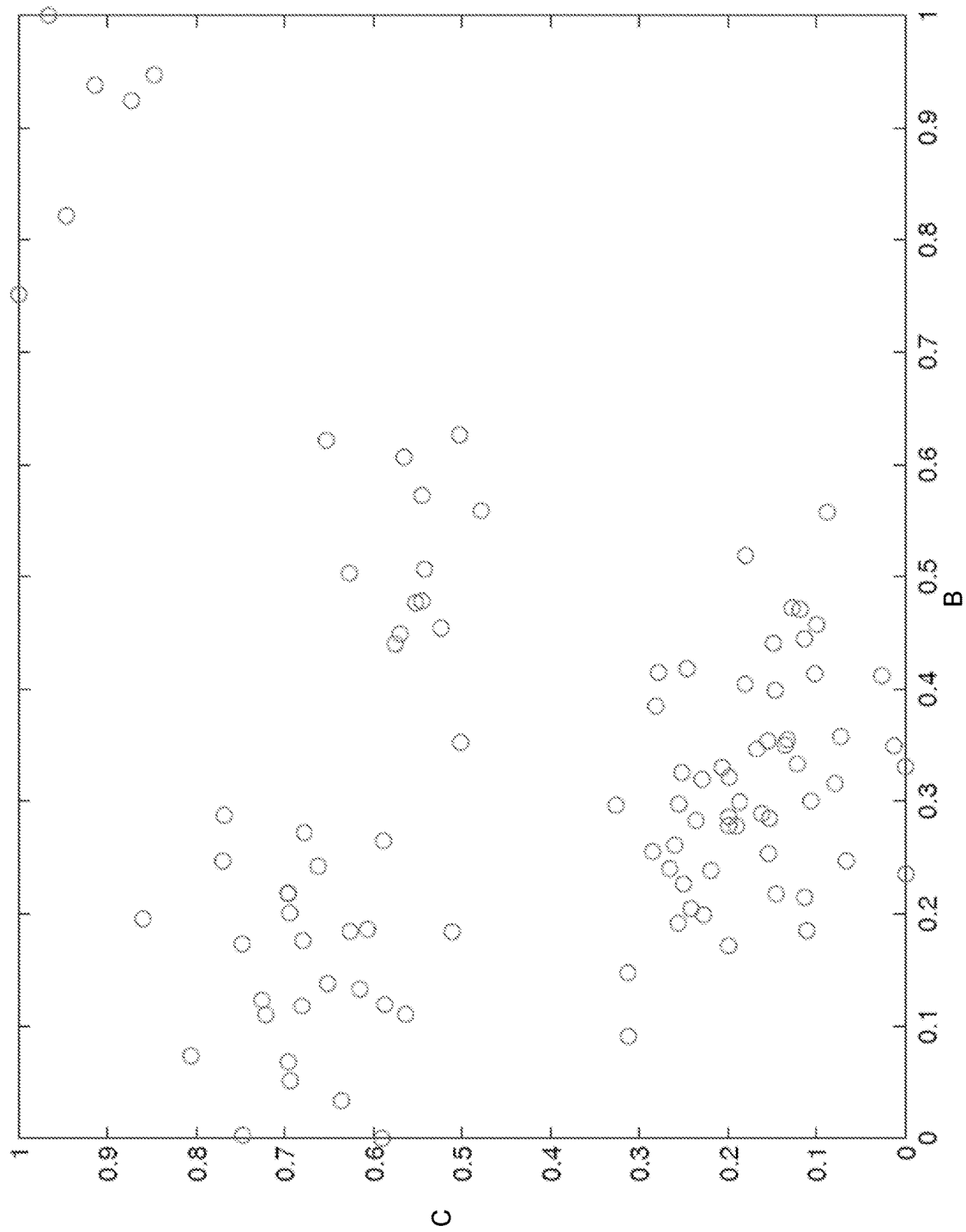
FIG. 30 depicts (B vs. C) synthetic data (rescaled to [0,1]) with high noise, where the values of C are generated in accordance with the interaction function C=g(B) using the values for B from FIG. 29, where g is a nonlinear function, based upon the ground truth structure $G_1$ of FIG. 2, in accordance with an exemplary embodiment.
Figure 31:
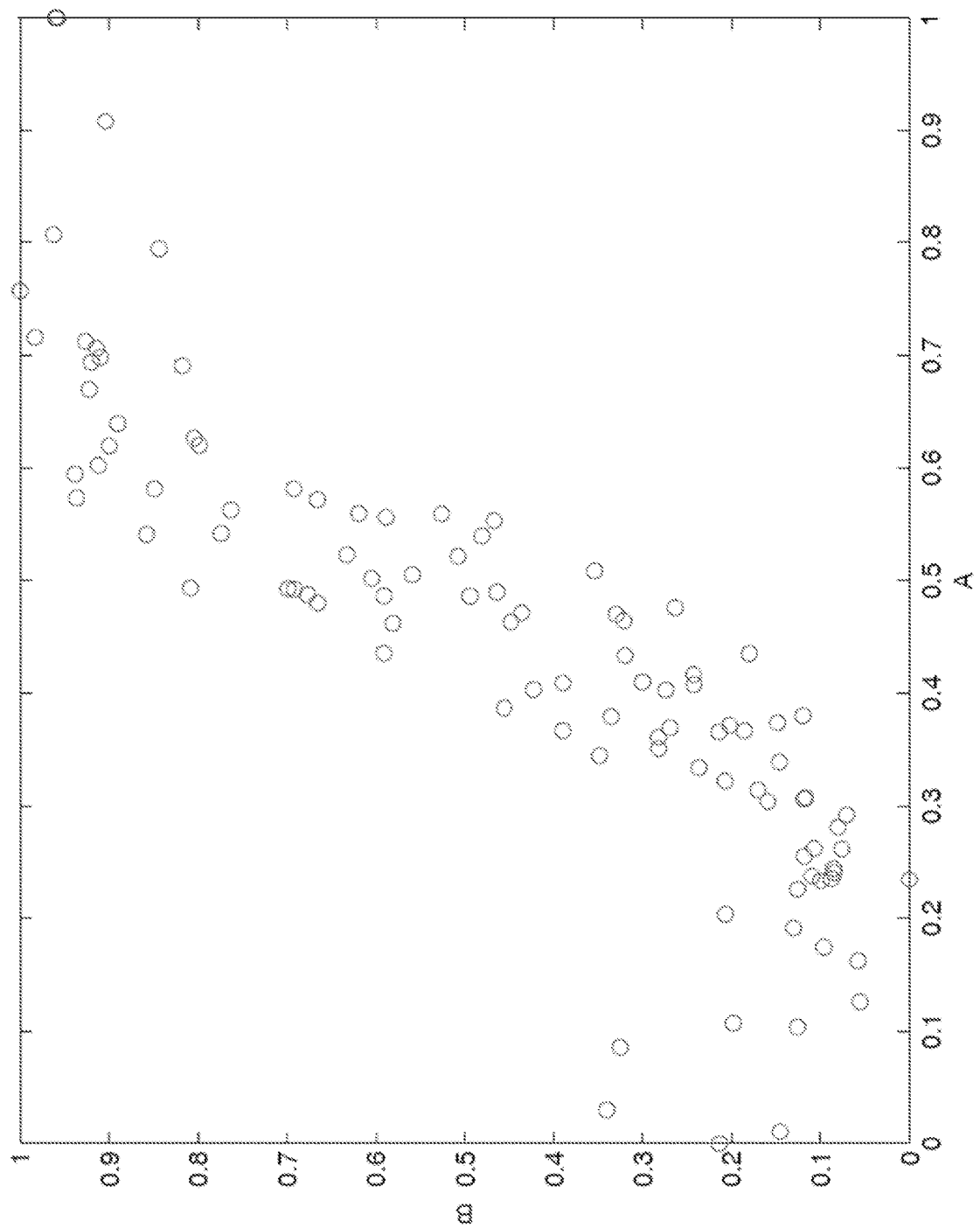
FIG. 31 depicts (A vs. B) synthetic data (rescaled to [0,1]) with low noise, where the parent node A is sampled from a Gaussian distribution, and values for B are generated in accordance with the interaction function B=f(A), where f is a nonlinear function, based upon the ground truth structure $G_1$ of FIG. 2, in accordance with an exemplary embodiment.
Figure 32:
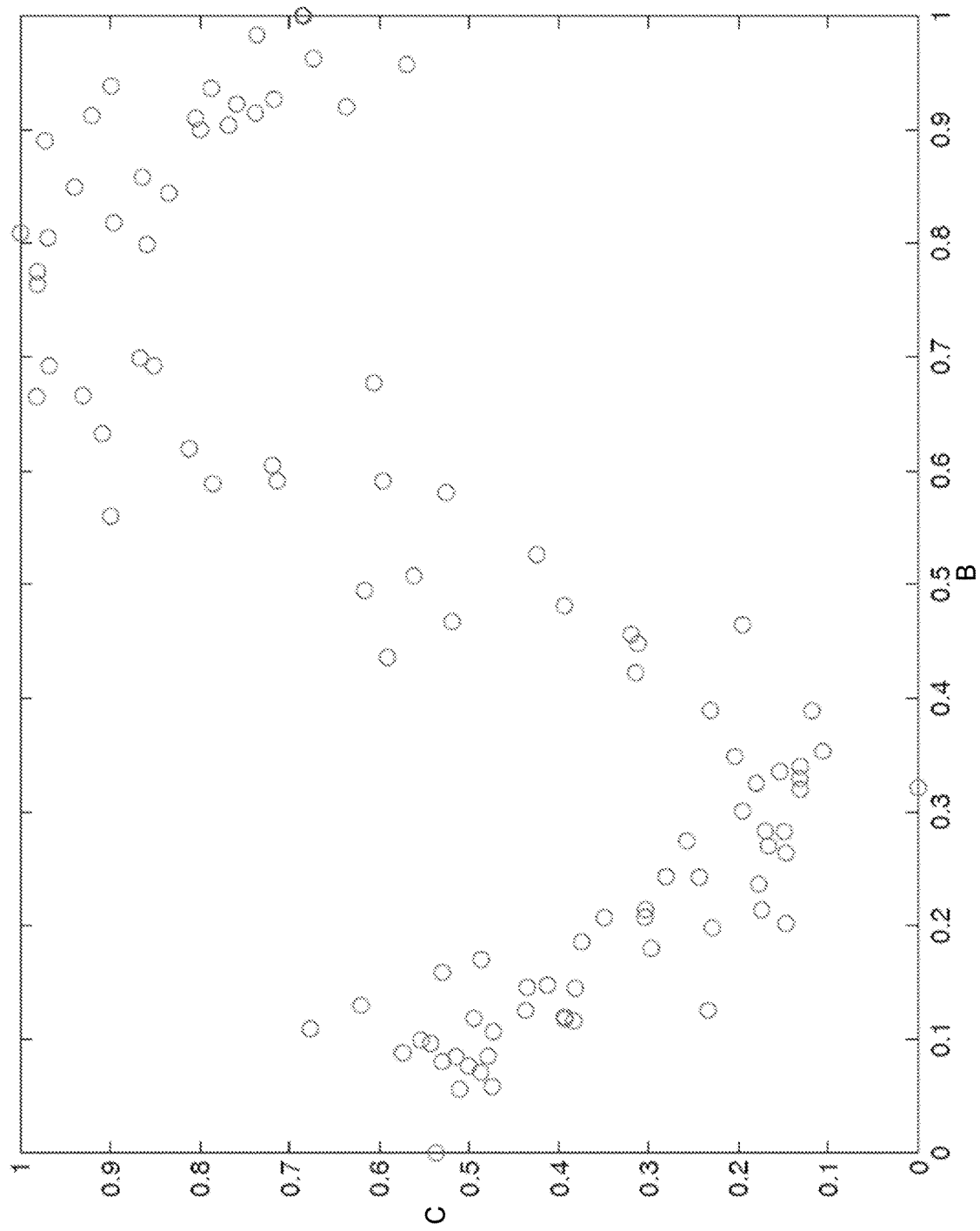
FIG. 32 depicts (B vs. C) synthetic data (rescaled to [0,1]) with low noise, where the values of C are generated in accordance with the interaction function C=g(B) using the values for B from FIG. 31, where g is a nonlinear function, based upon the ground truth structure $G_1$ of FIG. 2, in accordance with an exemplary embodiment.
Figure 33:
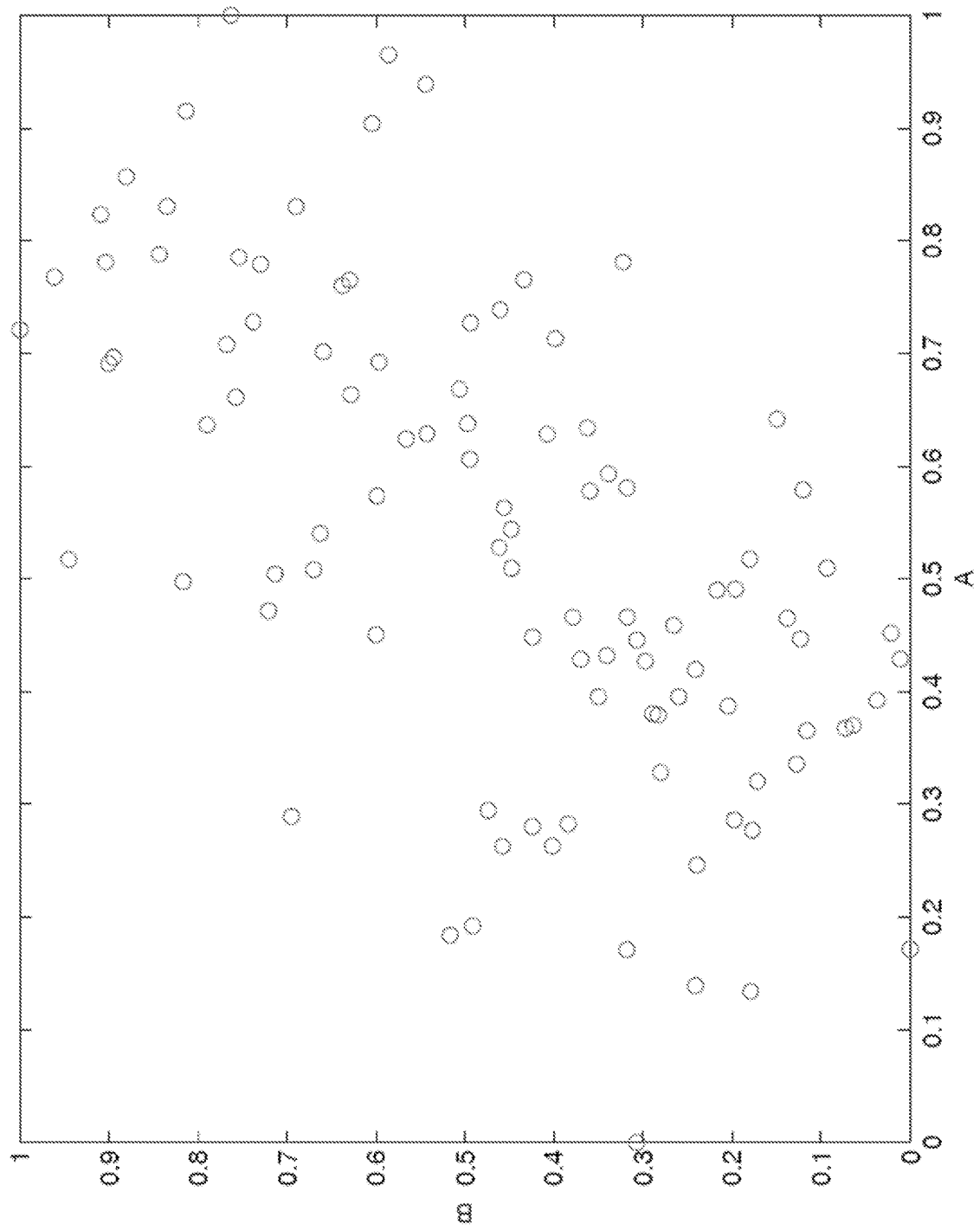
FIG. 33 depicts (A vs. B) synthetic data (rescaled to [0,1]) with high noise, where the parent node A is sampled from a Gaussian distribution and values for B are generated in accordance with the interaction function B=f(A), where f is a nonlinear function, based upon the ground truth structure $G_1$ of FIG. 2, in accordance with an exemplary embodiment.
Figure 34:
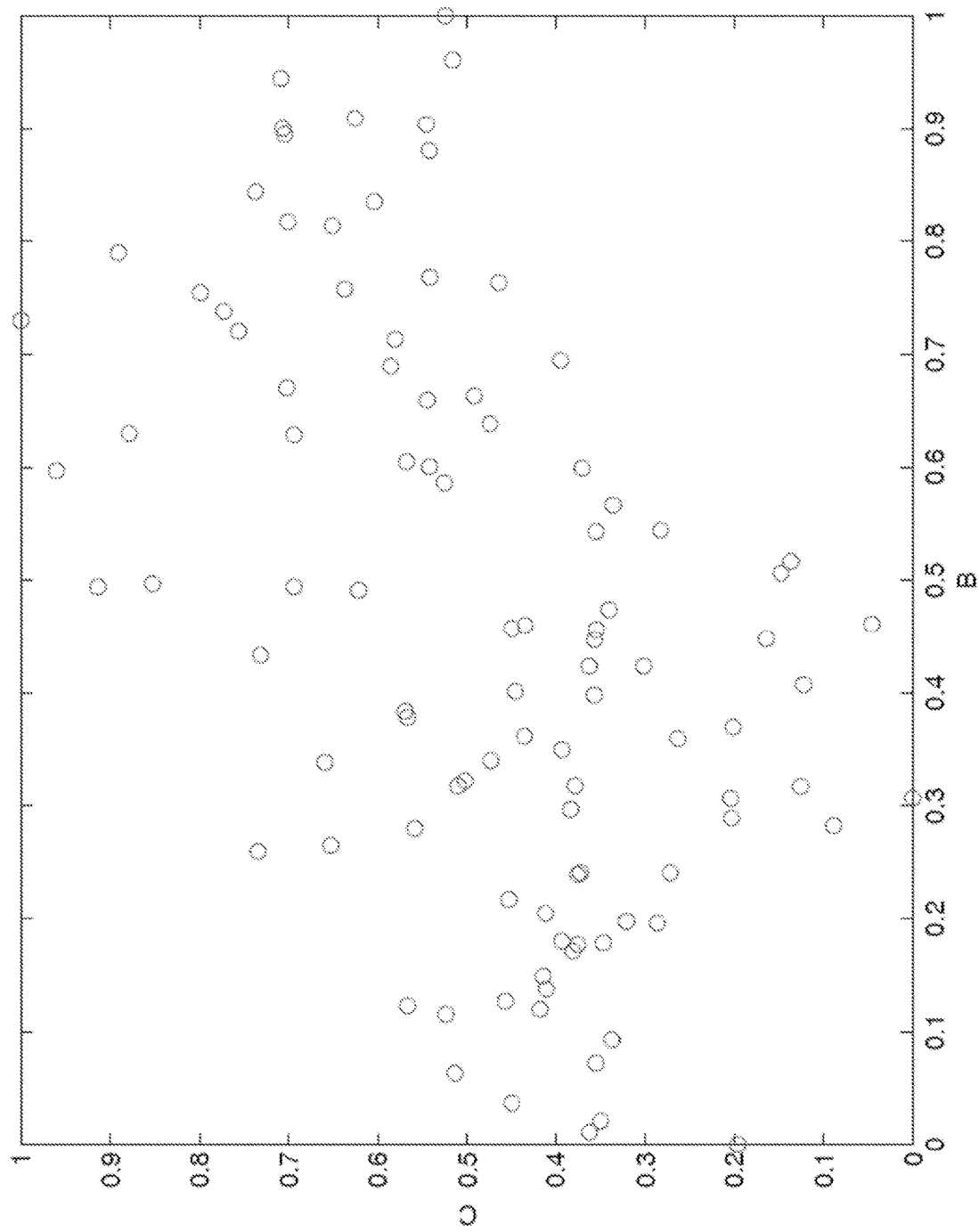
FIG. 34 depicts (B vs. C) synthetic data (rescaled to [0,1]) with high noise, where the values of C are generated in accordance with the interaction function C=g(B) using the values for B from FIG. 33, where g is a nonlinear function, based upon the ground truth structure $G_1$ of FIG. 2, in accordance with an exemplary embodiment.

FIG. 3 and FIG. 5 respectively show the fit of the regression model in the true (A→B) and false (A←B) causal directions. The linear regression (LR) model is depicted by the line in each segment. The distribution of the predictor variable (parent node) in the case where A is assumed to be the predictor variable (corresponding to FIG. 3) is shown in FIG. 4. The distribution of the predictor variable (parent node) in the case where B is assumed to be the predictor variable (corresponding to FIG. 5) is shown in FIG. 6. The distribution of the response variables (child nodes) are shown in FIGS. 7 through 10. In FIGS. 7 and 8, A is the parent and its belief probability is clamped according to the observed and fitted distributions of the predicted values of the child node B. If the predicted values of B (FIG. 8) well match the observations (FIG. 7), the likelihood score for (A→B) will be increased relative to the likelihood score for (A←B), which represents the opposite relationship (B as the parent node and A as the child). It is noted that in (A←B) for the 'flat' regions (Sectors I and IV) of the interaction function, the fitted linear regression does not cover the full range of values A can take on in these segments, which results in a truncation of the distribution of A at the ends of these two segments, resulting in a worse likelihood score compared to the true causal direction.

The asymmetric performance in predicting values along the true and false causal directions results from the constraints ([−1,1] in Eq. 4) defined for the disclosed pairwise causality test, which constrains the slope coefficient to fall ∈[−1,1] and the intercept coefficient to fall ∈[0,1] for each segment. These constraints enforce an asymmetry in the fit of the regression model between the true and false causal directions needed to infer the true direction. It is also assumed that any nonlinear curve can be well approximated by a piecewise linear regression (LR) model. That is, in each segment the linear regression is good enough when fitting along the true causal direction. When a segment is fit along the correct causal direction (i.e., the segment is assumed to lie in the dimension of the parent node and is mapped to the child node via the regression function), the length to set for the segment should be determined by the degree of noise in the data. If noise levels are low (high) along the true causal direction, then the size of the segment can be longer (shorter) with a smaller (larger) number of segments. In the present case, given the slope and intercept coefficients are constrained in the linear regression, the belief propagation is able to fit the distribution of noisy observations well so long as the segment size is small enough. However, if the segment is fit along the wrong causal direction, the length of the segment will no longer help scatter the observed data into different segments, given the distribution of observed values of the child nodes in the flat or U shaped regions of the distribution of the parent nodes are not be completely captured, but instead are truncated as discussed above. As a result, there will be a high probability of the observed values on the child nodes falling in the same segment no matter how small the segment size is or how low the noise level is. In this case, the ideal length of the segment will be determined by the shape of the interaction function.

It is noted that while the case can be made that smaller-sized segments will not significantly improve the fit along the wrong causal dimension, the possibility that the distribution of the true parent node given the child node (wrong causal direction) is well approximated across the different segments (i.e., the truncation of the ends of the distribution discussed above goes away) has not been ruled out when an extremely small segment size is chosen. If such a case were to arise, the likelihood score would be equally good in the true and false causal directions. Similarly, if the segment size chosen is too big, the possibility exists that even along the correct causal dimension, the coverage of the predicted distribution of the child node may not be complete, making the likelihood score in the true and false causal directions equally bad. As such, choice of optimal segment sizes and positions is application dependent.

Example 2—Distinguishing Between Triple-Node Structures that are Markov Equivalent Now that a two-node problem has been tested, a formal test of a more difficult problem is addressed using the systems and methods of the present disclosure: distinguishing among triple-node structures that are Markov equivalent. For this problem the disclosed systems and methods were tested using two types of interaction functions: 1) a hill function which is a standard biological form that reflects activation/inhibition relationships and 2) nonlinear & non-monotonic functions that capture feedback control relationships. For each type of interaction function, datasets were generated that comprised 100 samples (a typical sample size in biological experiments) based on the ground truth structure $G_1$ depicted in FIG. 2. The samples were simulated using different distributions: Uniform (U), Gaussian (G) and Poisson (P), to mimic microarray and RNA-sequencing gene expression data. For each simulation, the parent node A was sampled from the U, G and P distributions. Values of B and C were then generated according to the interaction functions B=f(A) and C=g(B). Gaussian noise was also simulated to reflect technological variation inherent in the types of measures made in biology and this noise was added to the values of A, B and C to formalize the observation data D. The graphical structures depicted in FIG. 2 are Markov equivalent and so in the context of conventional Bayesian networks they all give rise to the same data likelihood, and thus, are statistically indistinguishable from one another. The disclosed systems and methods correctly infer causality in this case, given explicit assumptions on the nature of the interaction between the parent and child nodes, as well as on the distribution of these nodes.

FIGS. 11-22 depict the synthetic data (rescaled to [0,1]) generated from a hill function. FIGS. 23-34 depict the synthetic data (rescaled to [0,1]) generated from a nonlinear-nonmonotonic function. The standard deviation (σ) under the low noise condition was set to 0.05, resulting in an approximate signal-to-noise ratio (SNR) of 15-19 dB, and the σ under high noise conditions was set to 0.2, resulting in an approximate SNR of 3-7 dB. In total, twelve datasets are generated from the uniform, Poisson, and Gaussian distributions for two interaction functions with two different noise levels. Given each dataset, to assess the goodness of fits across the different models for the different simulated datasets, the KL-divergence (Eq. 6) was calculated between the predicted and observed distributions for each response variable (child node). The total score for any given structure is computed as the sum of each causal edge's score. The model with the lowest KL-divergence value is identified as the model best supported by the data.

Focusing on the harder high-noise condition, the predicted distribution for each response variable (child node) from the linear regression model fitted to the data, given each equivalent structure and dataset, are shown in FIGS. 35-40. In each figure, the top row depicts the true distribution of every node (A, B and C) in the observed data D, which also represents the distribution of the parent node given the current structure hypothesis. The second and third row of each column in FIGS. 35-40 shows the fitted distribution under each equivalent structure (left to right: $G_1$, $G_2$, $G_3$).

Figure 35:
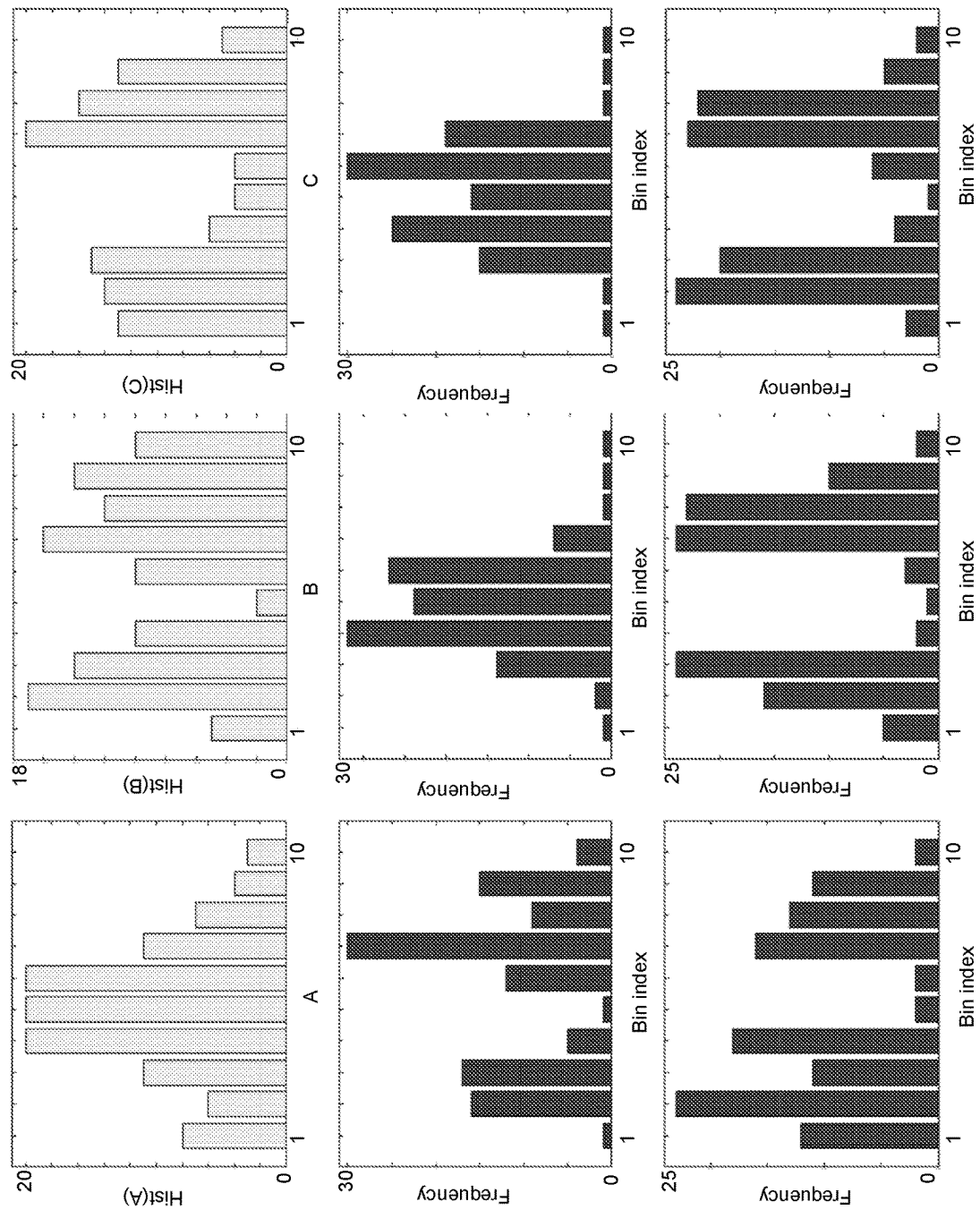
FIG. 35, first row, provides three plots representing the true distribution of A, B and C, respectively, for data acquired from a uniform distribution.

To illustrate, in FIG. 35, the plot on the first row represents the true distribution of A, B and C. In the first column of FIG. 35, the lower two bar plots respective represent the optimized distribution of B and C in $G_1$. In the first column of FIG. 35, A is the perturbed node whose value is clamped according to the dataset D and the values of B and C are inferred in $G_1$ by Bayesian network belief propagation procedure for each sampled set of model parameter θ. The optimal predicted values of B and C are those that minimize the cost function in Equation 6. In the second column of FIG. 35, node B is considered as the parent node. Given the value of B, the belief probability of nodes A and C are inferred in $G_2$ for each sampled model parameter. The distribution of the optimal predicted values A and C are respectively shown in the lower two plots of the second column. In the third column of FIG. 35, node C is perturbed and nodes B and A are predicted sequentially (i.e., B is predicted from C and then A is predicted from predicted B in accordance with $G_3$ of FIG. 2). The distribution of the optimal predicted values for A and B are respectively shown in the lower two plots of the third column.

In FIG. 35, data for the parent node is obtained from a uniform distribution and the interaction functions for the child nodes are Hill functions.

Figure 36:
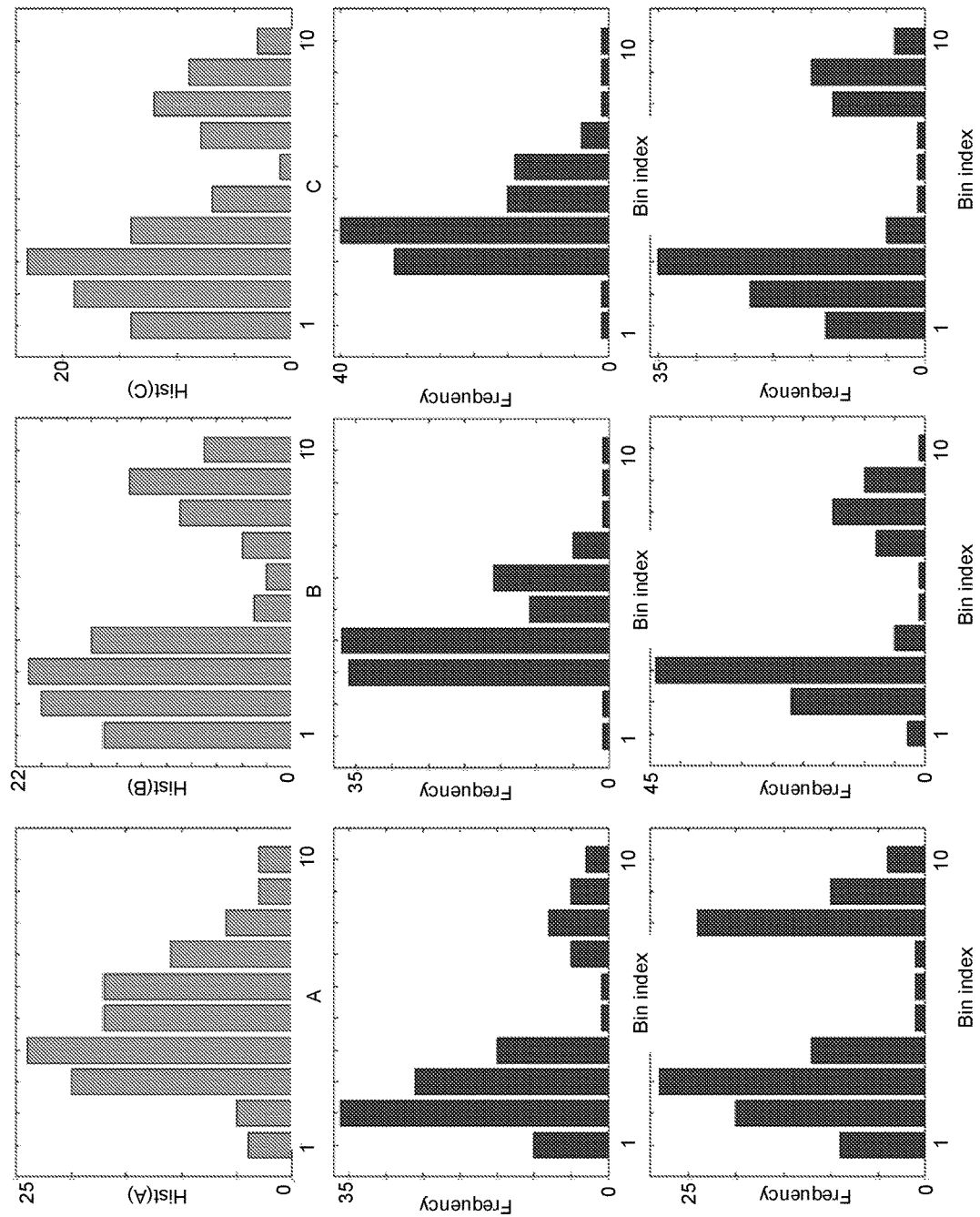
FIG. 36 is a plot of the form shown in FIG. 35 with the exception that data for the respective parent nodes (A, first column, B, second column, and C, third column) is obtained from a Poisson distribution and the interaction functions for the child nodes are Hill functions, in accordance with an embodiment of the present disclosure.

In FIG. 36, data for the parent node is obtained from a Poisson distribution and the interaction functions for the child nodes are Hill functions.

Figure 37:
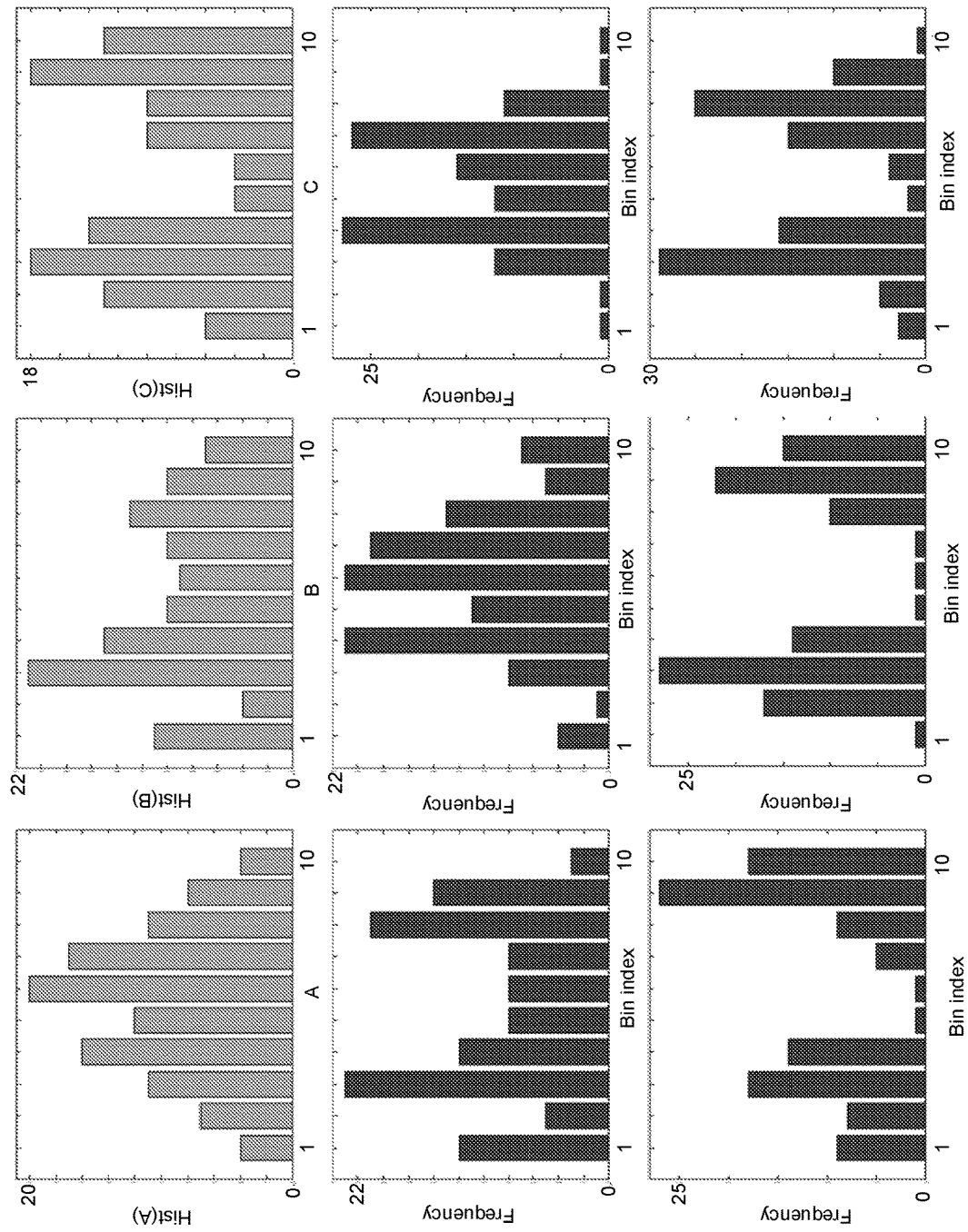
FIG. 37 is a plot of the form shown in FIG. 35 with the exception that the data for the respective parent nodes (A, first column, B, second column, and C, third column) is obtained from a Gaussian distribution and the interaction functions for the child nodes are Hill functions, in accordance with an embodiment of the present disclosure.

In FIG. 37, data for the parent node is obtained from a Gaussian distribution and the interaction functions for the child nodes are Hill functions.

Figure 38:
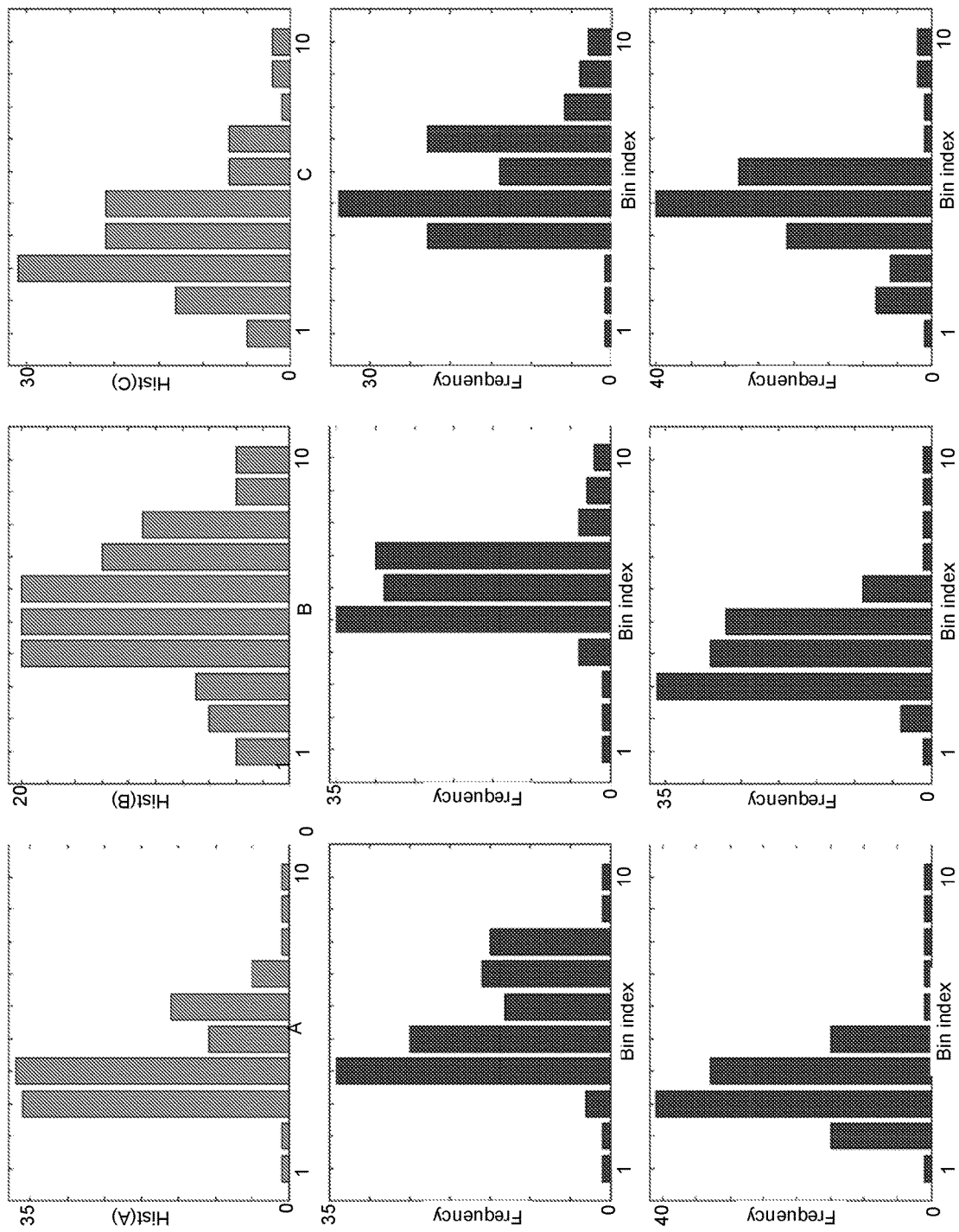
FIG. 38 is a plot of the form shown in FIG. 35 with the exception that the data for the respective parent nodes (A, first column, B, second column, and C, third column) is obtained from a uniform distribution and the interaction functions for the child nodes are nonlinear, in accordance with an embodiment of the present disclosure.

In FIG. 38, data for the parent node is obtained from a uniform distribution and the interaction functions for the child nodes are nonlinear.

Figure 39:
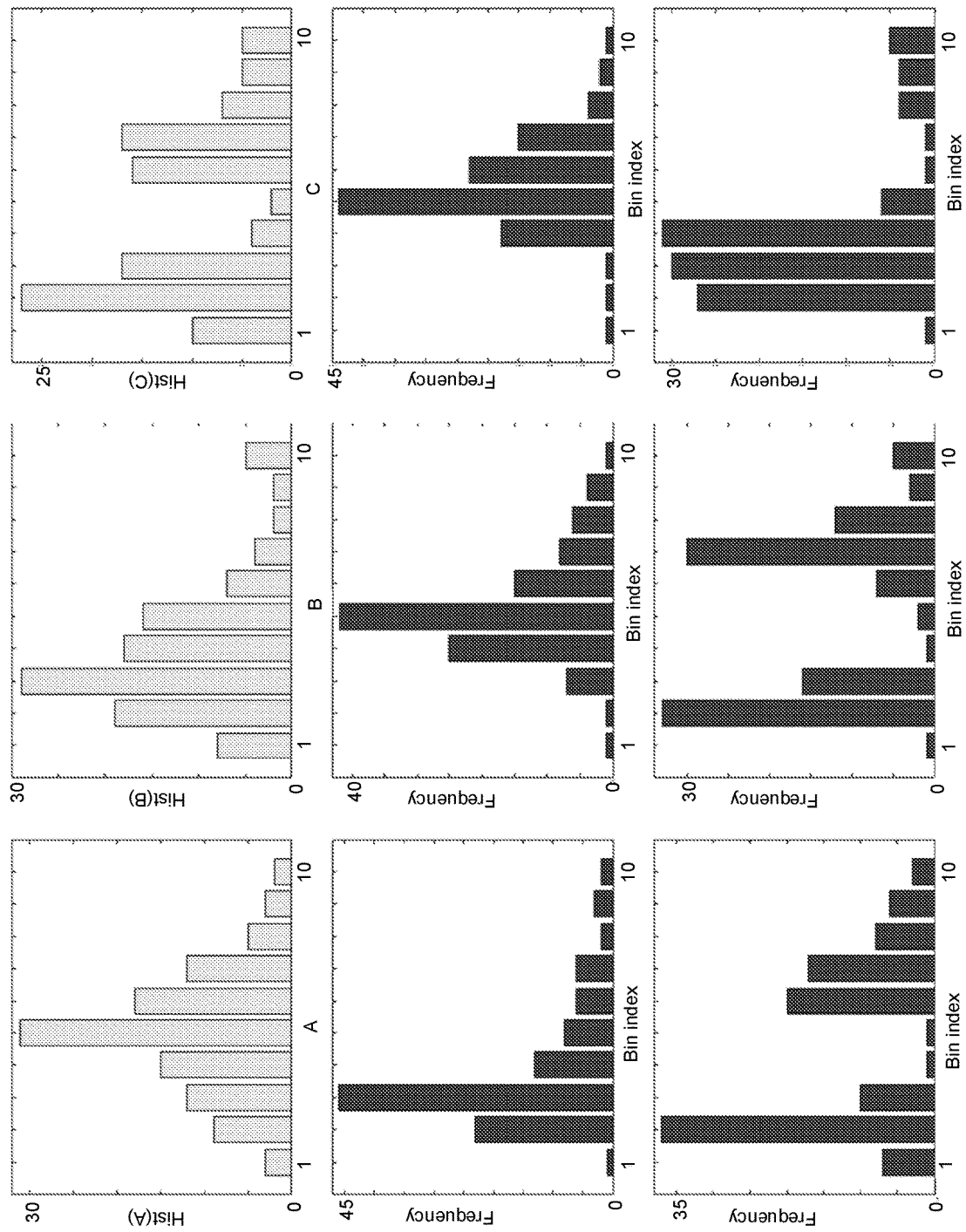
FIG. 39 is a plot of the form shown in FIG. 35 with the exception that the data for the respective parent nodes (A, first column, B, second column, and C, third column) is obtained from a Poisson distribution and the interaction functions for the child nodes are nonlinear, in accordance with an embodiment of the present disclosure.

In FIG. 39, data for the parent node is obtained from a Poisson distribution and the interaction functions for the child nodes are nonlinear.

Figure 40:
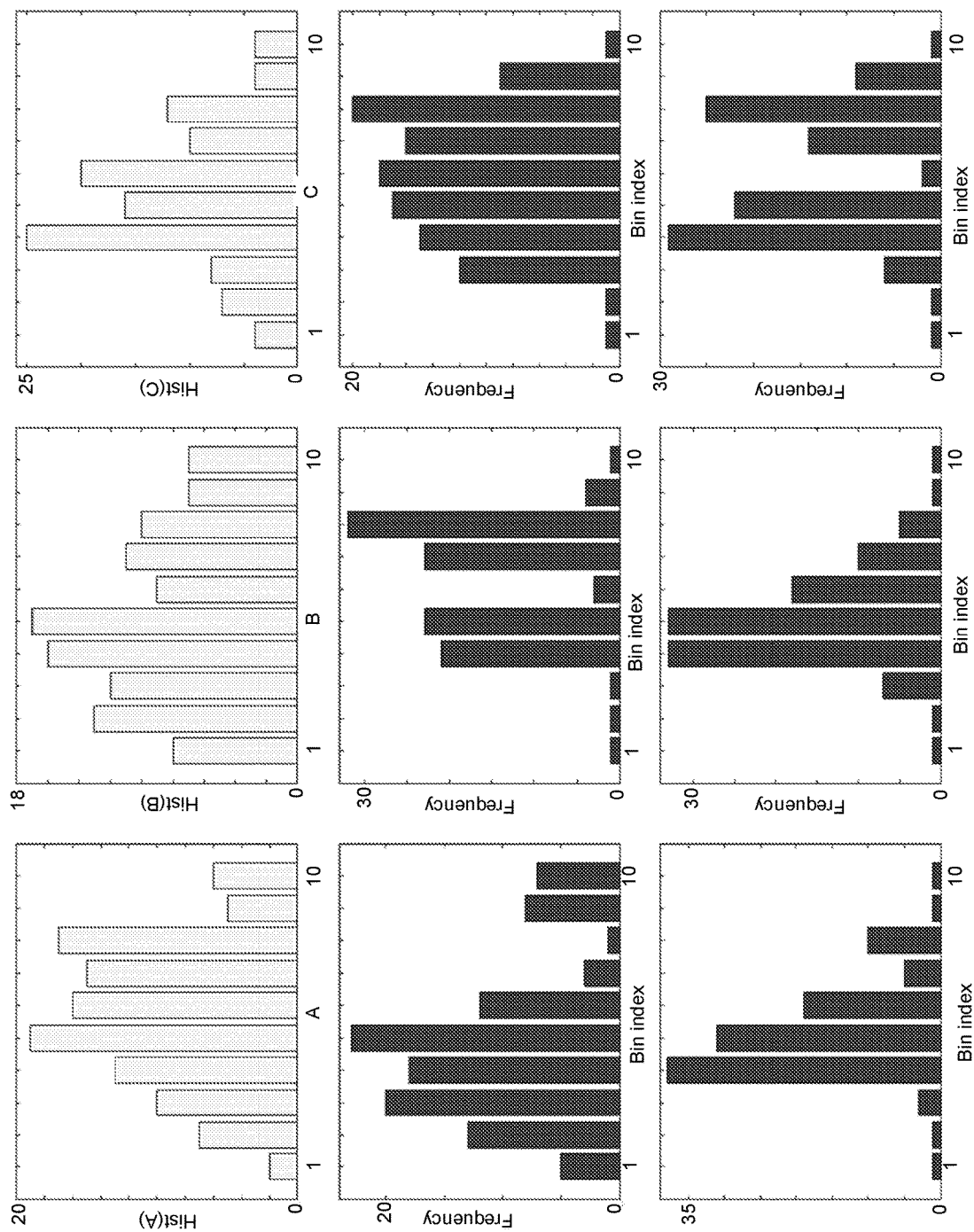
FIG. 40 is a plot of the form shown in FIG. 35 with the exception that the data for the respective parent nodes (A, first column, B, second column, and C, third column) is obtained from a Gaussian distribution and the interaction functions for the child nodes are nonlinear, in accordance with an embodiment of the present disclosure.

In FIG. 40, data for the parent node is obtained from a Gaussian distribution and the interaction functions for the child nodes are nonlinear.

The results are summarized in Table 1. Each row in Table 1 describes a combination of interaction functions and node distributions under high noise conditions (corresponding to FIGS. 35-40). The ground-truth model is $G_1$, with $G_2$ and $G_3$ compared to $G_1$ having one and two wrong causal edges, respectively.

Figure 41:
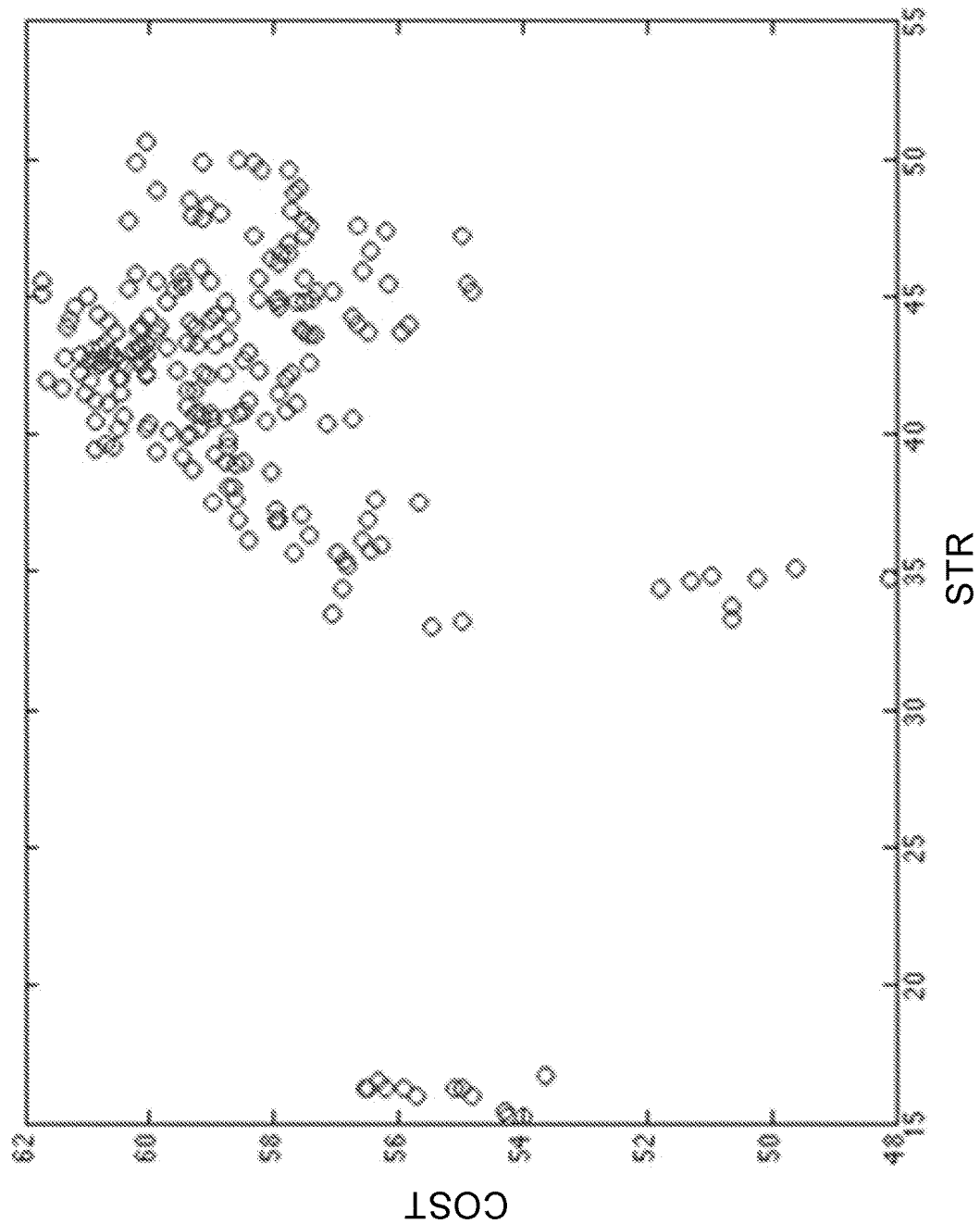
FIG. 41 depicts a scatter plot of the daily price of COST and STR stocks, plotted as coordinate (STR, COST) during an entire year, in accordance with an embodiment of the present disclosure.
Figure 42:
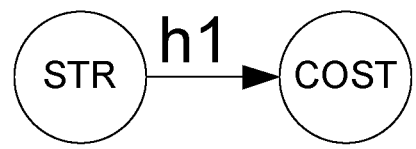
FIG. 42 depicts the two hypotheses on the direction of the causality that were tested h1: STR→COST and h2: STR←COST, accordance with an embodiment of the present disclosure.
Figure 42:
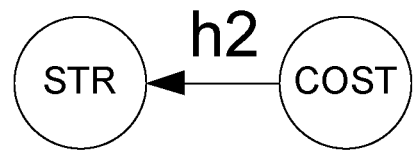

Causal Relationships in Stock Returns with Temporal Logic Based Methods," arXiv:1006.1791, which is hereby incorporated by reference herein in its entirety, it is known that the price of the stock STR (Questar Corporation, a natural gas-focused energy company based in Salt Lake City, Utah) has a causal effect on the stock price of COST (Costco Wholesale Corporation, a membership-only warehouse club that provides a wide selection of merchandise). The disclosed systems and methods for inferring the direction of causality between STR and COST stocks based on the real daily stock returns were test using the CRSP database in the S&P 500 between Aug. 21, 2009 and Jul. 21, 2010. See http://pages.swcp.com/stocks/#historical%20data. The scatter plot of the data samples is shown in FIG. 41. As illustrated in FIG. 42, the two hypotheses on the direction of the causality that were tested using the disclosed systems and methods were h1: STR→COST and h2: STR←COST, as shown in FIG. 42.

The disclosed systems and methods correctly inferred the direction of causality between STR and COST based on the given data, i.e. the correct hypothesis (h1) returns a smaller Kullback-Leibler divergence and larger score than the incorrect hypothesis (h2). The resulting distance and score metrics of h1 and h2 is listed in Table 2.

TABLE 1

Equivalent Markov Structure Causality Inference, Err. = normal KL-divergence, Score = $-\log(\text{Err.})$ $G_i/G_j$ = $\text{Score}_i/\text{Score}_j$

| | $G_1$ (ground truth) | | | $G_2$ | | $G_3$ | |
|---|---|---|---|---|---|---|---|
| Noise | A→B/B→C | Err.\|Score | A←B/B→C | Err.\|Score\|(G1/G2) | A←B/B←C | Err.\|Score\|(G1/G3) |
| hill.U | 0.1148\|0.1128 | 0.2276\|1.4802 | 0.1959\|0.1186 | 0.3145\|1.1568\|1.2796 | 0.2148\|0.1833 | 0.3981\|0.9211\|1.6070 |
| hill.P | 0.1148\|0.1605 | 0.2753\|1.2898 | 0.1874\|0.1295 | 0.3169\|1.1492\|1.1223 | 0.1900\|0.2209 | 0.4109\|0.8894\|1.4502 |
| hill.G | 0.0400\|0.0902 | 0.1302\|2.0387 | 0.0776\|0.1834 | 0.2610\|1.3432\|1.5178 | 0.1967\|0.2095 | 0.4062\|0.9009\|2.2629 |
| nm.U | 0.1582\|0.1726 | 0.3308\|1.1062 | 0.2955\|0.1488 | 0.4443\|0.8113\|1.3635 | 0.2176\|0.3128 | 0.5304\|0.6341\|1.7445 |
| nm.P | 0.1449\|0.0659 | 0.2108\|1.5568 | 0.1442\|0.1838 | 0.3280\|1.1147\|1.3966 | 0.2227\|0.2136 | 0.4363\|0.8294\|1.8770 |
| nm.G | 0.1149\|0.1971 | 0.3120\|1.1648 | 0.3097\|0.1855 | 0.4952\|0.7028\|1.6574 | 0.1687\|0.3527 | 0.5214\|0.6512\|1.7887 |

The disclosed systems and methods address one significant limitation towards finding causal relationships by providing a method to infer causality from correlation-based data utilizing a Bayesian belief inference framework that is capable of distinguishing between Markov equivalent structures. By assuming different functional forms of the interactions that are possible among molecular features, observed data can be fit to probabilistic models of these relationships to assess which model best predicts the observed data. The method is able to achieve good power in resolving causality by appropriately constraining the parameters of the probabilistic model in a way that allows the putative deterministic relationship between two variables to be assessed in a probabilistic framework. The data provided herein shows the algorithm applied to multiple synthetic gene expression and RNA sequencing datasets to demonstrate that the disclosed systems and methods accurately infer causality under different biologically realistic assumptions regarding interaction types and noise structures.

Example 3—Identifying the Correct Causal Relationship Between a Pair of Stocks Based on their Historical Prices In another example of the application of the systems and methods of the present disclosure, the correct causal relationship is predicted between a pair of stocks based on their historic prices. From Kleinberg et al., 2010, "Investigating

TABLE 2

Causality Inference results for two historically related stock prices

| Causality | KL-div | Score |
|---|---|---|
| h1: STR->COST | 0.098249 | 2.32024 |
| h2: STR<-COST | 0.354615 | 1.03672 |

Example 4—Inferring Metabolic Signaling Pathways in Yeast

In this example the disclosed causal inference procedure was tested on synthetic data simulated to represent relationships that are common in biological systems, and on data generated from a dynamical systems model to recover metabolic network models. For the simulation experiment, a large number synthetic datasets were generated based on different nonlinear functions from the more difficult triple-node structures that are Markov equivalent. To infer known metabolic networks, the disclosed systems and methods were applied to yeast data generated from a metabolic model to demonstrate the ability to recover known metabolic networks.

Figure 43:
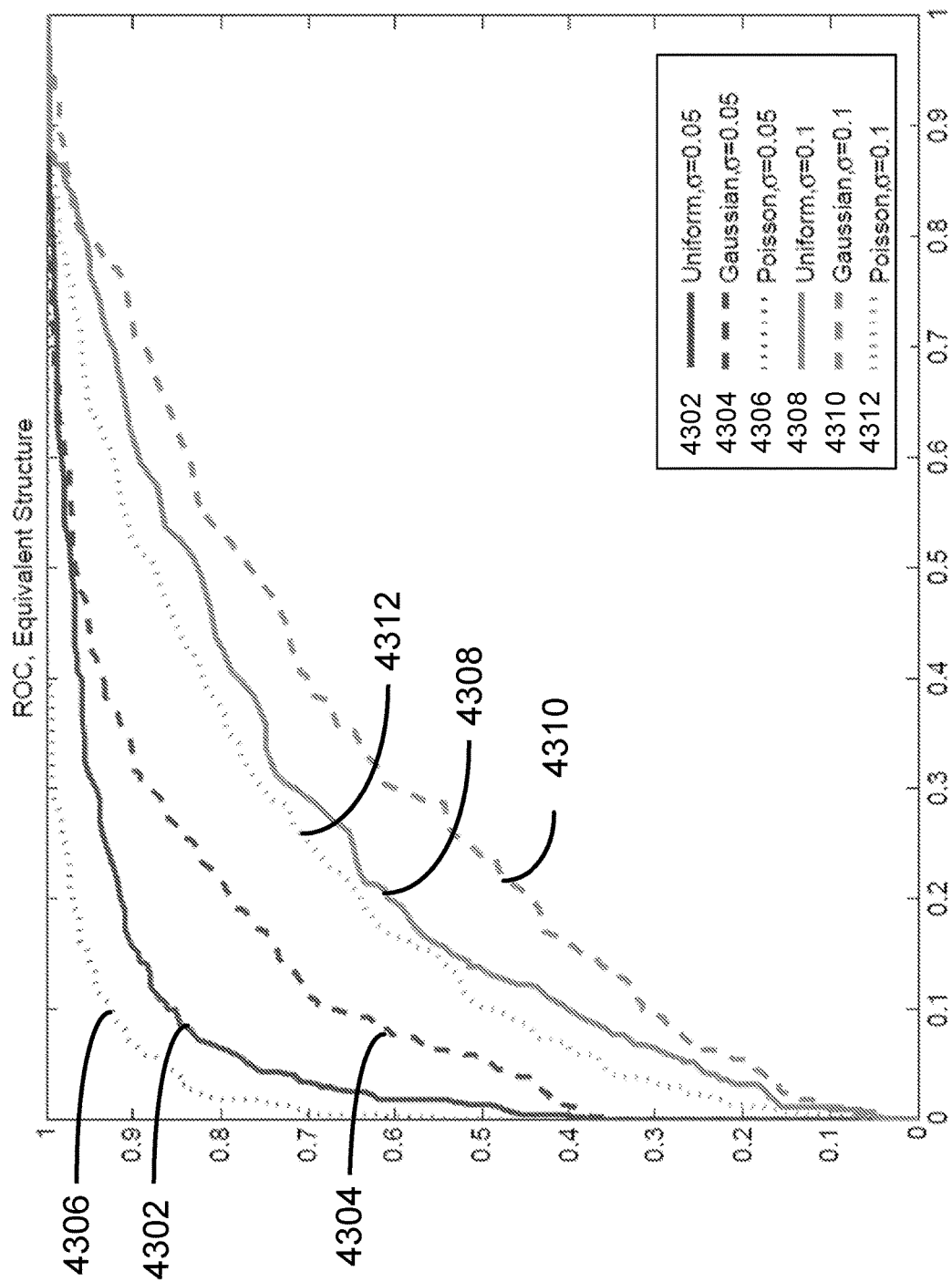
FIG. 43 illustrates the receiver operator characteristic curves based upon generated data in accordance with an embodiment of the present disclosure.

For this problem, the nonlinear functions $y=ax^3+\sin(k\pi x)$ and $z=by^2+\sin(k\pi x)$ to model equivalent structures. These functions represent a flexible framework for representing known biological relationships such as activation/inhibition and feedback control relationships, with the parameters a, b and k controlling the nonlinear features of such relationships. To demonstrate the broad applicability of the disclosed systems and methods to general nonlinear data, the parameters were varied across a wide range of values. For the simulation component of this example, 1000 datasets were generated for each of the three scenarios ($G_1$, $G_2$, and $G_3$) depicted in FIG. 2, with each dataset comprised of 100 samples (a typical sample size in biological experiments). The data were simulated based on the ground truth structure $G_1$ shown in FIG. 2. The data were simulated from different distributions: Uniform (U), Gaussian (G) and Poisson (P), to mimic microarray and RNA-sequencing gene expression data. For each simulation, the parent node A was sampled from the U, G and P distributions, and the child nodes (B and C) were then generated according to the above nonlinear function. Gaussian noise (0, $\sigma^2$) was also simulated to reflect technological variation inherent in the types of measures made in biology. This noise was added to the values of A, B and C to complete the generation of our observation data D. The graphical structures ($G_1$, $G_2$, and $G_3$) depicted in FIG. 2 are Markov equivalent and so in the context of conventional Bayesian networks they all give rise to the same data likelihood, and thus, are statistically indistinguishable from one another. The learning performance of this generated data is illustrated by the receiver operator characteristic (ROC) curves of FIG. 43, in which the ROC curve 4302 is based upon the uniform data in which $\sigma$ is 0.05, the ROC curve 4304 is based upon the Gaussian data in which $\sigma$ is 0.05, the ROC curve 4306 is based upon the Poisson data in which $\sigma$ is 0.05, the ROC curve 4308 is based upon the uniform data in which $\sigma$ is 0.1, the ROC curve 4310 is based upon the Gaussian data in which $\sigma$ is 0.10, and the ROC curve 4312 is based upon the Poisson data in which $\sigma$ is 0.10. The disclosed systems and methods infer the correct causal relationships among the Markov equivalent structures, given the explicit assumptions made on the nature of the interaction between the parent and child nodes and on the distribution of these nodes.

The disclosed systems and methods were then applied to metabolic data generated from a yeast model to assess whether a known metabolic pathway, trehalose biosynthesis, could be correctly identified. Trehalose functions as a carbohydrate reservoir and has recently been shown to play a role in stabilizing proteins and cellular membranes under stress conditions such as heat shock. The metabolic pathway that produces trehalose is believed to regulate glucose uptake, particularly when the cell exists in a high-stress environment. It has also been shown that trehalose 6-phosphate (T6P), an intermediate of trehalose biosynthesis, plays a role in the control of glycolytic flux. The kinetic values of this dynamical model have been identified experimentally (Smallbone, 2011, Chapter eighteen "Building a Kinetic Model of Trehalose Biosynthesis in *Saccharomyces cerevisiae*," *Methods of Enzymology*, Academic Press 500, pp. 355-370, hereby incorporated herein by reference) and are represented in the BioModels Database, (accession number BIOMD0000000380), (Li et al, 2010, "BioModels Database: An enhanced, curated and annotated resource for published quantitative kinetic models," BMC Systems Biology 4-1, which is hereby incorporated by reference.)

The data for the trehalose biosynthetic pathway was generated using the kinetic model for this model represented in the BioModel database. This model is comprised of a cycle of reactions between 11 different metabolites: external glucose (GLX), cellular glucose (GLC), glucose 6-phosphate (G6P), fructose 6-phosphate (F6P), glucose 1-phosphate (G1P), uridine triphosphate (UTP), uridine diphosphate (UDP), uridine diphosphate-glucose (UDG), diphosphate (Pi), trehalose 6-phosphate (TGP), and trehalose (TRH). These metabolites can be divided into two groups, the primary metabolites (M=7) whose concentrations vary as a result of reactions in this pathway, and extracellular glucose and boundary metabolites whose concentrations are fixed but they impact the reaction rates.

Figure 44:
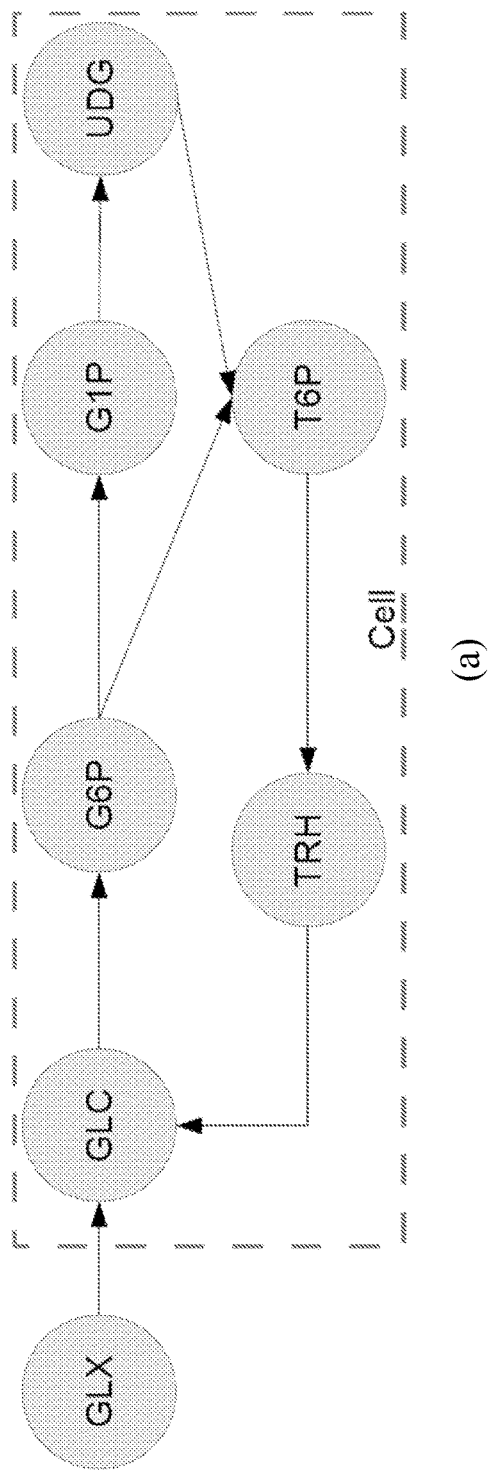
FIG. 44(a) depicts the core causal signaling network for the trehalose biosynthetic pathway.
FIG. 44(b) depicts the corresponding undirected skeleton of the network of FIG. 44(a).
Figure 44:
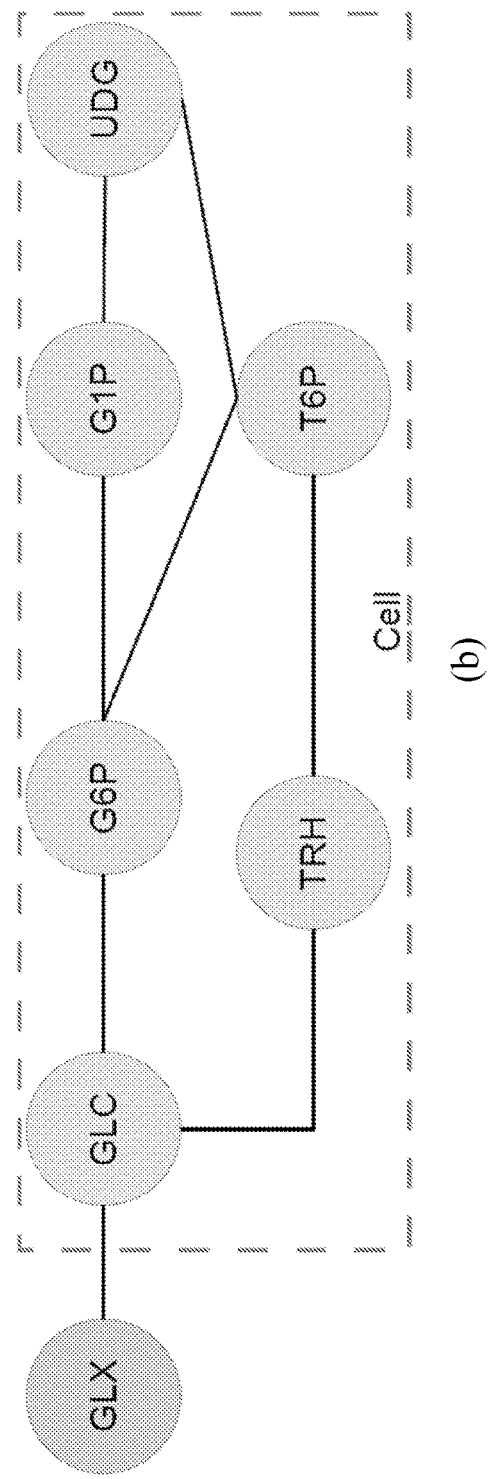
Figure 45:
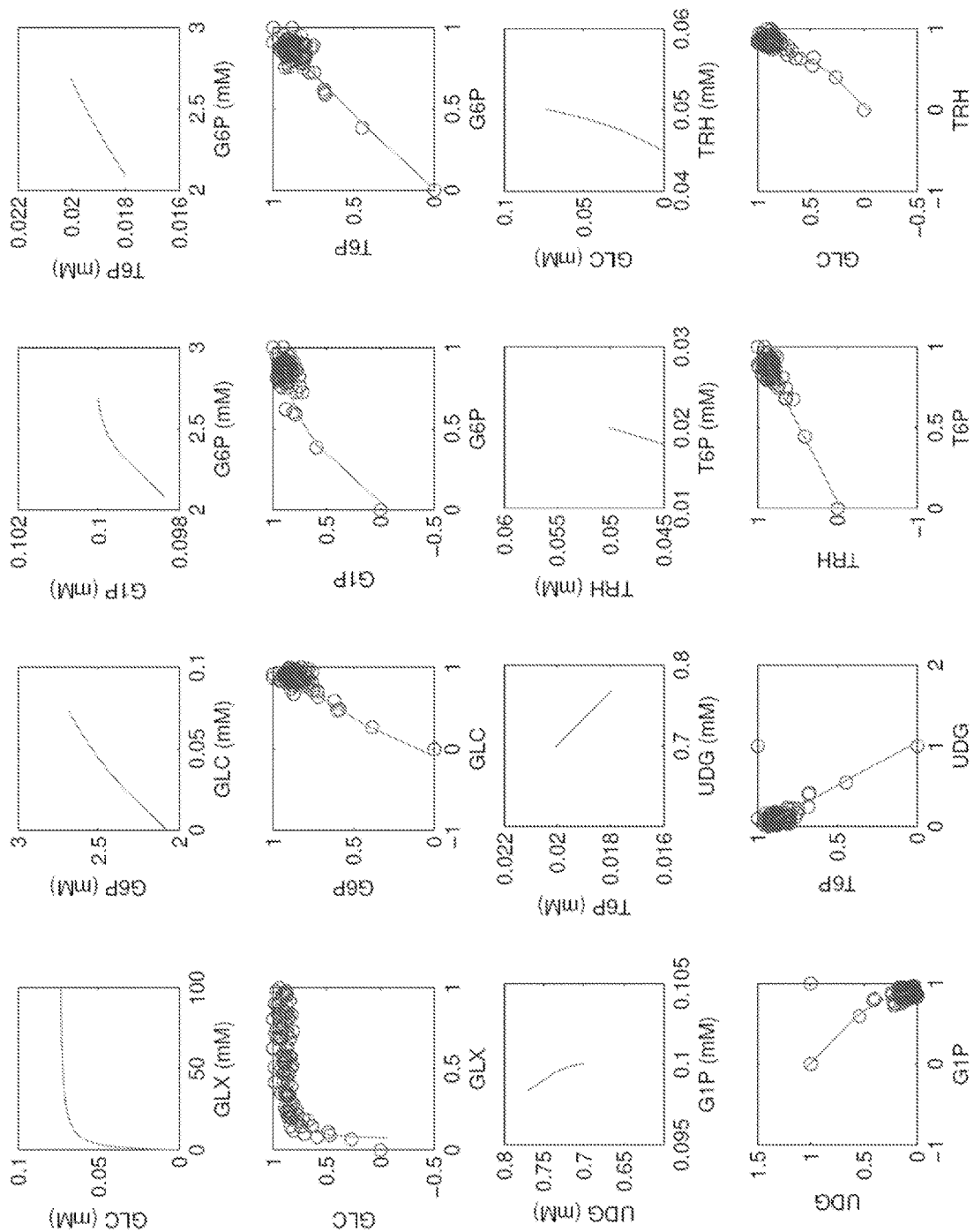
FIG. 45 illustrates the observed data, i.e. steady-state concentration of metabolites in the trehalose pathway given variations in starting extracellular glucose concentrations before and after application of Gaussian noise for data generated to elucidate the network of FIG. 44(a) in accordance with an embodiment of the present disclosure.

FIG. 44(a) depicts the core causal signaling network to be recovered using the causal inference procedure of the disclosed systems and methods. Represented in this network is a v-structure and feedback loop, structures that cannot be unambiguously resolved using classic Bayesian network approaches. The corresponding undirected skeleton of this network is illustrated in FIG. 44(b). To infer causality along each undirected (bold) edge, a dataset was generated by sampling 100 starting concentrations of extracellular glucose (Smallbone, 2011, Chapter eighteen "Building a Kinetic Model of Trehalose Biosynthesis in *Saccharomyces cerevisiae*," *Methods of Enzymology*, Academic Press 500, pp. 355-370, hereby incorporated herein by reference) (changing the medium) $X_{glx}^0$ from the interval [0,100]. For each starting condition the dynamic system representing the trehalose biosynthetic pathway is permitted to evolve to its new steady-state, generating a vector of steady state values for every primary metabolite, for each of the 100 starting conditions. This procedure resulted in a 100×7 data matrix of primary metabolite steady-state concentrations. In addition, Gaussian noise was simulated by adding these noise components to the data matrix. The final observation dataset is shown in FIG. 45. Each subplot describes the relationship of the steady-state concentrations between two (undirected) neighbor nodes in the pathway given the 100 different external glucose concentration starting conditions. Curves without circles show the steady-state values before adding noise, while curves with circles show the rescaled values with the noise terms added, which represent the data used for the causal inference.

Figure 46:
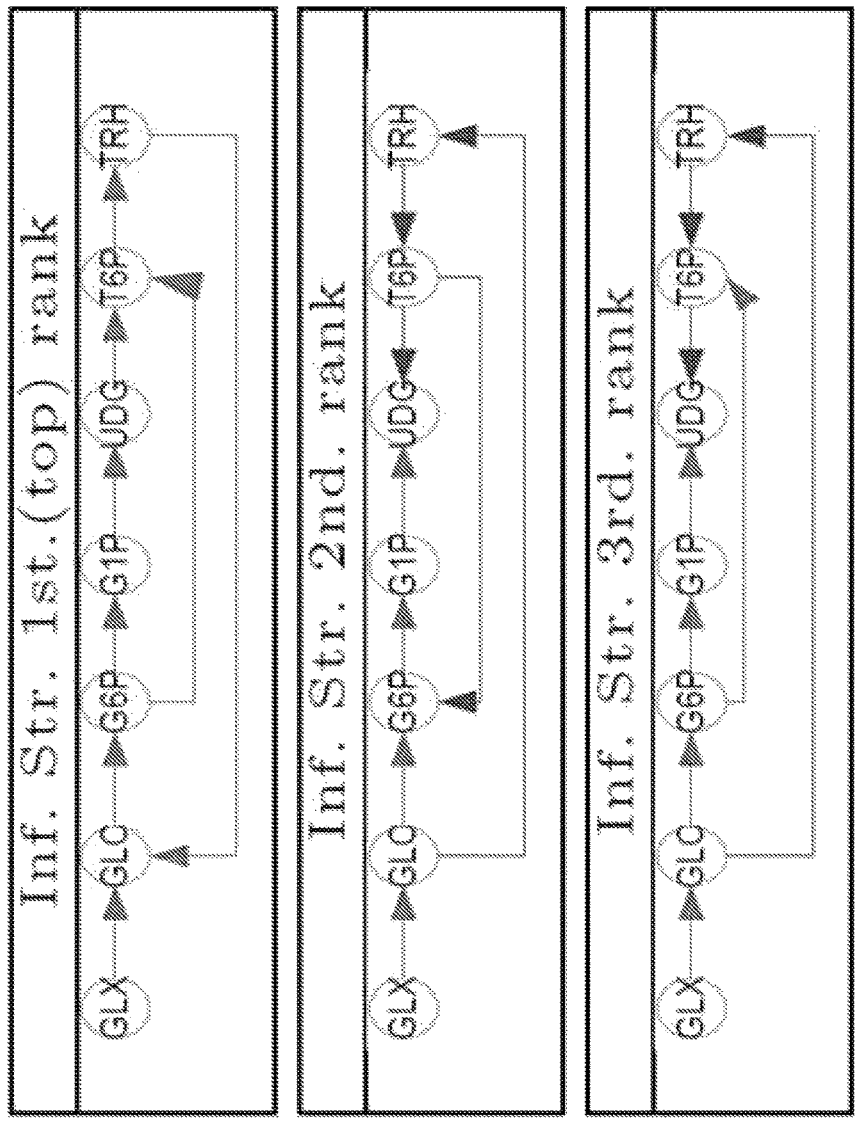
FIG. 46 illustrates the top three causal structures inferred for the trehalose biosynthetic pathway based upon the data of FIG. 45 in accordance with an embodiment of the present disclosure.

Given the connectivity structure of this network, the systems and methods in accordance with one embodiment of the present disclosure were applied to resolve the edge direction by calculating the causal structure score (Eq. 7) for each of the possible causal configurations. Given there are a total eight edges in this network and that each edge can be oriented in one of two possible directions, there are 256 possible causal configurations to consider. The causal structure with the highest score was selected as the most likely causal structure supported by the data. In FIG. 46, the top three inferred causal structures are provided. In FIG. 47 the causality scores for the top three inferred causal structures is also provided. From this, it is seen that inferred top structure is the true causal network. The correct causal structure was inferred by considering the global structure of this network, as opposed to resolving the structure using pairwise causal relationships. One of the unique features of the disclosed modeling approach is the ability to propagate information through the entire network. As a result, our global causal inference approach can leverage the correctly inferred causal relationships as between a given pair of nodes to infer the appropriate causal relationships among other nodes. This feature of the disclosed modeling approach is demonstrated by the causal inference of the feedback loop, i.e. TRH→GLC. With existing causal inference procedures, the inferred causal relationship would be estimated as GLC→TRH, whereas the disclosed systems and methods appropriately leveraged the global structure to correctly infer this edge, given the fitness of GLC, G1P and UDG is improved when the feedback in the top structure is considered, compared to the other competing structures.

CONCLUSION

The terminology used in the description of the invention herein is for the purpose of describing particular implementations only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

All references cited herein are incorporated herein by reference in their entirety and for all purposes to the same extent as if each individual publication or patent or patent application was specifically and individually indicated to be incorporated by reference in its entirety for all purposes.

The foregoing description, for purpose of explanation, has been described with reference to specific implementations. However, the illustrative discussions above are not intended to be exhaustive or to limit the invention to the precise forms disclosed. Many modifications and variations are possible in view of the above teachings. The implementations described herein were chosen and described in order to best explain the principles of the invention and its practical applications, to thereby enable others skilled in the art to best utilize the invention and various implementations with various modifications as are suited to the particular use contemplated.

What is claimed is:

1. A method of perturbing a system, the method comprising:
   at a computer system comprising hardware memory and one or more hardware processors:
   (A) obtaining a set of directed acyclic/cyclic graph candidates $\{G_1, \ldots, G_N\}$ for the system, wherein
       N is 5 or greater, and
       each respective directed acyclic/cyclic graph candidate $G_i$ in at least a subset of $\{G_1, \ldots, G_N\}$ includes one or more causal relationships among nodes in a first plurality of nodes, wherein each causal relationship includes a parent node that is causal for a child node, and wherein two or more nodes in each respective directed acyclic/cyclic graph candidate $G_i$ in at least a subset of $\{G_1, \ldots, G_N\}$ are Markov equivalent;
   (B) obtaining observed data D for the first plurality of nodes;
   (C) for each respective $G_i$ in at least the subset of $\{G_1, \ldots, G_N\}$:
       clamping the marginal probability of a parent node $x_i$ identified in the respective $G_i$ based upon the observed data D,
       computing a distribution of marginal probabilities for a corresponding child node $y_i$ of $x_i$ identified in the respective $G_i$, wherein the computation is performed by Bayesian network belief propagation using an interaction function of the form $y_i = f(x_i)$, and
       quantifying the relationship between the observed distribution for the child node $y_i$ in D to the computed distribution of marginal probabilities for the child node $y_i$ using a nonparametric function, thereby obtaining a nonparametric score for the respective $G_i$;
   (D) selecting a directed acyclic/cyclic graph from $\{G_1, \ldots, G_N\}$ based at least in part upon the quantified nonparametric score for the selected directed acyclic/cyclic graph; and
   (E) perturbing the system using a perturbation that relies at least in part upon the causal relationship between the parent node x and the child node y identified in the selected directed acyclic/cyclic graph, wherein
       a parent node $x_i$ of a first $G_i$ in $\{G_1, \ldots, G_N\}$ is different than a parent node $x_j$ of a second $G_j$ in $\{G_1, \ldots, G_N\}$, and
       the system comprises a biological pathway in a living organism and the perturbation is a pharmaceutical composition.

2. The method of claim 1, wherein the nonparametric function is an f-divergence function.

3. The method of claim 1, wherein the nonparametric function is KL-divergence and the quantifying the relationship between the observed distribution for the child node $y_i$ in D to the computed distribution of marginal probabilities for the child node $y_i$ using a nonparametric function comprises:
   dividing the range of the observed data in D for the parent node $x_i$ of the respective $G_i$ into L segments, wherein $D \in R$ is rescaled to $D \in [0,1]$; and
   maximizing the data likelihood function $P(D|G_i, \hat{\theta})$ in each of the L segments, wherein $\hat{\theta}$ is sampled uniformly in $[0,1]$, by identifying the parameter $\hat{\theta}^l$ that minimizes KL-divergence between the observed distribution for the child node $y_i$ to the computed distribution of marginal probabilities for the child node $y_i$ for each segment in L.

4. The method of claim 3, wherein the parameter $\hat{\theta}^l$ that minimizes KL-divergence for a segment in L is computed as:

$$\operatorname*{argmin}_{\theta} \left\{ \sum_{k=0}^{K} p_k^l \ln(p_k^l / q_k^l) + \sum_{k=0}^{K} q_k^l \ln(q_k^l / p_k^l) \right\}.$$

wherein,
a total of K bins are defined that are evenly distributed in $[0,1]$,
$p_k^l$ = the frequency for the marginal probabilities for the child node in the $k^{th}$ bin and the $l^{th}$ segment, and
$q_k^l$ = the frequency for the observed child data from D in the $k^{th}$ bin and the $l^{th}$ segment.

5. The method of claim 1, wherein the interaction function $y_i = f(x_i)$ is a linear function, a non-linear function, a monotonic function, a non-monotonic function, a concave function, a step function, a periodic function, a hill function, or a non-monotonic nonlinear function.

6. The method of claim 1, wherein the Bayesian network belief propagation is performed by a join-tree propagation, cut-set conditioning, or a hybrid thereof.

7. The method of claim 1, wherein the Bayesian network belief propagation is performed by stochastic simulation.

8. The method of claim 1, wherein the quantifying the relationship between the observed distribution for the child node $y_i$ in D to the computed distribution of marginal probabilities for the child node $y_i$ using a nonparametric function comprises representing a relationship between $x_i$ and $y_i$ as a cubic spline.

9. The method of claim 1, wherein the parent node is part of a v-structure or a feedback loop.

10. The method of claim 1, wherein each directed acyclic/cyclic graph candidate $G_i$ in $\{G_1, \ldots, G_N\}$ includes a plurality of causal relationships among nodes in the first plurality of nodes and the computing the distribution of marginal probabilities for a corresponding child node $y_i$ of $x_i$ identified in the respective G comprises performing Bayesian network belief propagation across a plurality of causal relationships among nodes in the first plurality of nodes.

11. The method of claim 1, wherein
the biological pathway is a metabolic pathway,
each node in the plurality of nodes is a metabolite in the metabolic pathway,
the observed data D is metabolite steady-state concentration data, and
each directed acyclic/cyclic graph candidate Gin at least a subset of $\{G_1, \ldots, G_N\}$ is a different model of causal dependencies between metabolites in the metabolic pathway.

12. The method of claim 1, wherein
each node in the first plurality of nodes is a cellular constituent in a plurality of cellular constituents, and
the observed data is cellular constituent abundance data.

13. The method of claim 12, wherein the cellular constituent a nucleic acid, a ribonucleic acid, a protein, or a metabolite.

14. The method of claim 1, wherein a respective $G_i$ in $\{G_1, \ldots, G_N\}$ is cyclic and the computing the distribution of marginal probabilities for a corresponding child node $y_i$ of $x_i$ identified in the respective $G_i$, is performed by Dynamic Bayesian network belief propagation.

15. A computing device, comprising:
one or more processors;
memory; and
one or more programs stored in the memory configured for execution by the one or more processors, the one or more programs comprising instructions for:
(A) obtaining a set of directed acyclic/cyclic graph candidates $\{G_1, \ldots, G_N\}$ for the system, wherein
N is 5 or greater, and
each respective directed acyclic/cyclic graph candidate $G_i$ in at least a subset of $\{G_1, \ldots, G_N\}$ includes one or more causal relationships among nodes in a first plurality of nodes, wherein each causal relationship includes a parent node that is causal for a child node, and wherein two or more nodes in each respective directed acyclic/cyclic graph candidate $G_i$ in at least a subset of $\{G_1, \ldots, G_N\}$ are Markov equivalent;
(B) obtaining observed data D for the first plurality of nodes;
(C) for each respective $G_i$ in at least the subset of $\{G_1, \ldots, G_N\}$:
clamping the marginal probability of a parent node $x_i$ identified in the respective $G_i$ based upon the observed data D,
computing a distribution of marginal probabilities for a corresponding child node $y_i$ of $x_i$ identified in the respective wherein the computation is performed by Bayesian network belief propagation using an interaction function of the form $y_i = f(x_i)$, and
quantifying the relationship between the observed distribution for the child node $y_i$ in D to the computed distribution of marginal probabilities for the child node $y_i$ using a nonparametric function, thereby obtaining a nonparametric score for the respective $G_i$; and
(D) selecting a directed acyclic/cyclic graph from $\{G_1, \ldots, G_N\}$ based at least in part upon the quantified nonparametric score for the selected directed acyclic/cyclic graph, wherein
a parent node $x_i$ of a first $G_i$ in $\{G_1, \ldots, G_N\}$ is different than a parent node $x_j$ of a second $G_j$ in $\{G_1, \ldots, G_N\}$, and
the system comprises a biological pathway in a living organism and the perturbation is a pharmaceutical composition.

16. The computing device of claim 15, wherein the one or more programs further comprise instructions for:
(E) perturbing the system using a perturbation that relies at least in part upon the causal relationship between the parent node x and the child node y identified in the selected directed acyclic/cyclic graph.

17. The computing device of claim 15, wherein the nonparametric function is KL-divergence and the quantifying the relationship between the observed distribution for the child node $y_i$ in D to the computed distribution of marginal probabilities for the child node $y_i$ using a nonparametric function comprises:
dividing the range of the observed data in D for the parent node $x_i$ of the respective $G_i$ into L segments, wherein D∈R is rescaled to D∈[0,1]; and
maximizing the data likelihood function $P(D|G_i,\hat{\theta})$ in each of the L segments, wherein $\hat{\theta}$ is sampled uniformly in [0,1], by identifying the parameter $\hat{\theta}^l$ that minimizes KL-divergence between the observed distribution for the child node $y_i$ to the computed distribution of marginal probabilities for the child node $y_i$ for each segment in L.

18. A non-transitory computer readable storage medium storing one or more programs configured for execution by a computing device having one or more processors and memory, the one or more programs comprising instructions for:
(A) obtaining a set of directed acyclic/cyclic graph candidates $\{G_1, \ldots, G_N\}$ for the system, wherein
N is 5 or greater, and
each respective directed acyclic/cyclic graph candidate $G_i$ in at least a subset of $\{G_1, \ldots, G_N\}$ includes one or more causal relationships among nodes in a first plurality of nodes, wherein each causal relationship includes a parent node that is causal for a child node, and wherein two or more nodes in each respective directed acyclic/cyclic graph candidate $G_i$ in at least a subset of $\{G_1, \ldots, G_N\}$ are Markov equivalent;
(B) obtaining observed data D for the first plurality of nodes;
(C) for each respective $G_i$ in at least the subset of $\{G_1, \ldots, G_N\}$:
clamping the marginal probability of a parent node $x_i$ identified in the respective $G_i$ based upon the observed data D,
computing a distribution of marginal probabilities for a corresponding child node $y_i$ of $x_i$ identified in the respective $G_i$, wherein the computation is performed by Bayesian network belief propagation using an interaction function of the form $y_i = f(x_i)$, and
quantifying the relationship between the observed distribution for the child node $y_i$ in D to the computed distribution of marginal probabilities for the child node $y_i$ using a nonparametric function, thereby obtaining a nonparametric score for the respective $G_i$; and (D) selecting a directed acyclic/cyclic graph from $\{G_1, \ldots, G_N\}$ based at least in part upon the quantified nonparametric score for the selected directed acyclic/cyclic graph, wherein a parent node $x_i$ of a first $G_i$ in $\{G_1, \ldots, G_N\}$ is different than a parent node $x_j$ of a second $G_j$ in $\{G_1, \ldots, G_N\}$, and the system comprises a biological pathway in a living organism and the perturbation is a pharmaceutical composition.

19. The non-transitory computer readable storage medium of claim 18, wherein the one or more programs further comprise instructions for:

(E) perturbing the system using a perturbation that relies at least in part upon the causal relationship between the parent node x and the child node y identified in the selected directed acyclic/cyclic graph.

20. The non-transitory computer readable storage medium of claim 18, wherein the nonparametric function is KL-divergence and the quantifying the relationship between the observed distribution for the child node $y_i$ in D to the computed distribution of marginal probabilities for the child node $y_i$ using a nonparametric function comprises:

dividing the range of the observed data in D for the parent node $x_i$ of the respective $G_i$ into L segments, wherein $D \in R$ is rescaled to $D \in [0,1]$; and maximizing the data likelihood function $P(D|G_i, \hat{\theta})$ in each of the L segments, wherein $\hat{\theta}$ is sampled uniformly in $[0,1]$, by identifying the parameter $\hat{\theta}^l$ that minimizes KL-divergence between the observed distribution for the child node $y_i$ to the computed distribution of marginal probabilities for the child node $y_i$ for each segment in L.

\* \* \* \* \*